(12) United States Patent
Saarma et al.

(10) Patent No.: US 8,853,166 B2
(45) Date of Patent: Oct. 7, 2014

(54) NEUROTROPHIC FACTOR MANF AND USES THEREOF

(75) Inventors: Mart Saarma, Helsinki (FI); Päivi Lindholm, Vantaa (FI); Merja Voutilainen, Helsinki (FI); Johan Peränen, Helsinki (FI); Raimo Tuominen, Vantaa (FI); Mikko Airavaara, Annapolis, MD (US); Veli-Matti Leppänen, Otalampi (FI); Maria Lindahl, Espoo (FI); Jaan-Olle Andressoo, Helsinki (FI)

(73) Assignee: Herantis Pharma PLC., Helsinki (FI)

( * ) Notice: Subject to any disclaimer, the term of this patent is extended or adjusted under 35 U.S.C. 154(b) by 714 days.

(21) Appl. No.: 12/433,345

(22) Filed: Apr. 30, 2009

(65) Prior Publication Data

US 2009/0282495 A1 Nov. 12, 2009

Related U.S. Application Data

(60) Provisional application No. 61/052,757, filed on May 13, 2008.

(51) Int. Cl.
*A61P 25/16* (2006.01)
*C07K 14/475* (2006.01)
*A61K 38/18* (2006.01)
*C12Q 1/68* (2006.01)
*C12N 15/12* (2006.01)

(52) U.S. Cl.
USPC ....... 514/17.7; 435/320.1; 435/455; 435/375; 435/6.16; 530/350; 530/399; 514/44 R

(58) Field of Classification Search
None
See application file for complete search history.

(56) References Cited

U.S. PATENT DOCUMENTS

2006/0241035 A1* 10/2006 Onichtchouk .................. 514/12

FOREIGN PATENT DOCUMENTS

| WO | WO 0119851 | * | 1/2001 |
| WO | WO 2005005471 | * | 1/2005 |

OTHER PUBLICATIONS

Lazic and Barker, Cell-based therapies for disorders of the CNS, Expert Opin. Ther. Patents (2005) 15(10): 1361-1376.*
Russell, Replicating Vectors for Gene Therapy of Cancer: Risks, Limitations and Prospects, European j Cancer, 1994. vol. 30A(8), p. 1165-1171.*
Kahle et al, The emerging utility of animal models of chronic neurodegenerative disease, Emerging Therapeutic Targets (2001) 5(1):125-132.*
Opalinska et al, Nucleic-Acid Therapeutics: Basic Principles and Recent Applications, Nature Reviews, 2002, vol. 1, p. 503-514.*
Richardson and Burns, Mouse Models of Alzheimer's Disease: A Quest for Plaques and Tangles, ILAT Journal, 2002, vol. 43 (2), p. 89-99.*
Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*

* cited by examiner

*Primary Examiner* — Maria Marvich
(74) *Attorney, Agent, or Firm* — Birch, Stewart, Kolasch & Birch, LLP.

(57) ABSTRACT

The present invention generally relates to the field of treatment of neuronal disorders and more particularly to neurotrophic factor MANF and uses thereof. The present invention provides a pharmaceutical compound comprising MANF nucleic acid molecule, MANF protein or a functional fragment thereof for the treatment of a peripherial neuropathy including Alzheimer's disease, Parkinson's disease, epilepsy, drug addiction and ischemic brain injury.

1 Claim, 31 Drawing Sheets

DIFFUSION STUDIES: MANF & GDNF
Immunohistochemistry (24 h)

Anti-MANF-staining

Anti-GDNF-staining

SEQUENCE LISTING

<160> NUMBER OF SEQ ID NOS: 14

<210> SEQ ID NO 1
<211> LENGTH: 540
<212> TYPE: DNA
<213> ORGANISM: Homo sapiens
<220> FEATURE:
<221> NAME/KEY: CDS
<222> LOCATION: (1)..(540)

<400> SEQUENCE: 1

```
atg tgg gcc acg cag ggg ctg gcg gtg gcg ctg gct ctg agc gtg ctg      48
Met Trp Ala Thr Gln Gly Leu Ala Val Ala Leu Ala Leu Ser Val Leu
1               5                   10                  15 ccg ggc agc cgg gcg ctg cgg ccg ggc gac tgc gaa gtt tgt att tct      96
Pro Gly Ser Arg Ala Leu Arg Pro Gly Asp Cys Glu Val Cys Ile Ser
                20                  25                  30 tat ctg gga aga ttt tac cag gac ctc aaa gac aga gat gtc aca ttc     144
Tyr Leu Gly Arg Phe Tyr Gln Asp Leu Lys Asp Arg Asp Val Thr Phe
            35                  40                  45 tca cca gcc act att gaa aac gaa ctt ata aag ttc tgc cgg gaa gca     192
Ser Pro Ala Thr Ile Glu Asn Glu Leu Ile Lys Phe Cys Arg Glu Ala
        50                  55                  60 aga ggc aaa gag aat cgg ttg tgc tac tat atc ggg gcc aca gat gat     240
Arg Gly Lys Glu Asn Arg Leu Cys Tyr Tyr Ile Gly Ala Thr Asp Asp
65                  70                  75                  80 gca gcc acc aaa atc atc aat gag gta tca aag cct ctg gcc cac cac     288
Ala Ala Thr Lys Ile Ile Asn Glu Val Ser Lys Pro Leu Ala His His
                85                  90                  95 atc cct gtg gag aag atc tgt gag aag ctt aag aag aag gac agc cag     336
Ile Pro Val Glu Lys Ile Cys Glu Lys Leu Lys Lys Lys Asp Ser Gln
                100                 105                 110 ata tgt gag ctt aag tat gac aag cag atc gac ctg agc aca gtg gac     384
Ile Cys Glu Leu Lys Tyr Asp Lys Gln Ile Asp Leu Ser Thr Val Asp
            115                 120                 125 ctg aag aag ctc cga gtt aaa gag ctg aag aag att ctg gat gac tgg     432
Leu Lys Lys Leu Arg Val Lys Glu Leu Lys Lys Ile Leu Asp Asp Trp
        130                 135                 140 ggg gag aca tgc aaa ggc tgt gca gaa aag tct gac tac atc cgg aag     480
Gly Glu Thr Cys Lys Gly Cys Ala Glu Lys Ser Asp Tyr Ile Arg Lys
145                 150                 155                 160 ata aat gaa ctg atg cct aaa tat gcc ccc aag gca gcc agt gca cgg     528
Ile Asn Glu Leu Met Pro Lys Tyr Ala Pro Lys Ala Ala Ser Ala Arg
                165                 170                 175 acc gat ttg tag                                                     540
Thr Asp Leu
```

<210> SEQ ID NO 2
<211> LENGTH: 179
<212> TYPE: PRT
<213> ORGANISM: Homo sapiens

<400> SEQUENCE: 2

```
Met Trp Ala Thr Gln Gly Leu Ala Val Ala Leu Ala Leu Ser Val Leu
1               5                   10                  15

Pro Gly Ser Arg Ala Leu Arg Pro Gly Asp Cys Glu Val Cys Ile Ser
                20                  25                  30

Tyr Leu Gly Arg Phe Tyr Gln Asp Leu Lys Asp Arg Asp Val Thr Phe
            35                  40                  45

Ser Pro Ala Thr Ile Glu Asn Glu Leu Ile Lys Phe Cys Arg Glu Ala
        50                  55                  60
```

```
Arg Gly Lys Glu Asn Arg Leu Cys Tyr Tyr Ile Gly Ala Thr Asp Asp
 65                  70                  75                  80

Ala Ala Thr Lys Ile Ile Asn Glu Val Ser Lys Pro Leu Ala His His
                 85                  90                  95

Ile Pro Val Glu Lys Ile Cys Glu Lys Leu Lys Lys Lys Asp Ser Gln
            100                 105                 110

Ile Cys Glu Leu Lys Tyr Asp Lys Gln Ile Asp Leu Ser Thr Val Asp
        115                 120                 125

Leu Lys Lys Leu Arg Val Lys Glu Leu Lys Lys Ile Leu Asp Asp Trp
    130                 135                 140

Gly Glu Thr Cys Lys Gly Cys Ala Glu Lys Ser Asp Tyr Ile Arg Lys
145                 150                 155                 160

Ile Asn Glu Leu Met Pro Lys Tyr Ala Pro Lys Ala Ala Ser Ala Arg
                165                 170                 175

Thr Asp Leu

<210> SEQ ID NO 3
<211> LENGTH: 477
<212> TYPE: DNA
<213> ORGANISM: Homo sapiens
<220> FEATURE:
<221> NAME/KEY: CDS
<222> LOCATION: (1)..(477)

<400> SEQUENCE: 3 ctg cgg ccg ggc gac tgc gaa gtt tgt att tct tat ctg gga aga ttt      48
Leu Arg Pro Gly Asp Cys Glu Val Cys Ile Ser Tyr Leu Gly Arg Phe
1               5                  10                  15 tac cag gac ctc aaa gac aga gat gtc aca ttc tca cca gcc act att      96
Tyr Gln Asp Leu Lys Asp Arg Asp Val Thr Phe Ser Pro Ala Thr Ile
            20                  25                  30 gaa aac gaa ctt ata aag ttc tgc cgg gaa gca aga ggc aaa gag aat     144
Glu Asn Glu Leu Ile Lys Phe Cys Arg Glu Ala Arg Gly Lys Glu Asn
        35                  40                  45 cgg ttg tgc tac tat atc ggg gcc aca gat gat gca gcc acc aaa atc     192
Arg Leu Cys Tyr Tyr Ile Gly Ala Thr Asp Asp Ala Ala Thr Lys Ile
    50                  55                  60 atc aat gag gta tca aag cct ctg gcc cac cac atc cct gtg gag aag     240
Ile Asn Glu Val Ser Lys Pro Leu Ala His His Ile Pro Val Glu Lys
65                  70                  75                  80 atc tgt gag aag ctt aag aag aag gac agc cag ata tgt gag ctt aag     288
Ile Cys Glu Lys Leu Lys Lys Lys Asp Ser Gln Ile Cys Glu Leu Lys
                85                  90                  95 tat gac aag cag atc gac ctg agc aca gtg gac ctg aag aag ctc cga     336
Tyr Asp Lys Gln Ile Asp Leu Ser Thr Val Asp Leu Lys Lys Leu Arg
            100                 105                 110 gtt aaa gag ctg aag aag att ctg gat gac tgg ggg gag aca tgc aaa     384
Val Lys Glu Leu Lys Lys Ile Leu Asp Asp Trp Gly Glu Thr Cys Lys
        115                 120                 125 ggc tgt gca gaa aag tct gac tac atc cgg aag ata aat gaa ctg atg     432
Gly Cys Ala Glu Lys Ser Asp Tyr Ile Arg Lys Ile Asn Glu Leu Met
    130                 135                 140 cct aaa tat gcc ccc aag gca gcc agt gca cgg acc gat ttg tag          477
Pro Lys Tyr Ala Pro Lys Ala Ala Ser Ala Arg Thr Asp Leu
145                 150                 155

<210> SEQ ID NO 4
<211> LENGTH: 158
<212> TYPE: PRT
<213> ORGANISM: Homo sapiens
```

<400> SEQUENCE: 4

Leu Arg Pro Gly Asp Cys Glu Val Cys Ile Ser Tyr Leu Gly Arg Phe
1               5                   10                  15

Tyr Gln Asp Leu Lys Asp Arg Asp Val Thr Phe Ser Pro Ala Thr Ile
            20                  25                  30

Glu Asn Glu Leu Ile Lys Phe Cys Arg Glu Ala Arg Gly Lys Glu Asn
        35                  40                  45

Arg Leu Cys Tyr Tyr Ile Gly Ala Thr Asp Asp Ala Ala Thr Lys Ile
    50                  55                  60

Ile Asn Glu Val Ser Lys Pro Leu Ala His His Ile Pro Val Glu Lys
65                  70                  75                  80

Ile Cys Glu Lys Leu Lys Lys Lys Asp Ser Gln Ile Cys Glu Leu Lys
                85                  90                  95

Tyr Asp Lys Gln Ile Asp Leu Ser Thr Val Asp Leu Lys Lys Leu Arg
            100                 105                 110

Val Lys Glu Leu Lys Lys Ile Leu Asp Asp Trp Gly Glu Thr Cys Lys
        115                 120                 125

Gly Cys Ala Glu Lys Ser Asp Tyr Ile Arg Lys Ile Asn Glu Leu Met
    130                 135                 140

Pro Lys Tyr Ala Pro Lys Ala Ala Ser Ala Arg Thr Asp Leu
145                 150                 155

<210> SEQ ID NO 5
<211> LENGTH: 187
<212> TYPE: PRT
<213> ORGANISM: Homo sapiens

<400> SEQUENCE: 5

Met Trp Cys Ala Ser Pro Val Ala Val Ala Phe Cys Ala Gly Leu
1               5                   10                  15

Leu Val Ser His Pro Val Leu Thr Gln Gly Gln Glu Ala Gly Gly Arg
            20                  25                  30

Pro Gly Ala Asp Cys Glu Val Cys Lys Glu Phe Leu Asn Arg Phe Tyr
        35                  40                  45

Lys Ser Leu Ile Asp Arg Gly Val Asn Phe Ser Leu Asp Thr Ile Glu
    50                  55                  60

Lys Glu Leu Ile Ser Phe Cys Leu Asp Thr Lys Gly Lys Glu Asn Arg
65                  70                  75                  80

Leu Cys Tyr Tyr Leu Gly Ala Thr Lys Asp Ala Ala Thr Lys Ile Leu
                85                  90                  95

Ser Glu Val Thr Arg Pro Met Ser Val His Met Pro Ala Met Lys Ile
            100                 105                 110

Cys Glu Lys Leu Lys Lys Leu Asp Ser Gln Ile Cys Glu Leu Lys Tyr
        115                 120                 125

Glu Lys Thr Leu Asp Leu Ala Ser Val Asp Leu Arg Lys Met Arg Val
    130                 135                 140

Ala Glu Leu Lys Gln Ile Leu His Ser Trp Gly Glu Glu Cys Arg Ala
145                 150                 155                 160

Cys Ala Glu Lys Thr Asp Tyr Val Asn Leu Ile Gln Glu Leu Ala Pro
                165                 170                 175

Lys Tyr Ala Ala Thr His Pro Lys Thr Glu Leu
            180                 185

<210> SEQ ID NO 6
<211> LENGTH: 179
<212> TYPE: PRT
<213> ORGANISM: Mus musculus

<400> SEQUENCE: 6

Met Trp Ala Thr Arg Gly Leu Ala Val Ala Leu Ala Leu Ser Val Leu
1               5                   10                  15

Pro Asp Ser Arg Ala Leu Arg Pro Gly Asp Cys Glu Val Cys Ile Ser
            20                  25                  30

Tyr Leu Gly Arg Phe Tyr Gln Asp Leu Lys Asp Arg Asp Val Thr Phe
        35                  40                  45

Ser Pro Ala Thr Ile Glu Glu Leu Ile Lys Phe Cys Arg Glu Ala
    50                  55                  60

Arg Gly Lys Glu Asn Arg Leu Cys Tyr Tyr Ile Gly Ala Thr Asp Asp
65                  70                  75                  80

Ala Ala Thr Lys Ile Ile Asn Glu Val Ser Lys Pro Leu Ala His His
                85                  90                  95

Ile Pro Val Glu Lys Ile Cys Glu Lys Leu Lys Lys Lys Asp Ser Gln
            100                 105                 110

Ile Cys Glu Leu Lys Tyr Asp Lys Gln Ile Asp Leu Ser Thr Val Asp
        115                 120                 125

Leu Lys Lys Leu Arg Val Lys Glu Leu Lys Lys Ile Leu Asp Asp Trp
130                 135                 140

Gly Glu Met Cys Lys Gly Cys Ala Glu Lys Ser Asp Tyr Ile Arg Lys
145                 150                 155                 160

Ile Asn Glu Leu Met Pro Lys Tyr Ala Pro Lys Ala Ala Ser Ala Arg
                165                 170                 175

Thr Asp Leu

<210> SEQ ID NO 7
<211> LENGTH: 180
<212> TYPE: PRT
<213> ORGANISM: Xenopus laevis

<400> SEQUENCE: 7

Met Leu Pro Leu Ala Leu Leu Thr Val Thr Gly Ile Met Val Leu Leu
1               5                   10                  15

Pro Ser Asp Ala Gly Ala Leu Lys Ala Gly Asp Cys Glu Val Cys Ile
            20                  25                  30

Ser Phe Leu Ser Arg Phe Tyr Gln Ser Leu Lys Glu Arg Lys Val Glu
        35                  40                  45

Phe Lys Pro Asp Ile Val Glu Lys Glu Leu Leu Lys Thr Cys Asn Asp
    50                  55                  60

Ala Arg Gly Lys Glu Asn Arg Leu Cys Tyr Tyr Ile Gly Ala Thr Ser
65                  70                  75                  80

Asp Ala Ala Thr Lys Ile Thr Asn Glu Val Ser Lys Pro Leu Ser Asn
                85                  90                  95

His Ile Pro Pro Glu Lys Ile Cys Glu Lys Leu Lys Lys Lys Asp Gly
            100                 105                 110

Gln Ile Cys Glu Leu Lys Tyr Asp Lys Gln Ile Asp Leu Ser Thr Val
        115                 120                 125

Asp Leu Lys Lys Leu Lys Val Lys Glu Leu Lys Lys Ile Leu Asp Asp
130                 135                 140

```
Trp Gly Glu Ser Cys Lys Gly Cys Ala Glu Lys Ser Asp Phe Ile Arg
145                 150                 155                 160

Lys Ile Asn Glu Leu Met Pro Lys Tyr Ala Pro Asn Ala Ala Asn Ala
                165                 170                 175

Arg Thr Asp Leu
            180

<210> SEQ ID NO 8
<211> LENGTH: 180
<212> TYPE: PRT
<213> ORGANISM: Danio rerio

<400> SEQUENCE: 8

Met Leu Tyr Leu Ser Gly Leu Ser Val Ala Phe Ala Leu Ala Leu Val
1               5                   10                  15

Pro Ser Cys Ser Asp Ala Leu Lys Asp Gly Glu Cys Glu Val Cys Val
            20                  25                  30

Gly Phe Leu Gln Arg Leu Tyr Gln Thr Ile Gln Glu Asn Asn Val Lys
        35                  40                  45

Phe Asp Ser Asp Ser Ile Glu Lys Ala Leu Leu Lys Ser Cys Lys Asp
50                  55                  60

Ala Lys Gly Lys Glu Asn Arg Phe Cys Tyr Tyr Ile Gly Ala Thr Ser
65                  70                  75                  80

Asp Ala Ala Thr Lys Ile Thr Asn Glu Val Ser Lys Pro Met Ser Tyr
                85                  90                  95

His Val Pro Val Glu Lys Ile Cys Glu Lys Leu Lys Lys Lys Asp Ser
            100                 105                 110

Gln Ile Cys Glu Leu Lys Tyr Asp Lys Gln Val Asp Leu Ser Ser Val
        115                 120                 125

Asp Leu Lys Lys Leu Lys Val Lys Asp Leu Lys Lys Ile Leu Glu Glu
130                 135                 140

Trp Gly Glu Ser Cys Lys Gly Cys Val Glu Lys Ser Asp Phe Ile Arg
145                 150                 155                 160

Lys Ile Asn Glu Leu Met Pro Lys Tyr Ala Pro Ser Ala Ala Lys Ala
                165                 170                 175

Arg Thr Asp Leu
            180

<210> SEQ ID NO 9
<211> LENGTH: 168
<212> TYPE: PRT
<213> ORGANISM: Caenorhabditis elegans

<400> SEQUENCE: 9

Met Ser Arg Leu Val Leu Leu Ile Ser Leu Val Ile Val Val Ala Ser
1               5                   10                  15

Ala Ala Ala Pro Gln Cys Glu Val Cys Lys Lys Val Leu Asp Asp Val
            20                  25                  30

Met Ala Lys Val Pro Ala Gly Asp Lys Ser Lys Pro Asp Ala Ile Gly
        35                  40                  45

Lys Val Ile Arg Glu His Cys Glu Thr Thr Arg Asn Lys Glu Asn Lys
50                  55                  60

Phe Cys Phe Tyr Ile Gly Ala Leu Pro Glu Ser Ala Thr Ser Ile Met
65                  70                  75                  80

Asn Glu Val Thr Lys Pro Leu Ser Trp Ser Met Pro Thr Glu Lys Val
                85                  90                  95
```

Cys Leu Glu Lys Leu Lys Gly Lys Asp Ala Gln Ile Cys Glu Leu Lys
            100                 105                 110

Tyr Asp Lys Pro Leu Asp Trp Lys Thr Ile Asp Leu Lys Lys Met Arg
        115                 120                 125

Val Lys Glu Leu Lys Asn Ile Leu Gly Glu Trp Gly Glu Val Cys Lys
    130                 135                 140

Gly Cys Thr Glu Lys Ala Glu Leu Ile Lys Arg Ile Gly Glu Leu Lys
145                 150                 155                 160

Pro Lys Tyr Val Lys Glu Glu Leu
                165

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
accatgtggg ccacgcaggg gct                                          23

<210> SEQ ID NO 11
<211> LENGTH: 23
<212> TYPE: DNA
<213> ORGANISM: Artificial Sequence
<220> FEATURE:
<223> OTHER INFORMATION: Synthetic primer

<400> SEQUENCE: 11
caaatcggtc ggtgcactgg ctg                                          23

<210> SEQ ID NO 12
<211> LENGTH: 23
<212> TYPE: DNA
<213> ORGANISM: Artificial Sequence
<220> FEATURE:
<223> OTHER INFORMATION: Synthetic primer

<400> SEQUENCE: 12
accatgtggg ctacgcgcgg gct                                          23

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
cagatcagtc cgtgcgctgg ctg                                          23

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: Xaa can be any naturally occurring amino acid

```
<220> FEATURE:
<221> NAME/KEY: misc_feature
<222> LOCATION: (9)..(9)
<223> OTHER INFORMATION: Xaa can be any naturally occurring amino acid

<400> SEQUENCE: 14

Leu Arg Pro Gly Asp Xaa Glu Val Xaa Ile
1               5                   10
```

NEUROTROPHIC FACTOR MANF AND USES THEREOF

This Nonprovisional application claims priority under 35 U.S.C. §119(e) on U.S. Provisional Application No. 61/052,757 filed on May 13, 2008, and under 35 U.S.C. 119(a) to Patent Application No. 20080326 filed in Finland on Apr. 30, 2008, all of which are hereby expressly incorporated by reference into the present application.

FIELD OF THE INVENTION

The present invention generally relates to the field of treatment of neuronal disorders and more particularly to growth factors for neural cells, especially for dopaminergic neurons at the CNS (central nervous system) and growth factor genes. The present invention also relates to the fields of gene delivery vectors and gene therapy.

BACKGROUND OF THE INVENTION

The mesencephalic astrocyte-derived neurotrophic factor (MANF) has been described as a survival factor for dopaminergic neurons in vitro (Petrova et al., 2003; WO 01/19851; and WO 02/074956), but its expression in mammalian tissues is poorly known. We recently characterized a homologous protein, the conserved dopamine neurotrophic factor (CDNF), which protects and rescues dopaminergic neurons in vivo (Lindholm et al., 2007; WO 2007/068784; and WO 2007/068803). MANF and CDNF proteins form a novel evolutionary conserved family of neurotrophic factors.

Neurotrophic factors are secreted proteins that promote neuronal survival and enhance formation and maintenance of neuronal connections in the vertebrate nervous system (Huang and Reichardt, 2001; Airaksinen and Saarma, 2002). The role of neurotrophic factors is well characterized mainly in the peripheral nervous system (PNS). In recent years, substantial knowledge has accumulated also about the involvement of growth factors in regulating the development and maintenance of neuronal populations in the central nervous system (CNS).

The characteristic motor symptoms of Parkinson's disease (PD) result from gradual degeneration of midbrain dopaminergic neurons. Several growth factors can act as survival factors for dopaminergic neurons (Krieglstein, 2004; Bespalov and Saarma, 2007), but their roles in the development and maintenance of these neurons in vivo are still unknown. Glial cell line-derived neurotrophic factor (GDNF; Lin et al., 1993) protects and even repairs the dopaminergic system in rodent and primate models of PD (Hoffer et al., 1994; Sauer et al., 1995; Kearns and Gash, 1995; Tomac et al., 1995; Gash et al., 1996; Grondin et al., 2002). However, results from clinical trials with GDNF on Parkinsonian patients have been controversial, since either clinical improvement (Gill et al., 2003; Patel et al., 2005) or low clinical efficacy (Lang et al., 2006) has been reported. Therefore, identification and characterization of new factors which could be neuroprotective and support functional neurorestoration is highly warranted.

Ischemic and epileptic insults, which are associated with neuronal death, trigger changes in the expression of several neurotrophic factors in the brain such as the GDNF family (Kokaia et al., 1999; Arvidsson et al., 2001) and the neurotrophins, e.g., BDNF (Emfors et al., 1991; Lindvall et al., 1992). Changes in neurotrophic factor levels following brain insults may regulate cell survival, synaptic plasticity, epileptogenesis, and neurogenesis from endogenous neural stem cells (Binder et al., 2001; Gustafsson et al., 2003; Jin et al., 2003; Kuipers and Bramham, 2006; Schäbitz et al., 2007). Therefore, modulation of neurotrophic factor levels could become of therapeutic value in ischemic and epileptic conditions.

A novel neurotrophic factor mesencephalic-astrocyte-derived neurotrophic factor (MANF; also known as arginine-rich, mutated in early stage of tumors; ARMET) was described few years ago as a survival-promoting factor for embryonic midbrain dopaminergic neurons in vitro (Petrova et al., 2003). The observed survival promoting effect of MANF was specific for dopaminergic neurons, and no effects on serotonergic or GABAergic neurons were detected (Petrova et al., 2003). Our group has recently characterized a vertebrate-specific paralog of MANF, named the conserved dopamine neurotophic factor (CDNF). CDNF (ARMET-like1) protects and rescues midbrain dopaminergic neurons in vivo in a rat 6-OHDA model of Parkinson's disease (Lindholm et al., 2007). MANF and CDNF proteins form a new family of evolutionarily conserved factors (Lindholm et al., 2007). Importantly, the effects of MANF and CDNF on dopaminergic neurons suggest that these factors could be used in treatment of neurodegerative disorders (Petrova et al., 2003, Lindholm et al., 2007). However, in vivo data of MANF are still lacking. Moreover, it should be noted that based on EST and genomic sequences of MANF we concluded that in contrast to the sequence reported by Petrova et al. (2003), WO 01/19851 and WO 02/074956, the amino acid 176 of human MANF is arginine (R) instead of proline (P), In this light, it seems that the some of the previous works related to MANF have been made with a MANF polypeptide having an amino acid substitution at position 176, and results of these experiments are thus not relevant to the present invention (see also Example 9).

In this invention, we characterized the distribution of Manf mRNA and protein in developing and adult brain and in non-neuronal tissues. We also discovered the effect of MANF in pathological conditions, such as Parkinson's disease, status epilepticus and global forebrain ischemia (i.e. stroke).

SUMMARY OF THE INVENTION

The present invention is related to a neurotrophic factor protein, MANF and a genetic sequence encoding the same. The MANF molecules, i.e. MANF nucleic acids and MANF polypeptides, will be useful in the development of a range of therapeutics and diagnostics useful in the treatment, prophylaxis and/or diagnosis of MANF dependent conditions. The molecules of the present invention are also useful effectors of primary and central neurons.

The isolated or recombinant MANF polypeptide of the present invention may be naturally glycosylated or may comprise an altered glycosylation pattern depending on the cells from which it is isolated or synthesised. For example, if produced by recombinant means in prokaryotic organisms, the molecule would be non-glycosylated. The molecule may be a full length, naturally occurring form or may be a truncated or otherwise derivatised form. Particularly important MANF polypeptides are the full-length human MANF with a signal peptide having the total length of 179 amino acids and the mature human MANF without the signal peptide having the total length of 158 amino acids.

Also disclosed are optionally formulated MANF polypeptide pharmaceutical compositions. Polypeptide compositions of the present invention may further comprise an acceptable carrier, such as a hydrophilic, e.g., pharmaceutically acceptable, carrier. Such compositions are useful in treating MANF dependent conditions.

The invention also includes a kit and reagents for diagnosing a MANF-dependent disorder in a mammal. The kit comprises a reagent which detects the presence or absence of a mutation in the nucleic acid sequence encoding MANF, elevated or diminished levels of MANF polypeptide and/or MANF antibody. The presence of the mutation or abnormal levels of MANF is an indication that the mammal is afflicted with the MANF-dependant disorder. The kit further comprises an applicator and an instructional material for the use thereof.

In addition to the above, the invention provides isolated nucleic acid molecules, expression vectors and host cells encoding MANF which can be used in the recombinant production of MANF as described herein. The isolated nucleic acid molecules and vectors are also useful to prepare transgenic animals and for gene therapy applications to treat patients with MANF related defects.

The MANF molecules of the present invention will be useful in the development of a range of therapeutic and/or diagnostic applications alone or in combination with other molecules such as CDNF or GDNF. The present invention extends, therefore, to pharmaceutical compositions comprising the MANF molecule or parts, fragments, derivatives, homologues or analogues thereof together with one or more pharmaceutically acceptable carriers and/or diluents. Furthermore, the present invention extends to vectors comprising the nucleic acid sequence set forth in SEQ ID NO:1 or having at least about 15%, more preferably about 40%, even more preferably around 60-79% or even still more preferably around 80-95% similarity thereto and host cells comprising the same. The MANF nucleic acid encoding mature MANF polypeptide without a signal peptide may be combined with a nucleic acid encoding another signal peptide to provide a full-length MANF polypeptide with a different signal peptide than the native MANF signal peptide.

In another embodiment the present invention is a transgenic non-human animal having a disrupted MANF gene or a transgenic non-human animal expressing an exogenous polynucleotide having at least 80% sequence identity to the sequence SEQ ID NO:2 or SEQ ID NO:4, or a complement of said polynucleotide.

In another embodiment the present invention can be used for a method of treating various pathologies, including neurological diseases such as Parkinson's disease, Alzheimers disease, epilepsy and global forebrain ischemia (i.e. stroke).

Although methods and materials similar or equivalent to those described herein can be used in the practice or testing of the present invention, suitable methods and materials are described below. The materials, methods, and examples are illustrative only and not intended to be limiting.

MANF antibody was visualized with peroxidase reaction resulting in brown color. Brain sections were counterstained with cresyl violet. A, Low-magnification image of retrosplenial cortex (RSCTX). MANF-positive cells were detected in layers II-VI. B, C, MANF antibodies specifically recognize MANF protein in immunohistochemistry. B, MANF protein in cerebral cortex (CTX; layer III). C, MANF antibodies pre-incubated with MANF protein did not bind to cortical cells. D, MANF labelling in the CA3 region of hippocampus; E, polymorphic layer of dentate gyrus (PoDG); F, caudate putamen (striatum; CPu); and G, substantia nigra pars reticulata (SNr). H, Low-magnification image showing MANF staining in the substantia nigra. Substantia nigra pars compacta (SNc). I, MANF protein in the Purkinje cells of cerebellum (Pkj); J, spinal cord (SpC); K, choroid plexus (ChP); L, salivary gland (SG). A, Dark-field microphotograph showing Manf mRNA expression in seminiferous tubules (ST) by in situ hybridization. N, MANF protein in seminiferous tubules. B, C, and F cryosections; A, D, E, G and H—N paraffin sections. Scale bar 100 µm in (A-G) and (1-N); 200 µm in (H).

Figure 6:
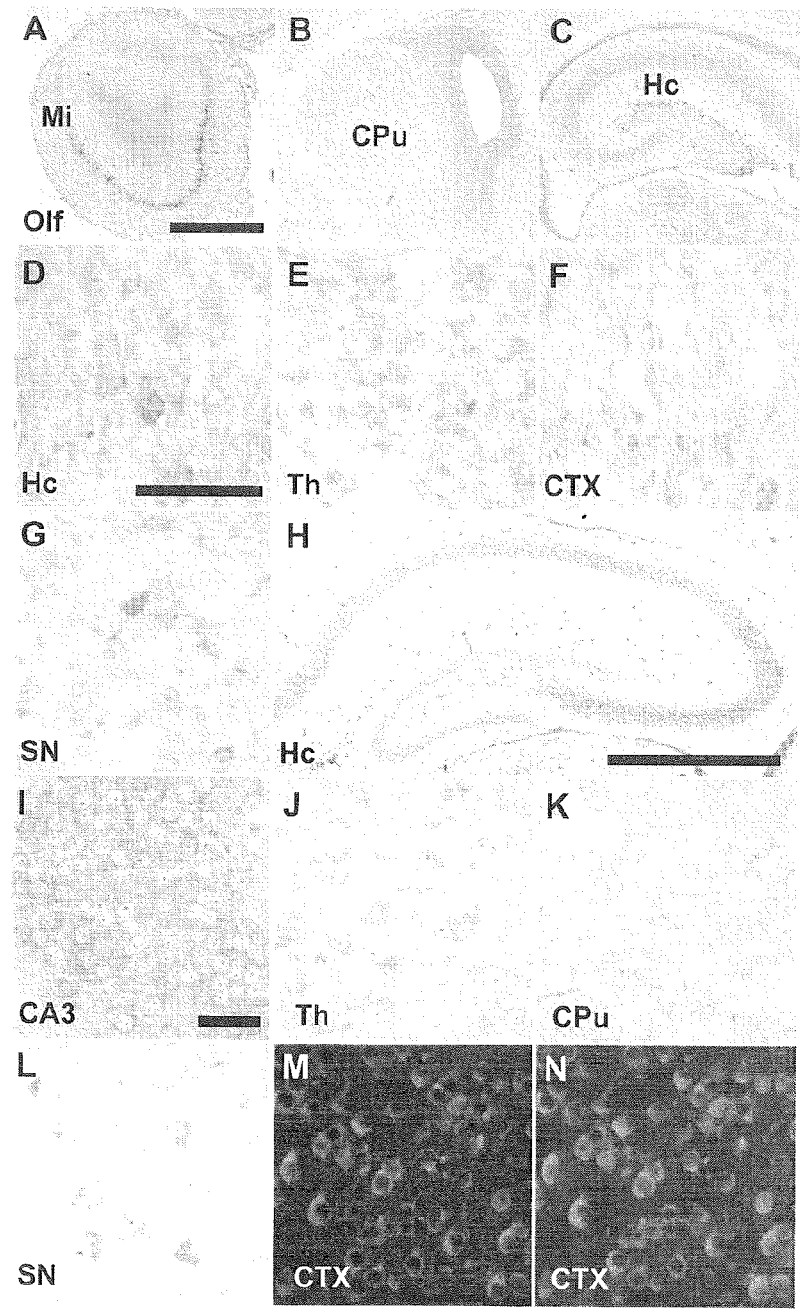

FIG. 6. Immunohistochemical localization of MANF protein in postnatal day 1 (P1; A-G) and P10 (H-N) mouse brain. A, Strong MANF signal was detected in the mitral cell layer (Mi) of olfactory bulb (Olf). B, MANF labelling in the caudate putamen (CPu); C, D, hippocampus (Hc); E, thalamus (Th); F, cerebral cortex (CTX); G, substantia nigra (SN) of P1 mouse brain. H, MANF labelling in the hippocampus of P10 mouse brain. I, MANF signal in cells of hippocampal CA3 region (CA3); J, thalamus; K, caudate putamen; L, substantia nigra of P10 mouse brain. M, N, MANF immunofluorescence signal (M; green) co-localized with NeuN neuronal marker (N, red) in the cells of cerebral cortex. Scale bar 500 µm in (A-C, H); 50 µm in (D-G and I-N).

Figure 7:
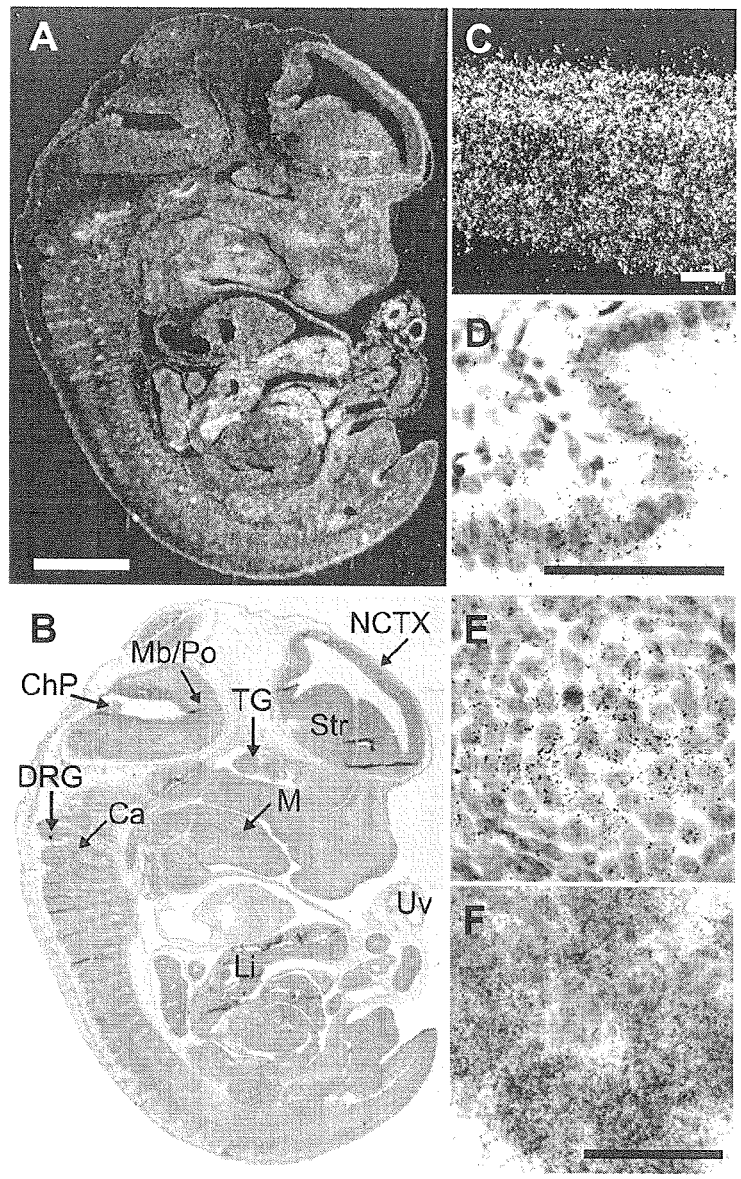

FIG. 7. In situ hybridization analysis of Manf mRNA expression in embryonic mouse at E12.5 (A-E) and E17 (F). A, Dark-field emulsion autoradiograph of a sagittal section of E12.5 embryonic mouse. B, Corresponding bright-field image for (A) with indicated anatomical structures. C, Dark-field microphotograph showing Manf-signal in the roof of neopallial cortex. D, Bright-field microphotograph showing Manf-signal in the choroid plexus; and, E, cartilage primordium of vertebra. F, Manf-signal in salivary gland of E17 embryonic mouse. Ca, cartilage primordium of vertebra; ChP, choroid plexus; DRG, dorsal root ganglion; Li, liver; Mb/Po, midbrain/pons junction; NCTX, neopallial cortex; Str, striatum, TG, trigeminal ganglion, Uv, umbilical vessels. Scale bar 1 mm in (A, B), 50 µm in (C-F).

Figure 8:
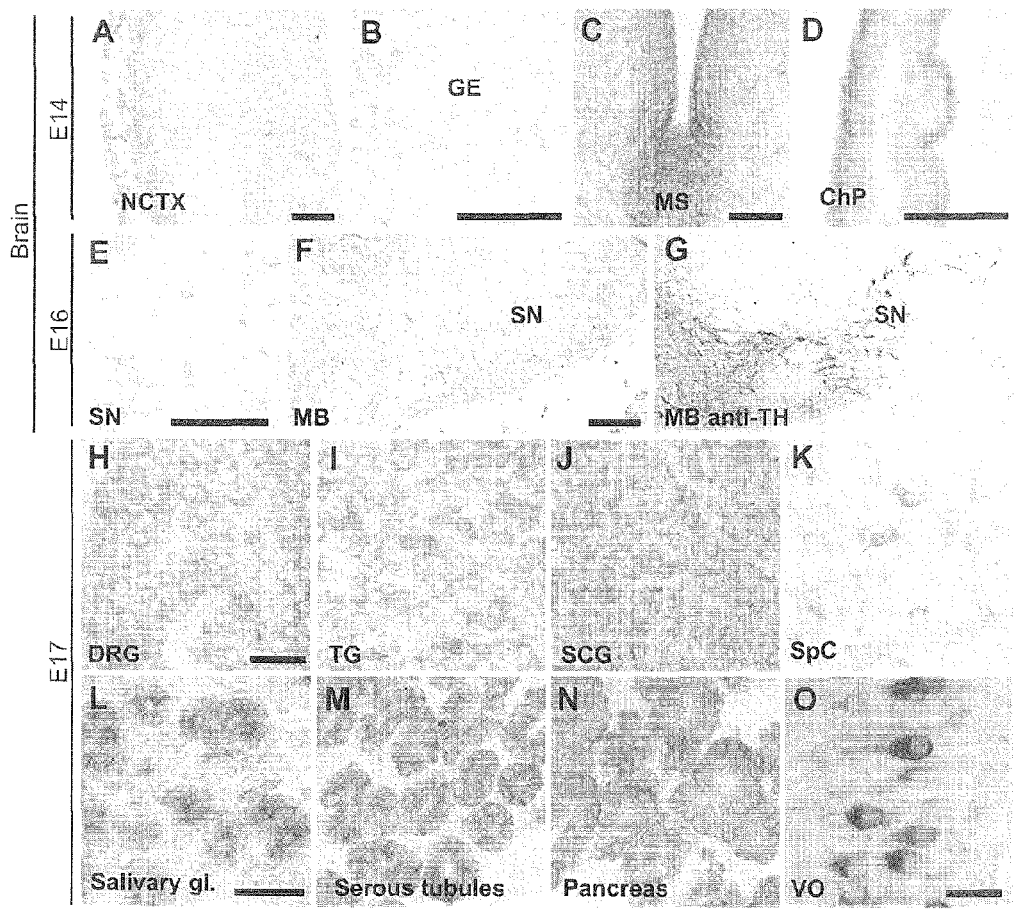

FIG. 8. Immunohistochemical analysis of MANF expression in embryonic day 14 (E14; A-D); E16 (E-G) or E17 (H-O) mouse tissues. A, MANF signal in the neopallial cortex (NCTX; future cerebral cortex); B, striatum (ganglionic eminence; GE); C, median sulcus (MS); D, choroid plexus (ChP). E, F, MANF staining in developing substantia nigra (SN) in the midbrain (MB). G, Tyrosine hydroxylase (TH) staining in a section parallel of (F). H, MANF protein in the dorsal root ganglion (DRG); I, trigeminal ganglion (TG); J, superior cervical ganglion (SCG); K, spinal cord (SpC); L, salivary gland; M, tubules of serous glands located in nasal cavity; N, pancreas; O, cells in vomeronasal organ. A-G, coronal brain sections; H-M, O, transverse head sections; N, sagittal section of whole embryo. Scale bar 50 µm in A-E, H-N; 100 µm in F, G; 20 µm in O.

Figure 9:
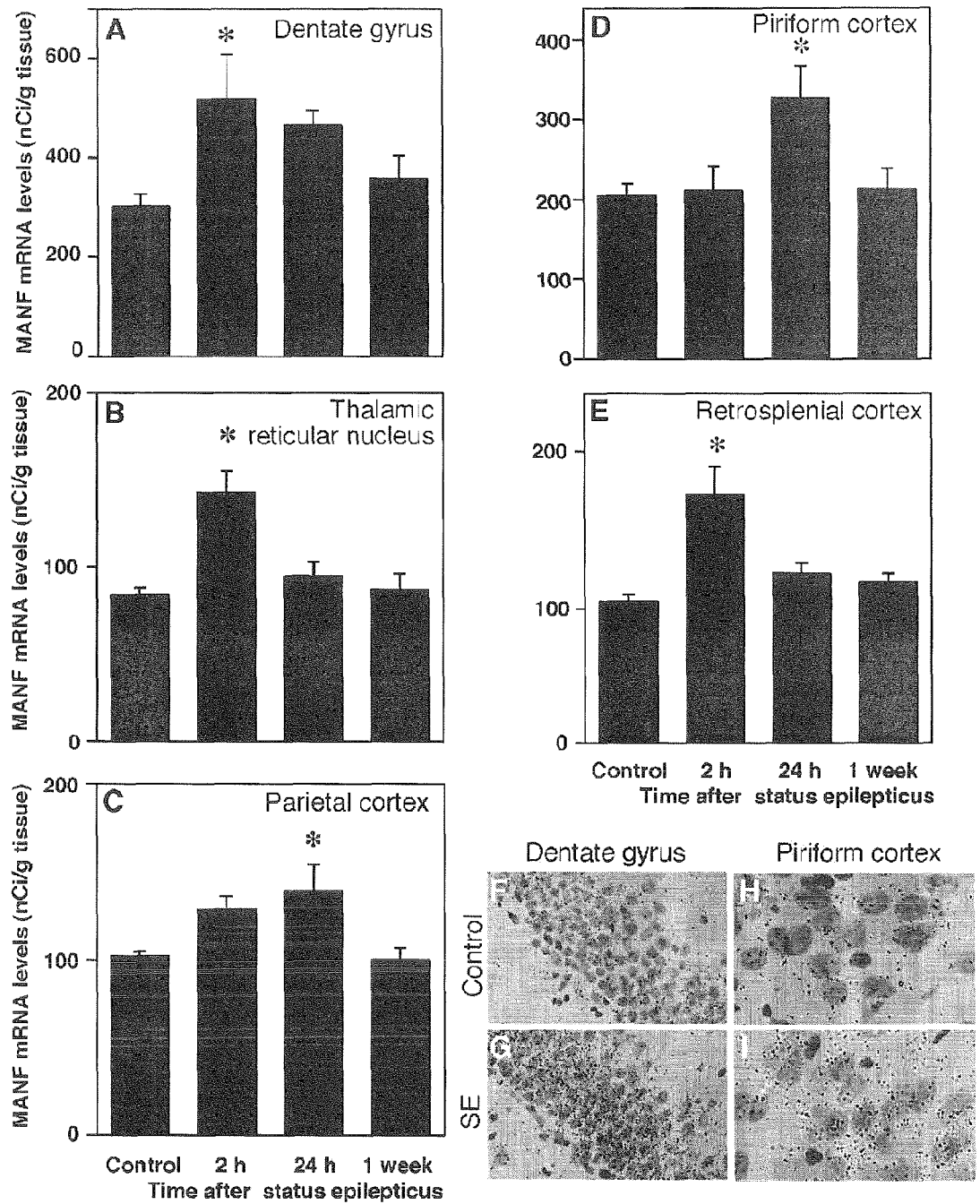

FIG. 9. A-E, Levels of Manf mRNA in the dentate gyrus granule cell layer (A), thalamic reticular nucleus (B), and parietal (C), piriform (D) and retrosplenial (E) cortices at different time-points after status epilepticus, as measured by computerized image analysis of X-ray films. Data are expressed as means±S.E.M. *P<0.05 compared to control, one-way ANOVA followed by Dunnett's post hoc test, F-I, Bright-field photomicrographs of autoradiographic grains over cells stained with cresyl violet, illustrating dentate granule cells (F and G) and neurons in the piriform cortex (H and I) expressing Manf mRNA under control conditions (F and H) and at 2 h (G) or 24 h (I) after status epilepticus (SE).

Figure 10:
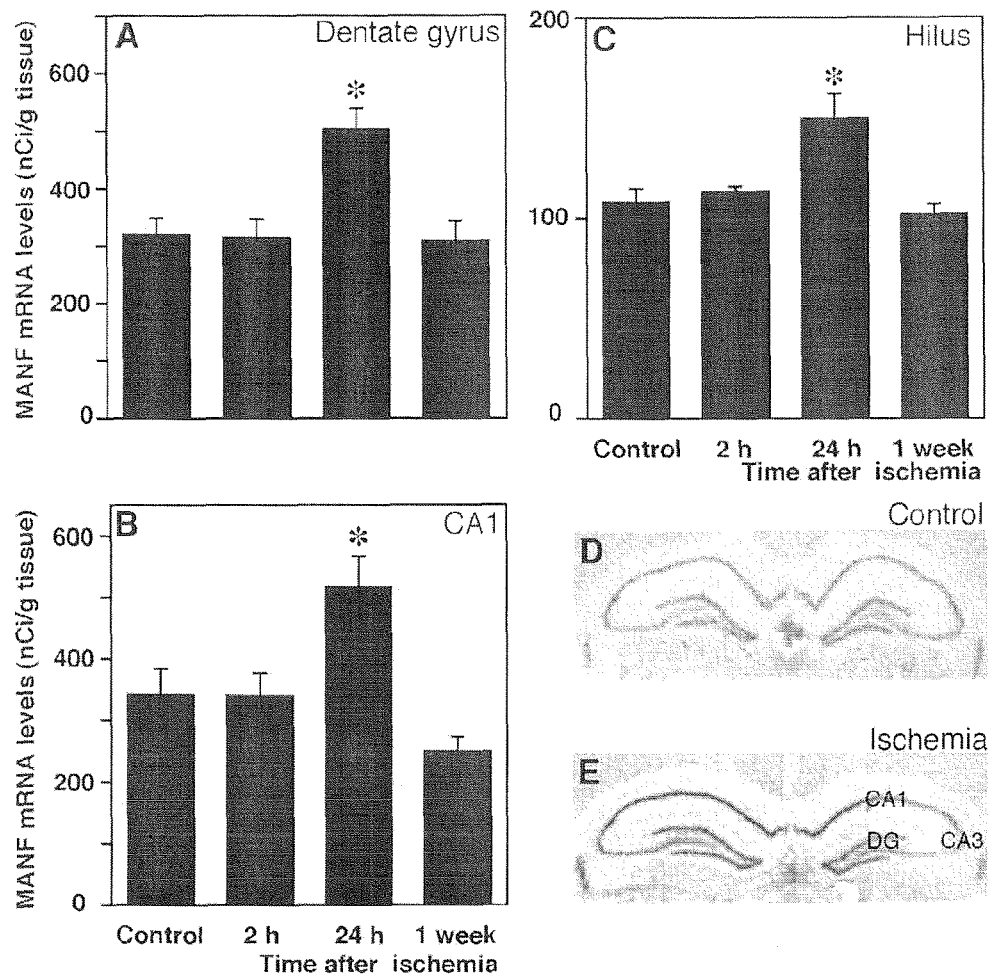

FIG. 10. A-C, Levels of Manf mRNA in the dentate gyrus granule cell layer (A), CA1 pyramidal cell layer (B) and dentate hilus (C) at different times of reperfusion after 10 min of global forebrain ischemia, as measured by computerized image analysis of X-ray films. Data are expressed as means±S.E.M. *P<0.05 compared to control, one-way ANOVA followed by Dunnett's post hoc test. (D, E) Bright-field photomicrographs of autoradiograms showing the pattern of Manf gene expression in the hippocampal formation under control conditions (D) and after 10 min of global forebrain ischemia followed by 24 h of reperfusion (E). DG, dentate gyrus.

Figure 11:
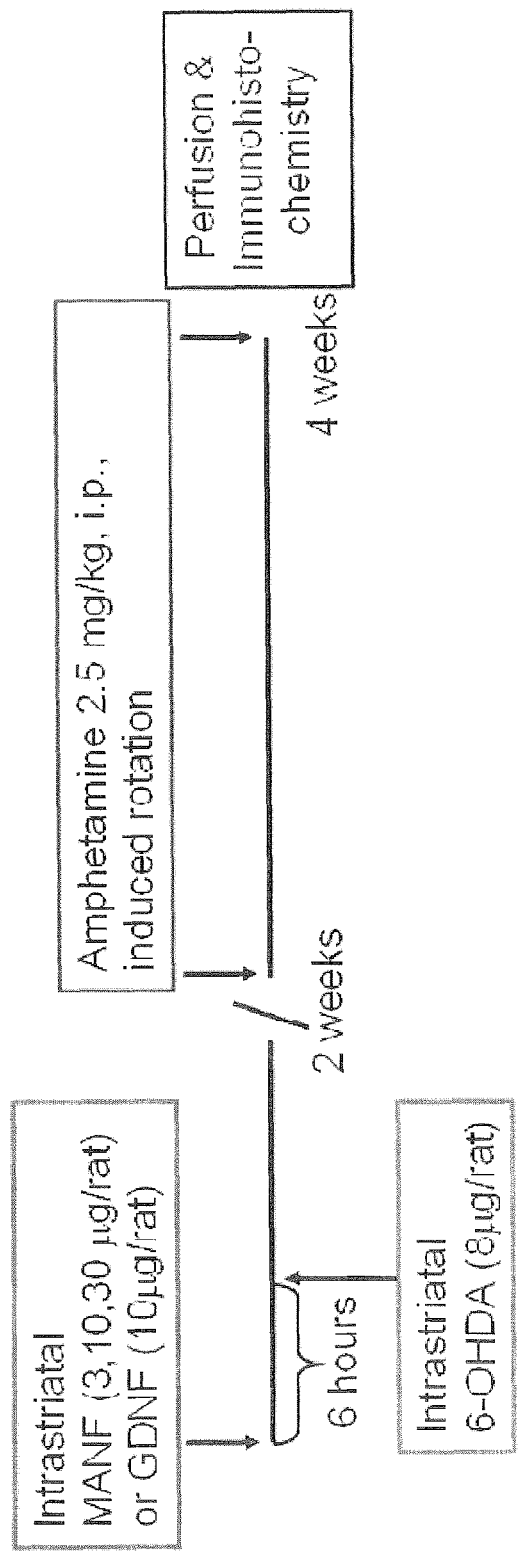

FIG. 11. Experimental plan for an experimental model of Parkinson's disease.

Figure 12:
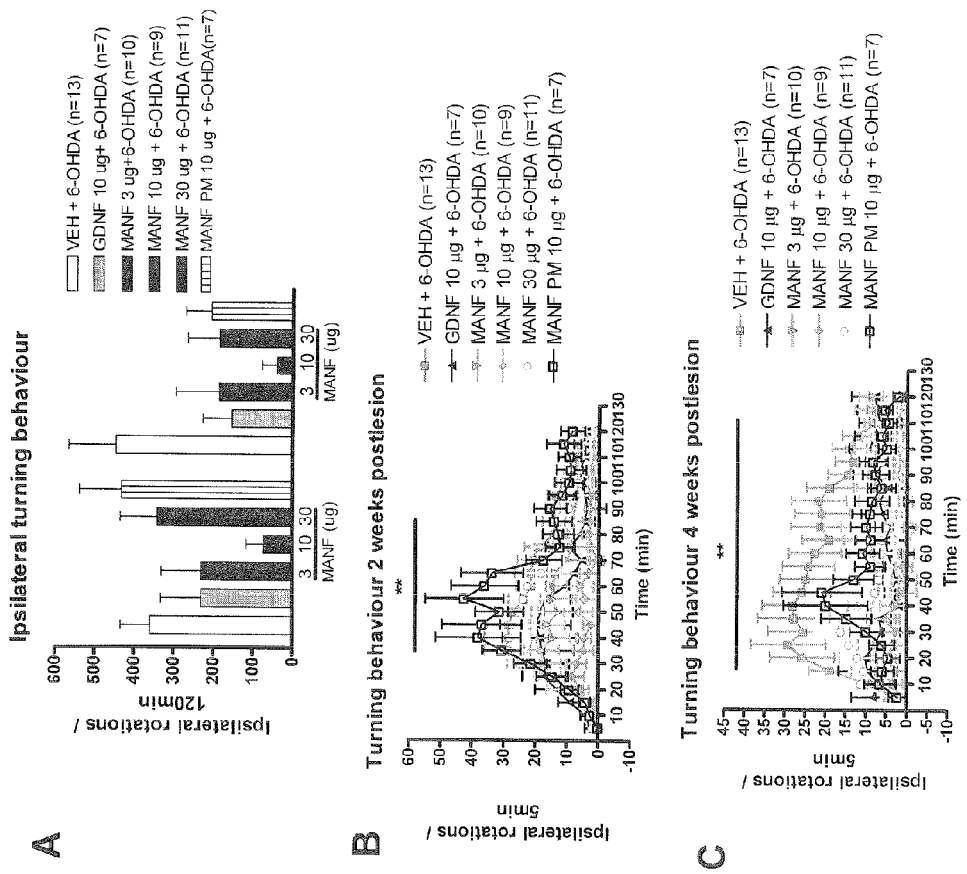

FIG. 12. MANF dose response studies. A. Ipsilateral turning behaviour; B. Turning behaviour 2 weeks post-lesion; C. Turning behaviour 4 weeks post-lesion.

Figure 13:
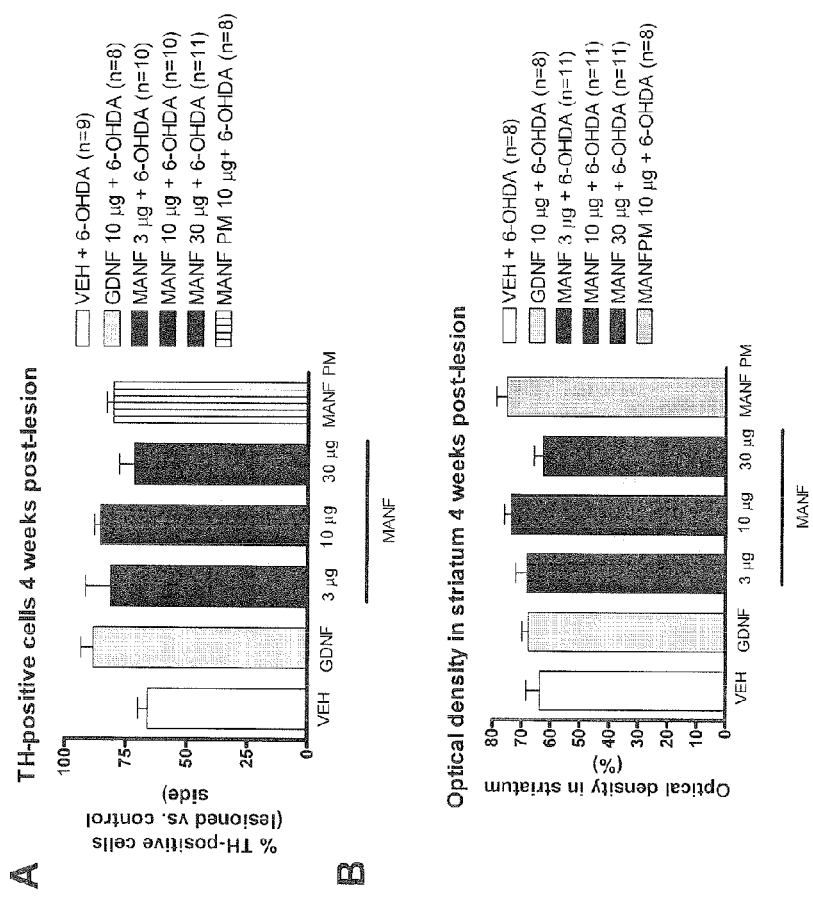

FIG. 13. MANF dose response studies. A.TH-positive cells 4 weeks post-lesion; B. Optical density in striatum 4 weeks post-lesion.

Figure 14:
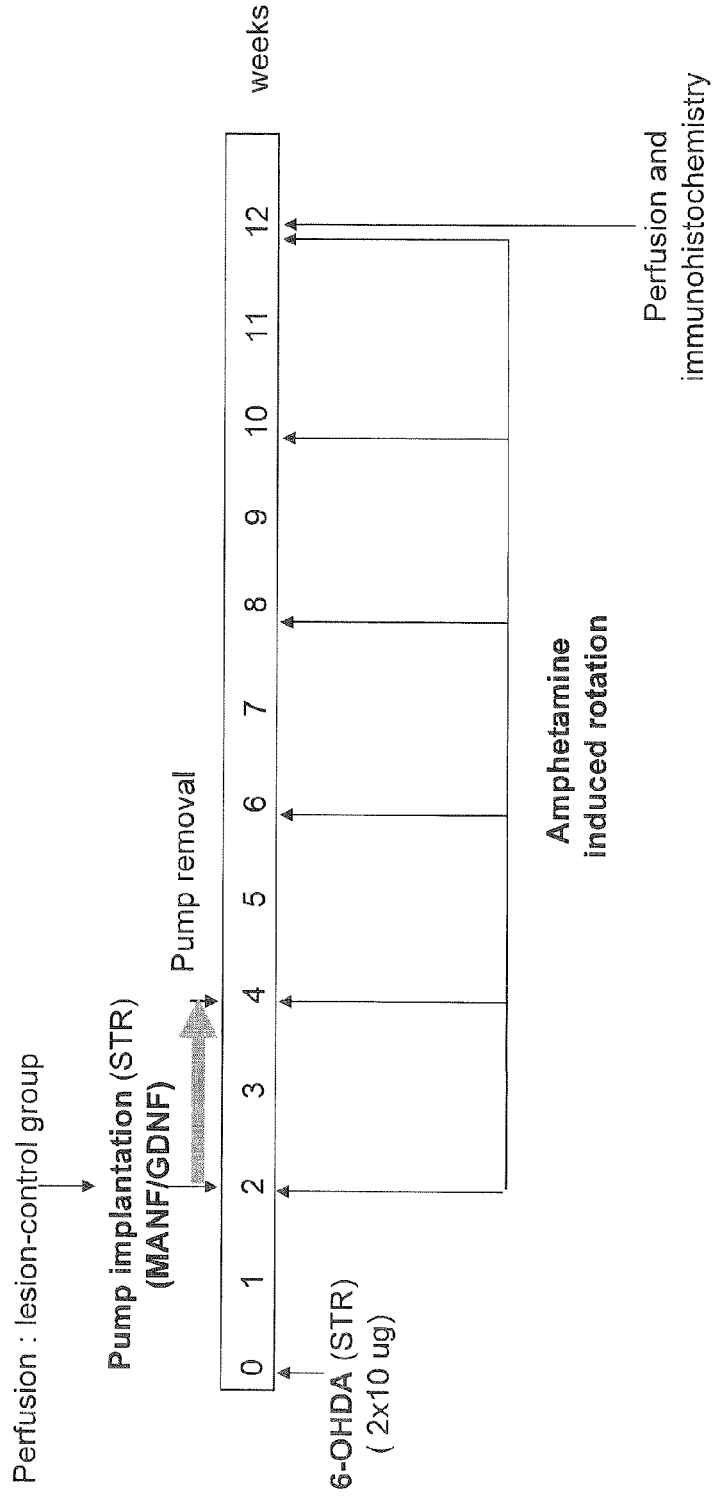

FIG. 14. The effect of chronic MANF infusion.

Figure 15:
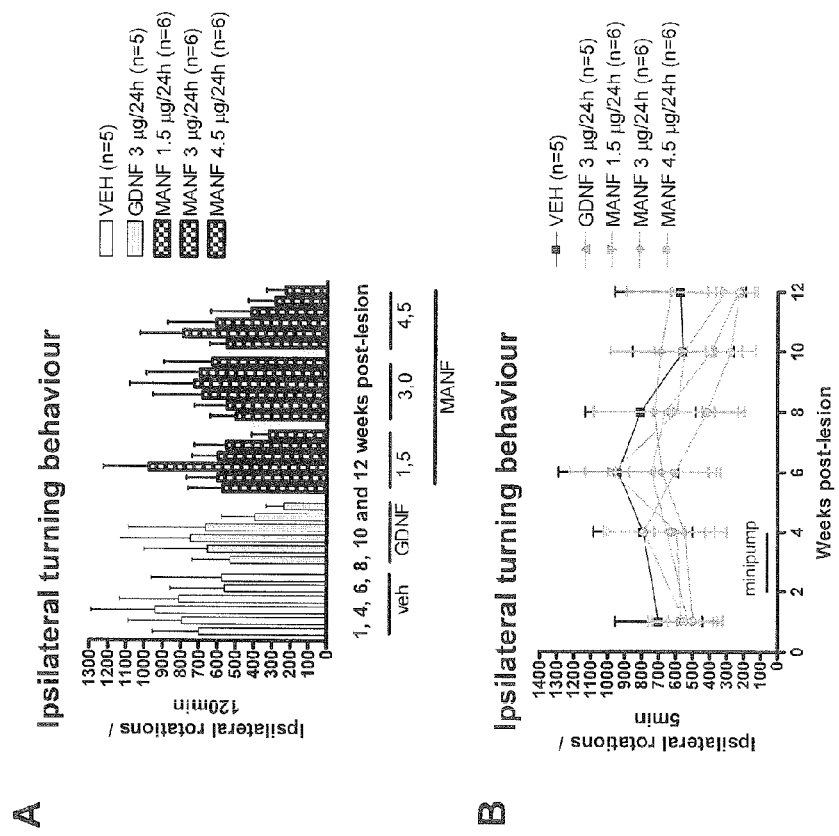

FIG. 15. The effect of chronic MANF infusion. A. Ipsilateral turning behaviour; B. Ipsilateral turning behaviour.

Figure 16:
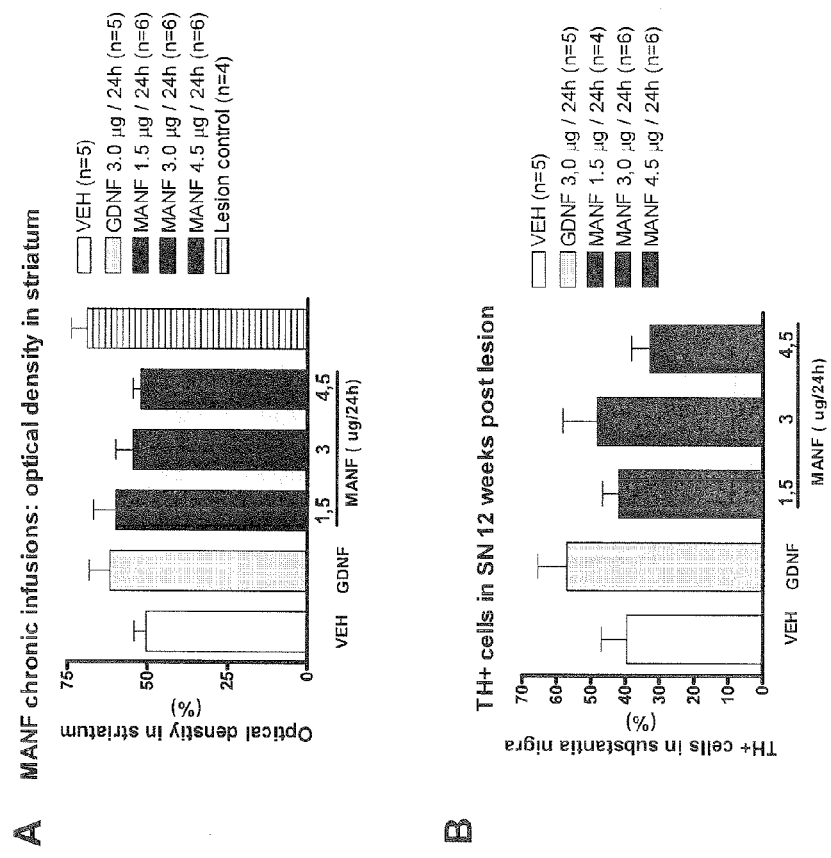

FIG. 16. The effect of chronic MANF infusion. A. MANF chronic infusions, optical density in striatum; B. TH-positive cells in SN 12 weeks post-lesion.

Figure 17:
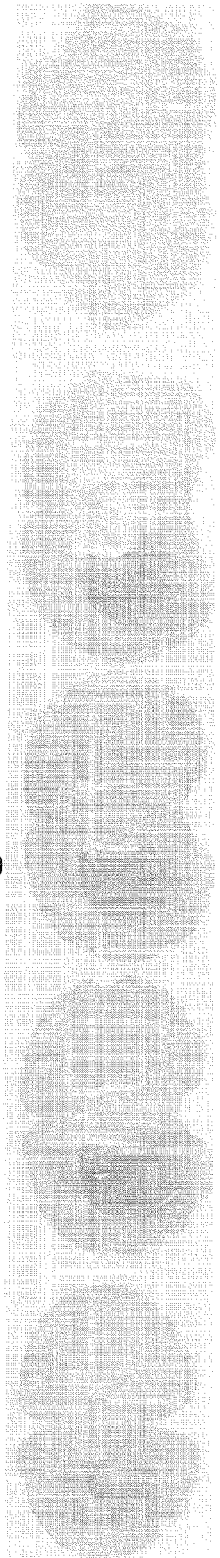
Figure 17:
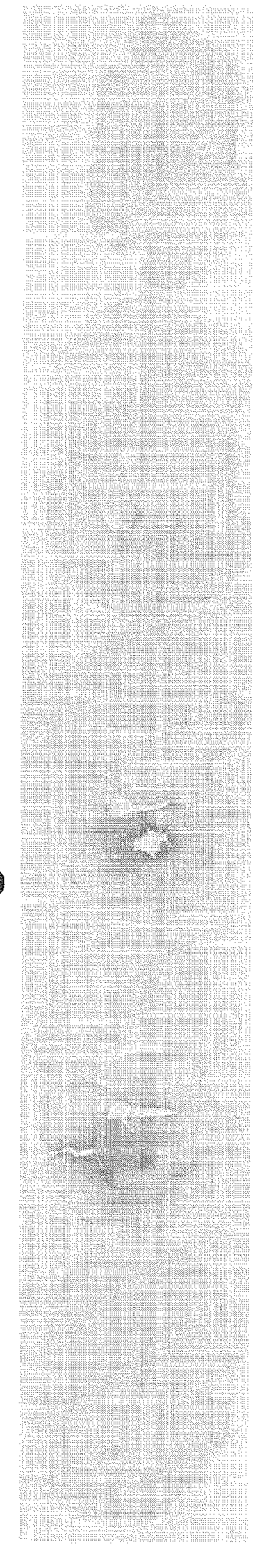

FIG. 17. MANF and GDNF immunohistochemistry.

Figure 18:
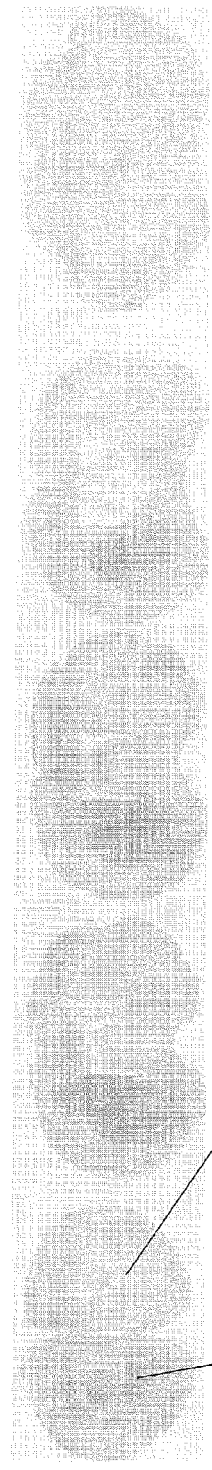
Figure 18:
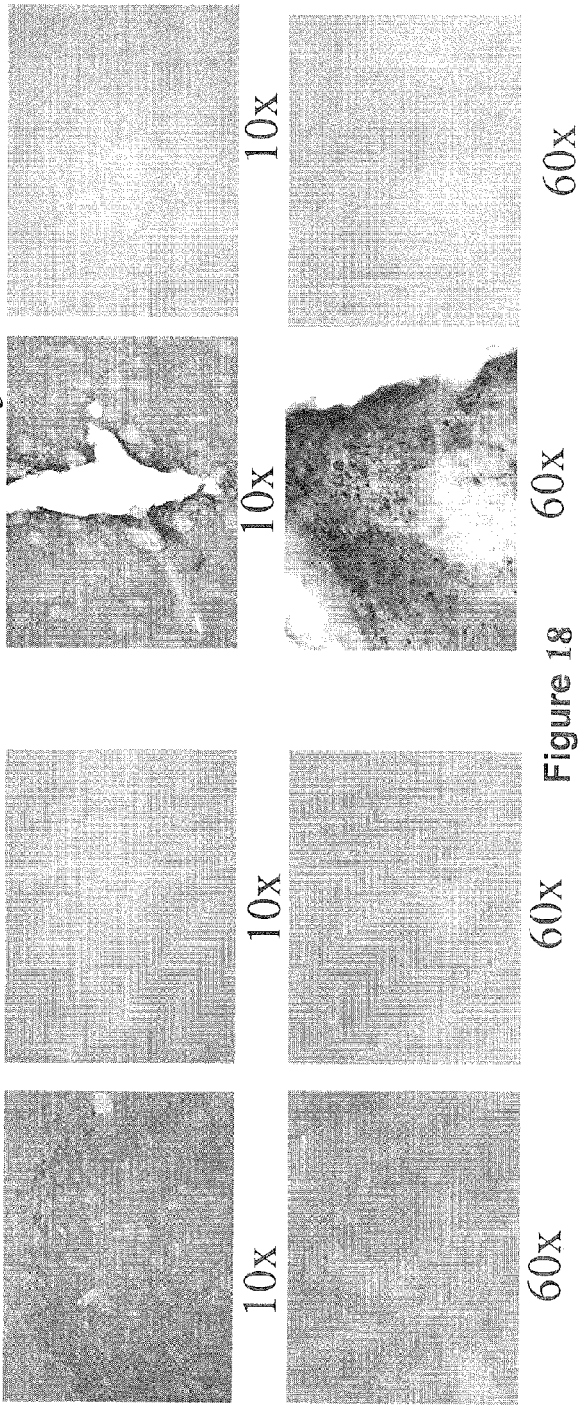

FIG. 18. Diffusion studies; Anti-MANF staining 24 h after intrastriatal MANF.

Figure 19:
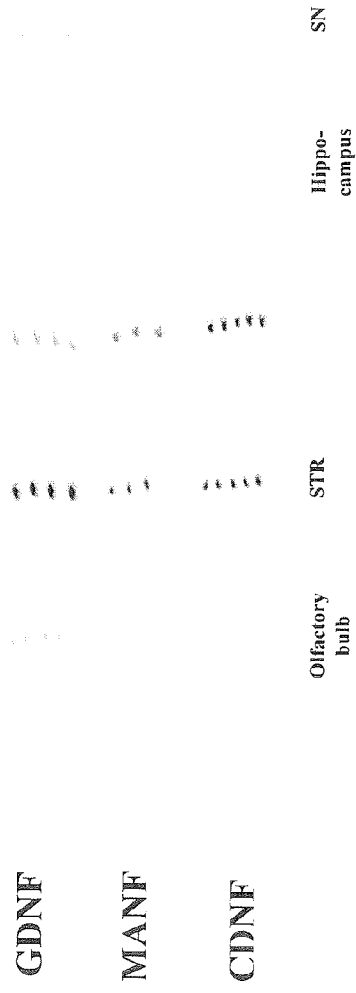

FIG. 19. Transportation experiments. Autoradiography.

Figure 20:
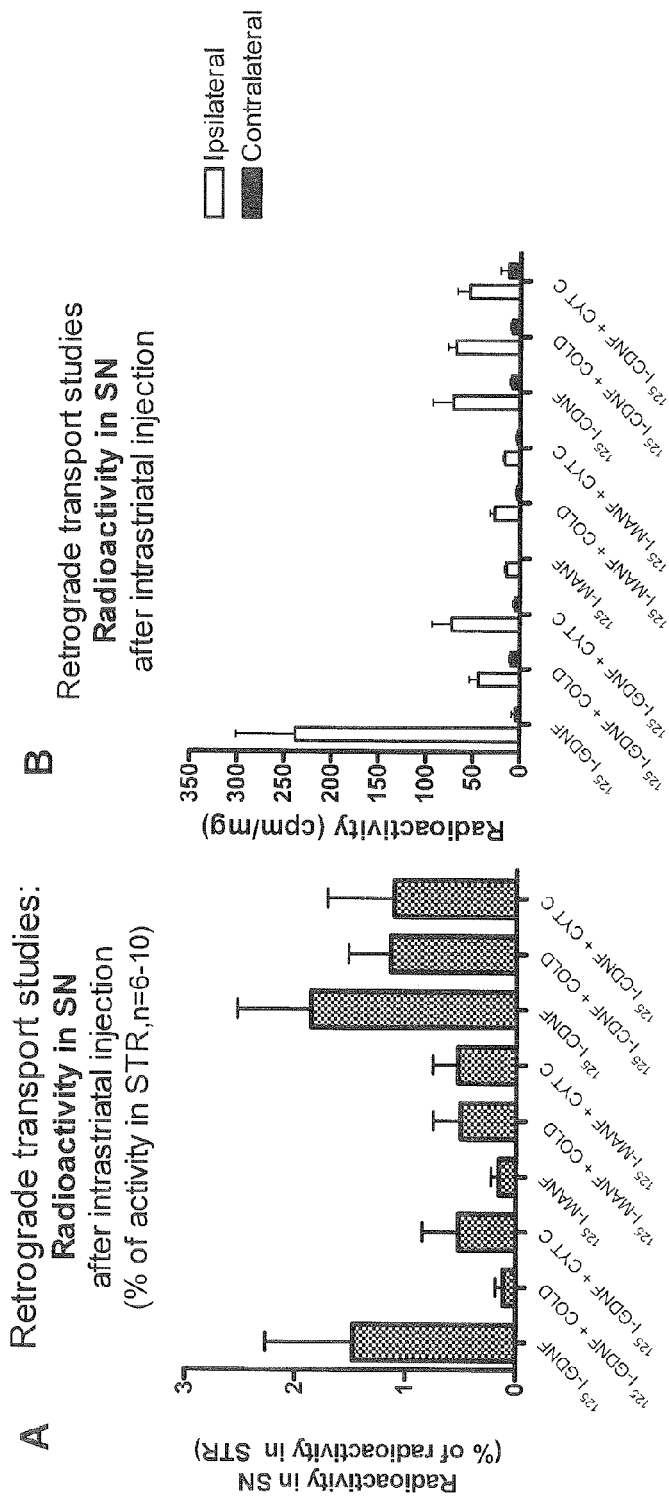

FIG. 20. A. Radioactivity after intrastriatal $^{125}$I MANF injection; B. Radioactivity in striatum.

Figure 21:
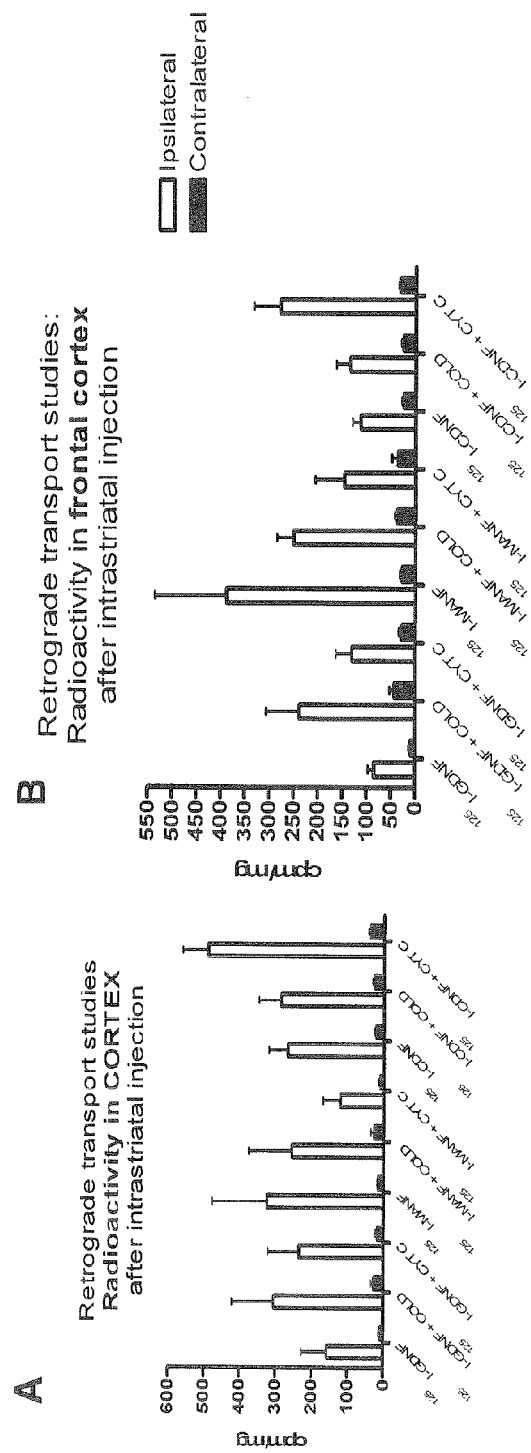

FIG. 21. A. Radioactivity in cortex; B. Radioactivity in frontal cortex.

Figure 22:
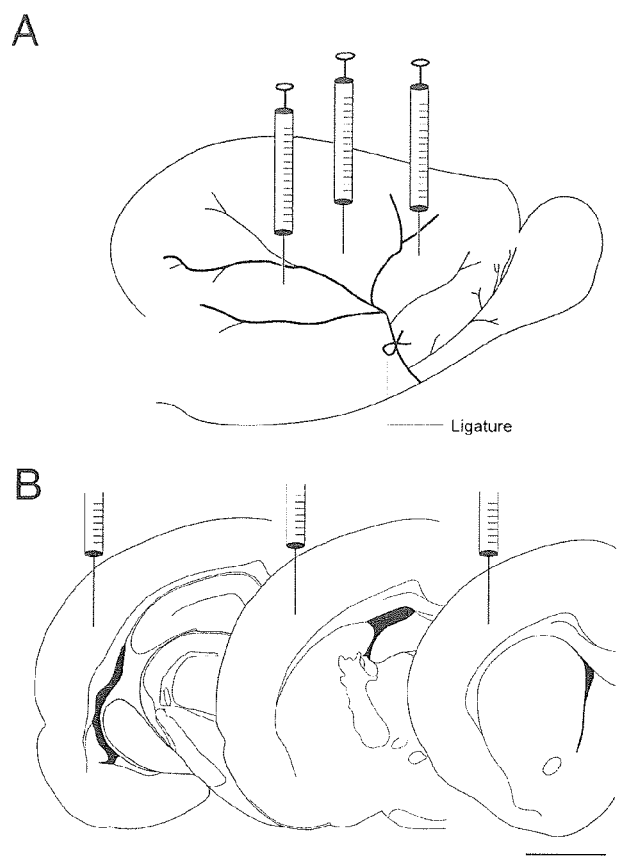

FIG. 22. Schematic diagram of the injection and ligation sites.

Figure 23:
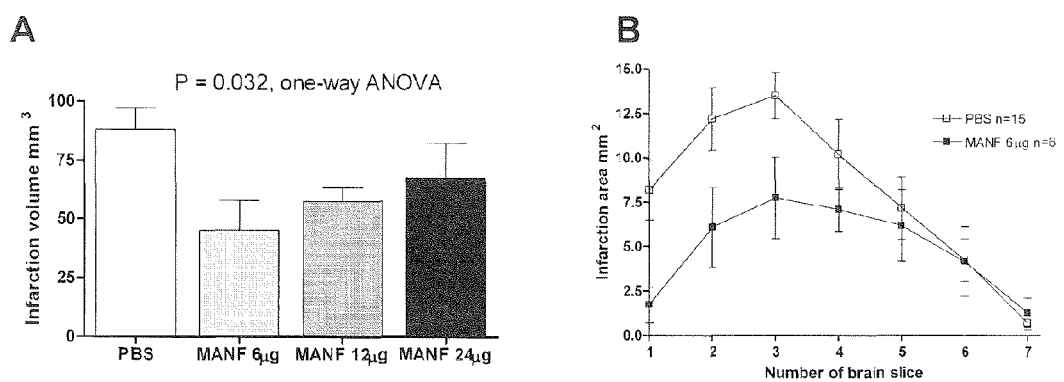

FIG. 23. Effect of local cortical MANF administration on infarction volume. A: Volume of infarction was significantly reduced in MANF-treated rats (P=0.032 treatment effect, one-way ANOVA). The infarction volume is measured form the first four brain slices starting from the rostral part of the brain; n=15 PBS; n=6 MANF 6 µg; n=8 MANF 12 µg, n=5 MANF 24 µg. B: In the right column are shown the effects of PBS and 6 µg MANF on infarction area per slice. The infarction area was significantly reduced in rats treated with 6 µg MANF as compared with PBS treatment (P=0.002 treatment effect, two-way ANOVA).

Figure 24:
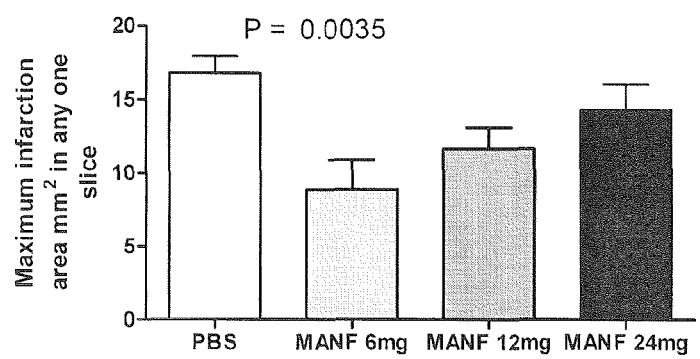

FIG. 24. Effect of local cortical MANF administration on maximal infarction area. Area of infarction was significantly reduced in MANF treated rats (P=0.0035 treatment effect, Kurskal-Wallis one-way analysis of variance on ranks).

Figure 25:
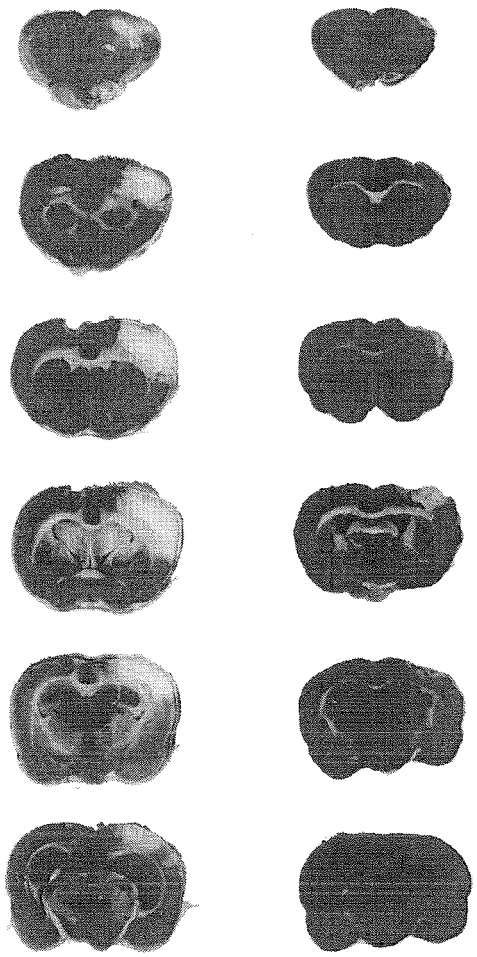

FIG. 25. Pretreatment with MANF reduces cortical infarction induced by MCA ligation and reperfusion. A, on the left PBS treated rat. B, on the left right rat treated with 6 µg MANF.

Figure 26:
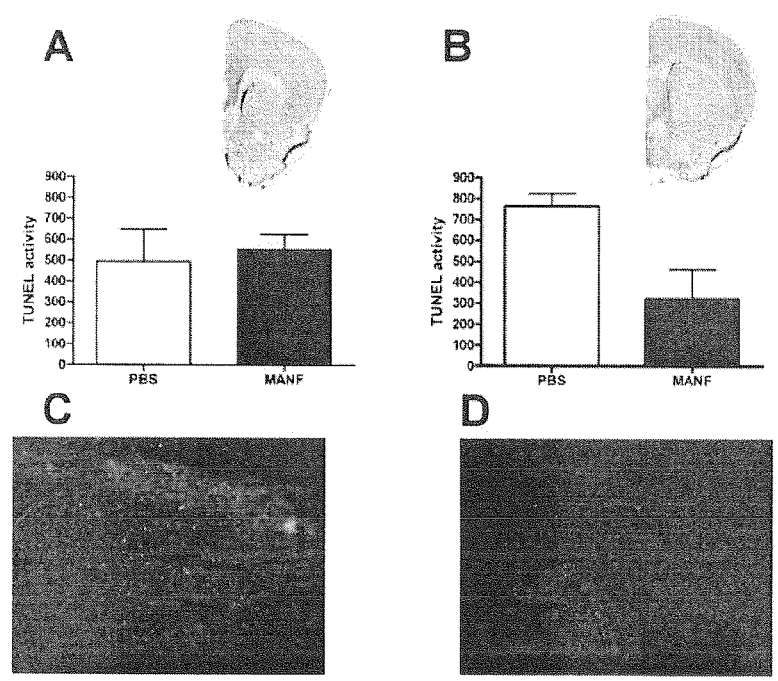

FIG. 26. Effect of local cortical MANF (2 µg/µl) on cortical TUNEL activity. A: shows the averages of TUNEL positive nuclei counted at level +2.2 mm from bregma B: shows the averages of TUNEL positive nuclei counted at levels −0.2-0.2 mm from bregma (n=3, P=0.0449, Student's t-test). Photomicrograps above the bar graphs show the representative level of sections counted. C: photomicrograph from cortical area of a rat treated with PBS. D: photomicrograph from cortical area of a rat treated with MANF. Six sections were counted from each rat.

Figure 27:
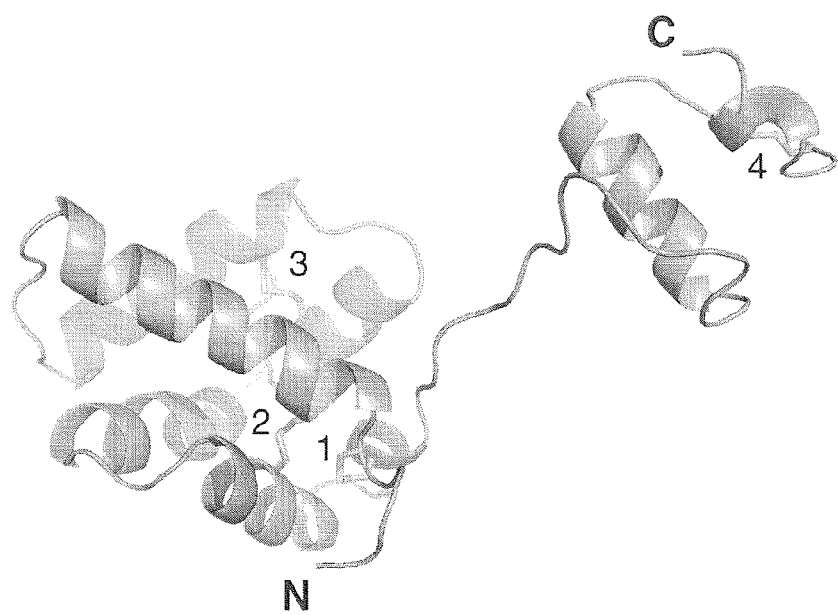

FIG. 27. A schematic ribbon diagram of the MANF structure. N- and C-terminus are labelled. Disulfide bridges are highlighted in yellow and numbered 1-4 from N- to C-terminus.

Figure 28:
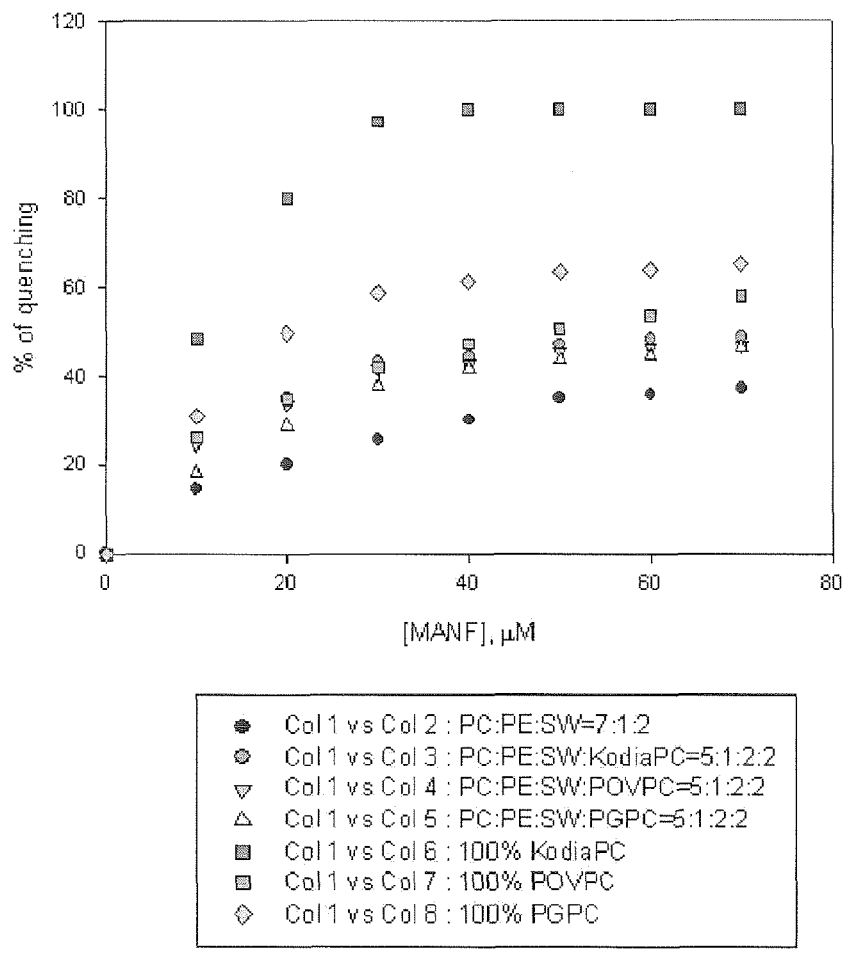

FIG. 28. MANF binding to selected lipids and their combinations measured by tryptophan fluorescence. KOdiAPC, 1-(Palmitoyl)-2-(5-keto-6-octene-dioyl)phosphatidylcholin; PC, phosphocholine; PE, phosphoethanolamine; PGPC, 1-Palmitoyl-2-Glutaroyl-sn-Glycero-3-Phosphocholine; POVPC, 1-Palmitoyl-2-(5'-oxo-Valeroyl)-sn-Glycero-3-Phosphocholine; SW, sphingomyelin.

Figure 29:
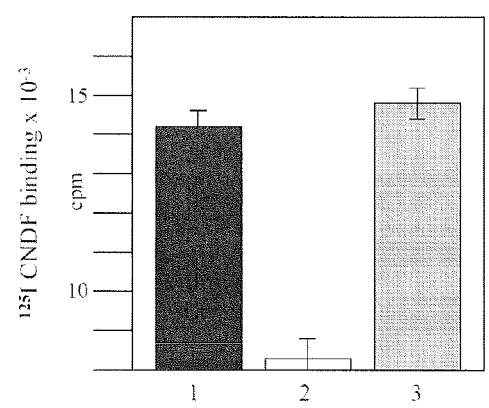

FIG. 29. $^{125}$I labeled CDNF (1) binds with high affinity to hippocampal and cortical neurons and this binding is displaced by 200 times molar excess of unlabelled CDNF (2), but not by 200 times molar excess of unlabelled MANF (3).

Figure 30:
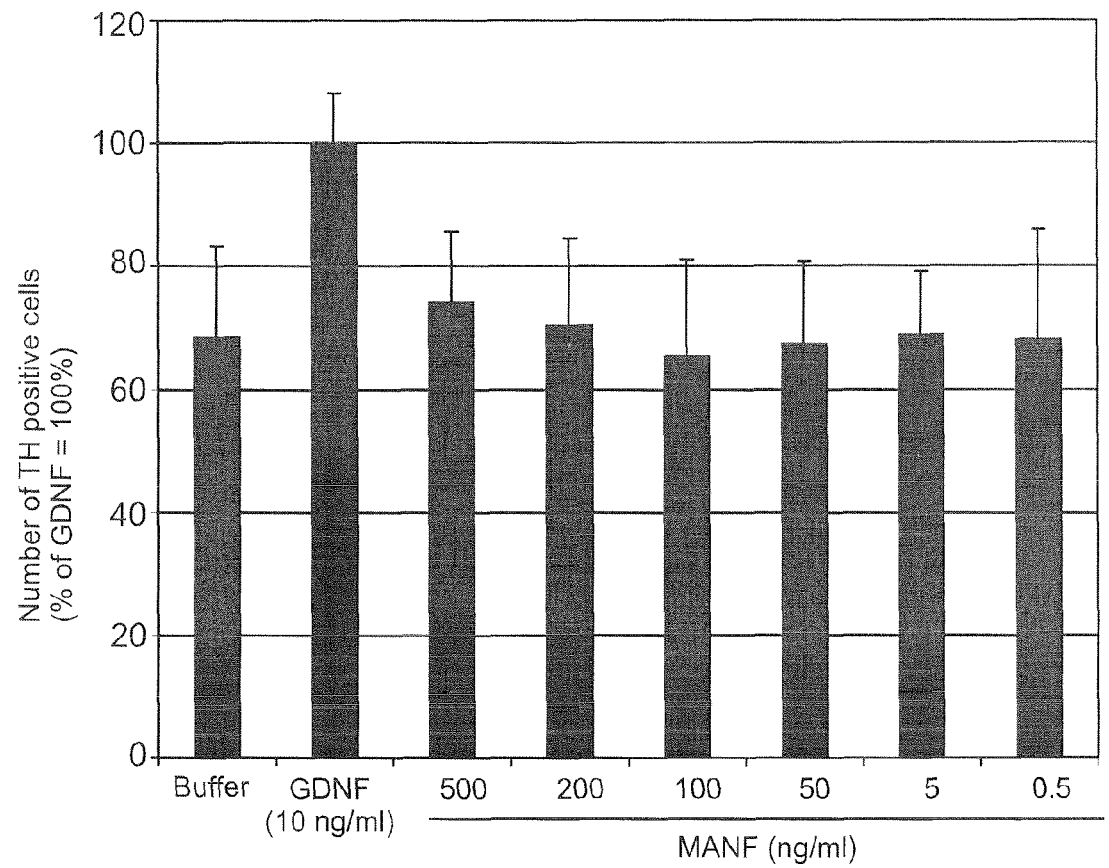

FIG. 30. Number of TH positive cells at DIV 5. Average nr of TH positive cells at GDNF treated wells set as 100%. Data piled from 3 independent experiments, $p<0.000001$ for GDNF (two tailed homoscedastic student's T-test) total nr of TH positive neurons analyzed per neurotrophic factor concentration 8000-16,000, error bars indicate SD. MANF had no statistically significant survival promoting effect at TH positive neurons at all concentration investigated.

Figure 31:
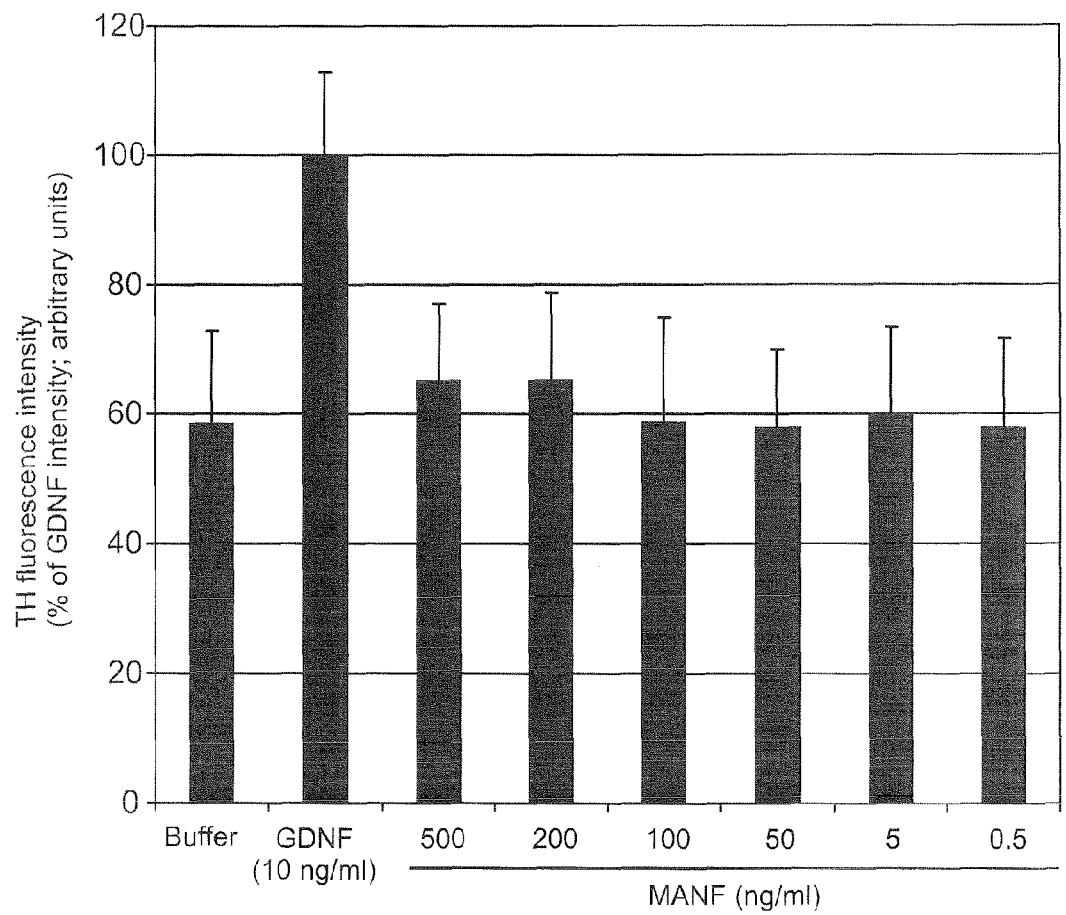

FIG. 31. TH fluorescence intensity at DIV 5.

Relative TH immunoflourescence intensity as measured from all microislands from all above 3 experiments. Average intensity of TH positive cells at GDNF treated wells set as 100%. $p<0.000001$ for GDNF (two tailed homoscedastic student's T-test), error bars indicate SD. MANF had no statistically significant effect at relative TH levels at all concentration investigated.

DETAILED DESCRIPTION OF THE INVENTION

In this invention we used in situ hybridization and immunohistochemistry to characterize MANF expression in developing and adult mouse. MANF expression was widespread in the nervous system and non-neuronal tissues. In the brain, relatively high Manf mRNA and protein levels were detected in the cerebral cortex, hippocampus and cerebellar Purkinje cells. After status epilepticus, Manf mRNA expression was transiently increased in the dentate granule cell layer hippocampus, thalamic reticular nucleus and in several cortical areas. In contrast, following global forebrain ischemia changes in Manf expression were widespread in the hippocampal formation and more restricted in cerebral cortex. The widespread expression of MANF together with its evolutionary conserved nature and regulation by brain insults suggest that it has important functions both under normal and pathological conditions in many tissue types.

It was also showed that MANF has a neuroprotective effect in rat stroke and PD models.

Unless defined otherwise, all technical and scientific terms have the same meaning as is commonly understood by one of skill in the art to which this invention belongs. The definitions below are presented for clarity.

"Isolated" when referred to a molecule, refers to a molecule that has been identified and separated and/or recovered from a component of its natural environment and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide sequences of the present invention.

As used herein, a "polynucleotide" refers to a molecule having a nucleic acid sequence encoding SEQ ID NO:1 or a fragment or variant thereof, a nucleic acid sequence contained in SEQ ID NO:3 or the complement thereof. For example, the polynucleotide can contain the nucleotide sequence of the full-length EDNA sequence, including the 5' and 3' untranslated sequences, the coding region, as well as fragments, epitopes, domains, and variants of the nucleic acid sequence. Moreover, as used herein, a "polypeptide" refers to a molecule having an amino acid sequence encoded by a polynucleotide of the invention as broadly defined. As used herein, the term "fragment" as applied to a nucleic acid, may ordinarily be at least about 10 nucleotides in length, typically, at least about 20 nucleotides, more typically, from about 20 to about 50 nucleotides, preferably at least about 50 to about 100 nucleotides, even more preferably at least about 100 nucleotides to about 300 nucleotides, yet even more preferably at least about 300 to about 400, and most preferably, the nucleic acid fragment will be greater than about 500 nucleotides in length.

As used herein, the term "fragment" as applied to a polypeptide, may ordinarily be at least about seven contiguous amino acids, typically, at least about fifteen contiguous amino acids, more typically, at least about thirty contiguous amino acids, typically at least about forty contiguous amino acids, preferably at least about fifty amino acids, even more preferably at least about sixty amino acids and most preferably, the peptide fragment will be greater than about seventy contiguous amino acids in length.

"Nucleic acid molecule", includes DNA molecules (e.g. cDNA or genomic DNA), RNA molecules (e.g., mRNA), analogs of the DNA or RNA generated using nucleotide analogs, and derivatives, fragments and homologs. The nucleic acid molecule may be single-stranded or double-stranded, but preferably comprises double-stranded DNA.

"Isolated nucleic acid molecule" is separated from other nucleic acid molecules which are present in the natural source of the nucleic acid. Preferably, an isolated nucleic acid is free of sequences that naturally flank the nucleic acid (i.e. sequences located at the 5'- and 3'-termini of the nucleic acid) in the genomic DNA of the organism from which the nucleic acid is derived. For example, in various embodiments, isolated MANF DNA molecules can contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue from which the nucleic acid is derived (e.g., brain, heart, liver, spleen, etc.). Moreover, an isolated nucleic acid molecule, such as a cDNA molecule, can be substantially free of other cellular material or culture medium when produced by recombinant techniques, or of chemical precursors or other chemicals when chemically synthesized.

A nucleic acid molecule of the invention, e.g., a MANF nucleic acid molecule, or a complement of this aforementioned nucleotide sequence, can be isolated using standard molecular biology techniques and the provided sequence information. Using all or a portion of a MANF nucleic acid sequence of interest as a hybridization probe, MANF molecules can be isolated using standard hybridization and cloning techniques (Ausubel et al, In Current protocols in Molecular Biology, John Wiley and Sons, publishers, 1989); Sambrook et al, supra).

"Analogs" are nucleic acid sequences or amino acid sequences that have a structure similar to, but not identical to, the native compound but differ from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions (Ausubel et al., supra).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Control sequences" are DNA sequences that enable the expression of an operably-linked coding sequence in a particular host organism. Prokaryotic control sequences include promoters, operator sequences, and ribosome binding sites. Eukaryotic cells utilize promoters, polyadenylation signals, and enhancers.

"Operably-linked nucleic acid" is operably-linked when it is placed into a functional relationship with another nucleic acid sequence. For example, a promoter or enhancer is operably-linked to a coding sequence if it affects the transcription of the sequence, or a ribosome-binding site is operably-linked to a coding sequence if positioned to facilitate translation. Generally, "operably-linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "genomic DNA" is a DNA strand which has a nucleotide sequence homologous with a gene. By way of example, both a fragment of a chromosome and a cDNA derived by reverse transcription of a mammalian mRNA are genomic DNAs.

"Oligonucleotide" comprises a series of linked nucleotide residues, which oligonucleotide has a sufficient number of nucleotide bases to be used in a PCR reaction or other application. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

"Stringency". Homologs (i.e., nucleic acids encoding MANF molecules derived from species other than human) or other related sequences (e.g., paralogs) can be obtained by low, moderate or high stringency hybridization with all or a portion of the particular human sequence as a probe using methods well known in the art for nucleic acid hybridization and cloning.

The specificity of single stranded DNA to hybridize complementary fragments is determined by the "stringency" of the reaction conditions. Hybridization stringency increases as the propensity to form DNA duplexes decreases. In nucleic acid hybridization reactions, the stringency can be chosen to either favour specific hybridizations (high stringency), which can be used to identify, for example, full-length clones from a library. Less-specific hybridizations (low stringency) can be used to identify related, but not exact, DNA molecules (homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide which decreases DNA duplex stability. In general, the longer the probe, the higher the temperature required for proper annealing. A common approach is to vary the temperature: higher relative temperatures result in more stringent reaction conditions. (Ausubel et al., supra) provide an excellent explanation of stringency of hybridization reactions.

To hybridize under "stringent conditions" describes hybridization protocols in which nucleotide sequences at least 60% homologous to each other remain hybridized. Generally, stringent conditions are selected to be about 5 degrees of Celsius lower than the thermal melting point (Tm) for the specific sequence at a defined ionic strength WO 01/70174 PCT/USOI/0904330. Low stringency "low stringent conditions" use washing solutions and hybridization conditions that are less stringent than those for moderate stringency (Sambrook, supra), such that a polynucleotide will hybridize to the entire, fragments, derivatives or analogs of a target MANF target sequence. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40 degrees of Celsius, followed by one or more washes in 2×SSC, 25 mM Tris-HCl (pH 7.4), 5 mM EDTA, and 0.1% SDS at 50 degrees of Celsius. Other conditions of low stringency, such as those for cross-species hybridizations are described in (Ausubel et al., supra; Kriegler M P (1990) Gene transfer and expression; a laboratory manual; Shilo and Weinberg, Proc. Natl. Acad. Sci. USA 78:6789-6792 (1981)).

PCR amplification techniques can be used to amplify MANF using cDNA, mRNA or alternatively, genomic DNA, as a template and appropriate oligonucleotide primers. Such nucleic acids can be cloned into an appropriate vector and characterized by DNA sequence analysis. Furthermore, oligonucleotides corresponding to MANF sequences can be prepared by standard synthetic techniques, e.g., an automated DNA synthesizer.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded.

Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of the nucleic acid encoding the desired protein, or mutant thereof, to acell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5.3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

"Probes" are nucleic acid sequences of variable length, preferably between at least about 10 nucleotides (nt), 100 nt, or many (e.g., 6000 nt) depending on the specific use. Probes are used to detect identical, similar, or complementary nucleic acid sequences. Longer length probes can be obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies. Probes will also hybridize to nucleic acid molecules in biological samples, thereby enabling immediate applications in chromosome mapping, linkage analysis, tissue identification and/or typing, and a variety of forensic and diagnostic methods of the invention.

Probes are substantially purified oligonucleotides that will hybridize under stringent conditions to at least optimally 12, 25, 50, 100, 150, 200, 250, 300, 350 or 400 consecutive sense strand nucleotide sequence; or an anti-sense strand nucleotide sequence; or of a naturally occurring mutant of the MANF DNA sequence of interest.

The full- or partial length native sequence MANF DNA may be used to "pull out" similar (homologous) sequences (Ausubel et al., supra; Sambrook, supra), such as: (1) full-length or fragments of MANF cDNA from a cDNA library from any species (e.g. human, murine, feline, canine, bacterial, viral, retroviral, yeast), (2) from cells or tissues, (3) variants within a species, and (4) homologues and variants from other species. To find related sequences that may encode related genes, the probe may be designed to encode unique sequences or degenerate sequences. Sequences may also be genomic sequences including promoters, enhancer elements and introns of native MANF sequence.

To detect hybridizations, probes are labeled using, for example, radionuclides such as 32P or 35S, or enzymatic labels such as alkaline phosphatase coupled to the probe via avidin-biotin systems. Labeled probes are used to detect nucleic acids having a complementary sequence to that of MANF in libraries of cDNA, genomic DNA or mRNA of a desired species. Such probes can be used as a part of a diagnostic test kit for identifying cells or tissues which mis-express a MANF, such as by measuring a level of a MANF in a sample of cells from a subject e.g., detecting MANF mRNA levels or determining whether a genomic MANF has been mutated or deleted.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Homologs" are nucleic acid sequences or amino acid sequences of a particular gene that are derived from different species.

A "homologous nucleic acid sequence" or "homologous amino acid sequence," or variations thereof, refer to sequences characterized by a homology at the nucleotide level or amino acid level. Homologous nucleotide sequences encode those sequences coding for isoforms of MANF. Isoforms can be expressed in different tissues of the same organism as a result of, for example, alternative splicing of RNA. Alternatively, different genes can encode isoforms. In the invention, homologous nucleotide sequences include nucleotide sequences encoding for a MANF of species other than humans, including, but not limited to vertebrates, and thus can include, e.g., frog, mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding a human MANF. Homologous nucleic acid sequences include those nucleic acid sequences that encode conservative amino acid substitutions in a MANF sequence of interest, as well as a polypeptide possessing MANF biological activity.

"Percent (%) nucleic acid sequence identity" with respect to a MANF is defined as the percentage of nucleotides in a candidate sequence that are identical with the nucleotides in that particular MANF, after aligning the sequences and introducing gaps, if necessary, to achieve the maximum percent sequence identity.

Alignment for purposes of determining % nucleic acid sequence identity can be achieved in various ways that are within the skill in the art, for instance, using publicly available computer software such as BLAST, BLAST-2, ALIGN, Megalign (DNASTAR) or ClustalX software. Those skilled in the art can determine appropriate parameters for measuring alignment, including any algorithms needed to achieve maximal alignment over the full length of the sequences being compared.

BLAST protein searches can be performed with the XBLAST program (designated "blastn" at the NCBI web site) or the NCBI "blastp" program, using the following parameters: expectation value 10.0, BLOSUM 62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25: 3389-3402). Alternatively, PSI-Blast or PHI-Blast can be used to perform an iterated search which detects distant relationships between molecules and relationships between molecules which share a common pattern. When utilizing BLAST, Gapped BLAST, PSI-Blast, and PHI-Blast programs, the default parameters of the respective programs (e.g., XBLAST and NBLAST) can be used. See http://www.ncbi.nlm.nih.gov.

The "open reading frame" (ORF) of a MANF gene encodes MANF. An ORF is a nucleotide sequence that has commonly a start codon (ATG) and terminates commonly with one of the three "stop" codons (TAA, TAG, or TGA). In this invention, however, an ORF—may be any part of a coding sequence that may or may not comprise a start codon and a stop codon. To achieve a unique sequence, preferable MANF—ORFs encode at least 50 amino acids.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic normaturally occurring analogs thereof linked via peptide bonds, related naturally occurring structural variants, and synthetic non-naturally occurring analogs thereof. Synthetic polypeptides can be synthesized, for example, using an automated polypeptide synthesizer.

By "tag" polypeptide is meant any protein which, when linked by a peptide bond to a protein of interest, may be used to localize the protein, to purify it from a cell extract, to immobilize it for use in binding assays, or to otherwise study its biological properties and/or function. A chimeric (i.e., fusion) protein containing a "tag" epitope can be immobilized on a resin which binds the tag. Such tag epitopes and resins which specifically bind them are well known in the art and include, for example, tag epitopes comprising a plurality of sequential histidine residues (His6), which allows isolation of a chimeric protein comprising such an epitope on nickel-nitrilotriacetic acid-agarose, a hemagglutinin (HA) tag epitope allowing a chimeric protein comprising such an epitope to bind with an anti-HA-monoclonal antibody affinity matrix, a myc tag epitope allowing a chimeric protein comprising such an epitope to bind with an antimyc-monoclonal antibody affinity matrix, a glutathione-S-transferase tag epitope, and a maltose binding protein (MBP) tag epitope, which can induce binding between a protein comprising such an epitope and a glutathione- or maltose Sepharose column, respectively. Production of proteins comprising such tag epitopes is well known in the art and is described in standard treatises such as Sambrook et al., supra, and Ausubel et al., supra. Likewise, antibodies to the tag epitope allow detection and localization of the fusion protein in, for example, Western blots, ELISA assays, and immunostaining of cells.

The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, F(ab') and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567 (Cabilly et al.)). The "monoclonal antibodies" may also be isolated from phage antibody libraries using the techniques described in Clackson et al, Nature 352:624-628 (1991) and Marks et al., J. Mol. Biol., 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., Proc. Natl. Acad. Sci. USA, 81:6851-6855 (1984)).

"Humanized" forms of non-human (e.g., murine) antibodies are chimeric immunoglobulins, immunoglobulin chains or fragments thereof (such as Fv, Fab, Fab', F(ab') or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522-525 (1986); Reichmann et al., Nature, 332:323-329 (1988); and Presta, Curr. Op. Struct. Biol., 2:593-596 (1992). The humanized antibody includes a Primatized antibody wherein the antigen-binding region of the antibody is derived from an antibody produced by immunizing macaque monkeys with the antigen of interest.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatocyte growth factor; fibroblast growth factor; prolactin; placental lactogen; tumor necrosis factor-.alpha. and -.beta.; mullerian-inhibiting substance; mouse gonadotropin-associated peptide; inhibin; activin; vascular endothelial growth factor; integrin; thrombopoietin (TPO); neurotrophic factors or nerve growth factors such as NGF, NT-3, NT4, NT-6, BDNF, CNTF, GDNF, artemin, neurturin, persephin, AL-1 and other eph-receptor family ligands; platelet derived growth factor; transforming growth factors (TGFs) such as TGF-alpha. and TGF-beta.; insulin-like growth factor-I and -II; erythropoietin (EPO); osteoinductive factors; interferons such as interferon-alpha., -beta., and -gamma.; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL4, IL-5, IL-6, IL-7, IL-8, IL-9, IL-11, IL-12; and other polypeptide factors including LIF and kit ligand (KL). As used herein, the term cytokine includes proteins from natural sources or from recombinant cell culture and biologically active equivalents of the native sequence cytokines. Also included are genetically engineered molecules which regulate cytokine activity such as TrkA-IgG or other soluble receptor chimeras.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Physiologically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

"A polypeptide having biological activity" refers to a polypeptide exhibiting activity similar to, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about ten-fold less activity, and most preferably, not more than about three-fold less activity relative to the polypeptide of the present invention).

"Treatment" refers to both therapeutic treatment and prophylactic or preventative measures. Those in need of treatment include those already with the disorder as well as those in which the disorder is to be prevented.

Due to the degeneracy of the genetic code, one of ordinary skill in the art will immediately recognize that a large number of the nucleic acid molecules having a sequence at least 80%, 85%, 90%, 95%, 96%, 97%, 98%, 99%, or 100% identical to the nucleic acid sequence of the cDNA contained in SEQ ID NO:1 or fragments thereof, will encode polypeptides "having functional activity." In fact, since degenerate variants of any of these nucleotide sequences all encode the same polypeptide, in many instances, this will be, clear to the skilled artisan. It will be further recognized in the art that, for such nucleic acid molecules that are not degenerate variants, a reasonable number will also encode a polypeptide having functional activity. This is because the skilled artisan is fully aware of amino acid substitutions that are either less likely or not likely to significantly effect protein function (e.g. replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

In addition to naturally occurring allelic variants of MANF, changes can be introduced by mutation into MANF sequences that incur alterations in the amino acid sequences of the encoded MANF polypeptide. Nucleotide substitutions leading to amino acid substitutions at "non-essential" amino acid residues can be made in the sequence of a MANF polypeptide. A "non-essential" amino acid residue is a residue that can be altered from the wild-type sequences of MANF without altering its biological activity, whereas an "essential" amino acid residue is required for such biological activity. For example, amino acid residues that are conserved among the MANF molecules of the invention are predicted to be particularly non-amenable to alteration. Amino acids for which conservative substitutions can be made are well known in the art. Useful conservative substitutions are shown in Table B, "Preferred substitutions." Conservative substitutions whereby an amino acid of one class is replaced with another amino acid of the same type fall within the scope of the subject invention so long as the substitution does not materially alter the biological activity of the compound.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) could be used. See Cunningham et al., Science 244:1081-1085 (1989). The resulting mutant molecules can then be tested for biological activity. Besides conservative amino acid substitutions (See Table B below), variants of the present invention include (i) substitutions with one or more of the non-conserved amino acid residues, where the substituted amino acid residues may or may not be one encoded by the genetic code, or (ii) substitutions with one or more of the amino acid residues having a substituent group, or (iii) fusion of the mature polypeptide with another compound, such as a compound to increase the stability and/or solubility of the polypeptide (for example, 896I polyethylene glycol), or (iv) fusion of the polypeptide with additional amino acids, such as, for example, an IgG Fc fusion peptide, serum albumin (preferably human serum albumin) or a fragment or variant thereof, or leader or secretory sequence, or a sequence facilitating purification. Such variant polypeptides are deemed to be within the scope of those skilled in the art from the teachings herein.

TABLE B

Preferred substitutions

| Original residue | Exemplary substitutions | Preferred substitutions |
| --- | --- | --- |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

In addition sequence polymorphisms that change the amino acid sequences of the MANF may exist within a population. For example, allelic variation among individuals will exhibit genetic polymorphism in MANF. The terms "gene" and "recombinant gene" refer to nucleic acid molecules comprising an open reading frame (ORF) encoding MANF, preferably a vertebrate MANF. Such natural allelic variations can typically result in 1-5% variance in MANF. Any and all such nucleotide variations and resulting amino acid polymorphisms in the MANF, which are the result of natural allelic variation and that do not alter the functional activity of the MANF are within the scope of the invention.

Moreover, MANF from other species that have a nucleotide sequence that differs from the human sequence of MANF are contemplated. Nucleic acid molecules corresponding to natural allelic variants and homologues of MANF cDNAs of the invention can be isolated based on their homology to MANF using cDNA-derived probes to hybridize to homologous MANF sequences under stringent conditions.

"MANF variant polynucleotide" or "MANF variant nucleic acid sequence" means a nucleic acid molecule which encodes an active MANF that (1) has at least about 80% nucleic acid sequence identity with a nucleotide acid sequence encoding a full-length native MANF, (2) a full-length native MANF lacking the signal peptide, or (3) any other fragment of a full-length MANF. Ordinarily, a MANF variant polynucleotide will have at least about 80% nucleic acid sequence identity, more preferably at least about 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with the nucleic acid sequence encoding a full-length native MANF. A MANF variant polynucleotide may encode full-length native MANF lacking the signal peptide with or without the signal sequence, or any other fragment of a full-length MANF. Variants do not encompass the native nucleotide sequence.

Ordinarily, MANF variant polynucleotides are at least about 30 nucleotides in length, often at least about 60, 90, 120, 150, 180, 210, 240, 270, 300, 400 nucleotides in length, more often at least about 500 nucleotides in length, or more.

The structure and sequence of the mammalian MANF cDNA sequence which encodes the mouse and human sequences disclosed herein, make it possible to clone gene sequences from other mammals which encode the MANF. Of particular interest to the present invention is the ability to clone the human MANF molecules using the sequences disclosed herein. The DNA encoding MANF may be obtained from any cDNA library prepared from tissue believed to possess the MANF mRNA and to express it at a detectable level, as shown herein in the Examples. Accordingly, MANF DNA can be conveniently obtained from a cDNA library prepared, for example, from mammalian fetal liver, brain, muscle, intestine, and peripheral nerves. The MANF-encoding gene may also be obtained from a genomic library or by oligonucleotide synthesis.

Libraries are screened with probes (such as antibodies to the MANF or oligonucleotides of about 20-80 bases) designed to identify the gene of interest or the protein encoded by it. Screening the cDNA or genomic library with the selected probe may be conducted using standard procedures as described in chapters 10-12 of Sambrook et al., Molecular Cloning: A Laboratory Manual (New York: Cold Spring Harbor Laboratory Press, 1989) or alternatively to use PCR methodology as described in section 14 of Sambrook et al., supra.

Amino acid sequence variants of MANF are prepared by introducing appropriate nucleotide changes into the MANF DNA, or by synthesis of the desired MANF polypeptide. Such variants represent insertions, substitutions, and/or specified deletions of, residues within or at one or both of the ends of the amino acid sequence of a naturally occurring MANF, such as the MANF shown SEQ ID NO:s 2 and 4. Preferably, these variants represent insertions and/or substitutions within or at one or both ends of the mature sequence, and/or insertions, substitutions and/or specified deletions within or at one or both of the ends of the signal sequence of the MANF. Any combination of insertion, substitution, and/or specified deletion is made to arrive at the final construct, provided that the final construct possesses the desired biological activity as defined herein.

Variations in the native sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis.

The nucleic acid (e.g., cDNA or genomic DNA) encoding the MANF is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

The MANFs of this invention may be produced recombinantly not only directly, but also as a fusion polypeptide with a heterologous polypeptide, which is preferably a signal sequence or other polypeptide having a specific cleavage site at the N-terminus of the mature protein or polypeptide. Fusion proteins can be easily created using recombinant methods. A nucleic acid encoding MANF can be fused in-frame with a non-MANF encoding nucleic acid, to the MANF N- or COOH-terminus, or internally. Fusion genes may also be synthesized by conventional techniques, including automated DNA synthesizers. A MANF fusion protein may include any portion to the entire MANF, including any number of the biologically active portions. Fusion polypeptides are useful in expression studies, cell-localization, bioassays, and MANF purification Alternatively, MANF fusion protein can also be easily created using PCR amplification and anchor primers that give rise to complementary overhangs between two consecutive gene fragments that can subsequently be annealed and reamplified to generate a chimeric gene sequence (Ausubel et al., supra).

The signal sequence may be a component of the vector, or it may be a part of the MANF DNA that is inserted into the vector. The heterologous signal sequence selected preferably is one that is recognized and processed (i.e., cleaved by a signal peptidase) by the host cell. For prokaryotic host cells that do not recognize and process the native MANF signal sequence, the signal sequence is substituted by a prokaryotic signal sequence selected, for example, from the group of the alkaline phosphatase, penicillinase, or heat-stable enterotoxin II leaders. For yeast secretion the native signal sequence may be substituted by, e.g., the yeast invertase leader, alpha-factor leader (including *Saccharomyces* and *Kluyveromyces*, alpha-factor leaders, the latter described in U.S. Pat. No. 5,010,182 issued Apr. 23, 1991), or acid phosphatase leader, the *Candida albicans* glucoamylase leader (EP 362,179 published Apr. 4, 1990). In mammalian cell expression the native signal sequence (e.g., the MANF presequence that normally directs secretion of MANF from human cells in vivo) is satisfactory, although other mammalian signal sequences may be suitable, such as signal sequences from other animal MANFs, and signal sequences from secreted polypeptides of the same or related species, as well as viral secretory leaders, for example, the herpes simplex gD signal.

Expression and cloning vectors usually contain a promoter that is recognized by the host organism and is operably linked to the MANF nucleic acid. Vector choice is dictated by the organism or cells being used and the desired fate of the vector. Vectors may replicate once in the target cells, or may be "suicide" vectors. In general, vectors comprise signal sequences, origins of replication, marker genes, enhancer elements, promoters, and transcription termination sequences. The choice of these elements depends on the organisms in which the vector will be used and are easily determined. Some of these elements may be conditional, such as an inducible or conditional promoter that is turned "on" when conditions are appropriate.

Vectors can be divided into two general classes: Cloning vectors are replicating plasmid or phage with regions that are non-essential for propagation in an appropriate host cell, and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA. In expression vectors, the introduced DNA is operably linked to elements, such as promoters, that signal to the host cell to transcribe the inserted DNA. Some promoters are exceptionally useful, such as inducible promoters that control gene transcription in response to specific factors. Operably linking MANF or anti-sense construct to an inducible promoter can control the expression of MANF or fragments, or anti-sense constructs. Examples of classic inducible promoters include those that are responsive to a-interferon, heat-shock, heavy metal ions, and steroids such as glucocorticoids (Kaufman R J, Vectors Used for Expression in Mammalian Cells," Methods in Enzymology, Gene Expression Technology, David V. Goeddel, ed., 1990, 185: 487-511) and tetracycline. Other desirable inducible promoters include those that are not endogenous to the cells in which the construct is being introduced, but, however, is responsive in those cells when the induction agent is exogenously supplied.

Promoters are untranslated sequences located upstream (5') to the start codon of a structural gene (generally within about 100 to 1000 bp) that control the transcription and translation of particular nucleic acid sequence, such as the MANF nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to MANF-encoding DNA by removing the promoter from the source DNA by restriction enzyme digestion and inserting the isolated promoter sequence into the vector. Both the native MANF promoter sequence and many heterologous promoters may be used to direct amplification and/or expression of the MANF DNA. However, heterologous promoters are preferred, as they generally permit greater transcription and higher yields of MANF as compared to the native MANF promoter. Various promoters exist for use with prokaryotic, eukaryotic, yeast and mammalian host cells, known for skilled artisan.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding MANF.

Construction of suitable vectors containing one or more of the above-listed components employs standard ligation techniques. Isolated plasmids or DNA fragments are cleaved, tailored, and religated in the form desired to generate the plasmids required.

Particularly useful in the practice of this invention are expression vectors that provide for the transient expression in mammalian cells of DNA encoding MANF. In general, transient expression involves the use of an expression vector that is able to replicate efficiently in a host cell, such that the host cell accumulates many copies of the expression vector and, in turn, synthesizes high levels of a desired polypeptide encoded by the expression vector, Sambrook et al., supra, pp. 16.17-16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of MANF that are biologically active.

Propagation of vertebrate cells in culture (tissue culture) has become a routine procedure. See, e.g., Tissue Culture, Academic Press, Kruse and Patterson, editors (1973). Examples of useful mammalian host cell lines are monkey kidney CV1 line transformed by SV40 (COS-7, ATCC CRL 1651); Chinese hamster ovary cells/−DHFR (CHO, Urlaub et al., Proc. Natl. Acad. Sci. USA, 77:4216 (1980)); human cervical carcinoma cells (HELA, ATCC CCL 2); and canine kidney cells (MDCK, ATCC CCL 34);

Host cells are transfected and preferably transformed with the above-described expression or cloning vectors for MANF production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers.

General aspects of mammalian cell host system transformations have been described in U.S. Pat. No. 4,399,216 issued Aug. 16, 1983. Transformations into yeast are typically carried out according to the method of Van Solingen et al., J. Bact., 130:946 (1977) and Hsiao et al., Proc. Natl. Acad. Sci. USA, 76:3829 (1979). However, other methods for introducing DNA into cells, such as by nuclear microinjection, electroporation, bacterial protoplast fusion with intact cells, or polycations, e.g., polybrene, polyorithine, etc., may also be used. For various techniques for transforming mammalian cells, see Keown et al., Methods in Enzymology, 185:527-537 (1990) and Mansour et al., Nature, 336:348-352 (1988).

Prokaryotic cells used to produce the MANF polypeptides of this invention are cultured in suitable media as described generally in Sambrook et al., supra. In general, principles, protocols, and practical techniques for maximizing the productivity of mammalian cell cultures can be found in Mammalian Cell Biotechnology: a Practical Approach, M. Butler, ed. (IRL Press, 1991).

Gene amplification and/or expression may be measured in a sample directly, for example, by conventional Southern blotting, Northern blotting to quantitate the transcription of mRNA (Thomas, Proc. Natl. Acad. Sci. USA, 77:5201-5205 (1980)), dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide or antibodies recognizing specific duplexes, including DNA duplexes, RNA duplexes, and DNA-RNA hybrid duplexes or DNA-protein duplexes.

Gene expression, alternatively, can be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., Am. J. Clin. Path., 75:734-738 (1980).

Recombinant Production

When MANF is produced in a recombinant cell other than one of human origin, the MANF is completely free of proteins or polypeptides of human origin. However, it is necessary to purify MANF from recombinant cell proteins or polypeptides to obtain preparations that are substantially homogeneous as to MANF. As a first step, the culture medium or lysate can be centrifuged to remove particulate cell debris. MANF can then be purified from contaminant soluble proteins and polypeptides with the following procedures, which are exemplary of suitable purification procedures: by fractionation on an ion-exchange column; ethanol precipitation; reverse phase HPLC; chromatography on silica; chromatofocusing; immunoaffinity; epitope-tag binding resin; SDS-PAGE; ammonium sulfate precipitation; gel filtration using, for example, Sephadex G-75; and protein A Sepharose columns to remove contaminants such as IgG.

MANF variants in which residues have been deleted, inserted, or substituted are recovered in the same fashion as native sequence MANF, taking account of any substantial changes in properties occasioned by the variation. Immunoaffinity resins, such as a monoclonal anti-MANF resin, can be employed to absorb the MANF variant by binding it to at least one remaining epitope.

Variants can be assayed as taught herein. A change in the immunological character of the MANF molecule, such as affinity for a given antibody, can be measured by a competitive-type immunoassay. Other potential modifications of protein or polypeptide properties such as redox or thermal stability, hydrophobicity, susceptibility to proteolytic degradation, or the tendency to aggregate with carriers or into multimers are assayed by methods well known in the art.

This invention encompasses chimeric polypeptides comprising MANF fused to a heterologous polypeptide. A chimeric MANF is one type of MANF variant as defined herein. In one preferred embodiment, the chimeric polypeptide comprises a fusion of the MANF with a tag polypeptide which provides an epitope to which an anti-tag antibody or molecule can selectively bind. The epitope-tag is generally provided at the amino- or carboxyl-terminus of the MANF. Such epitope-tagged forms of the MANF are desirable, as the presence thereof can be detected using a labeled antibody against the tag polypeptide. Also, provision of the epitope tag enables the MANF to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). Other tag polypeptides have been disclosed, Examples include the Flag-peptide (Hopp et al., BioTechnology, 6:1204-1210 (1988)); the KT3 epitope peptide (Martin et al., Science, 255:192-194 (1992)); an alpha-tubulin epitope peptide (Skinner et al., J. Biol. Chem., 266:15163-15166 (1991)); and the T7 gene protein peptide tag (Lutz-Freyermuth et al., Proc. Natl. Acad. Sci. USA, 87:6393-6397 (1990)). Once the tag polypeptide has been selected, an antibody thereto can be generated using the techniques disclosed herein. A C-terminal poly-histidine sequence tag is preferred. Poly-histidine sequences allow isolation of the tagged protein by Ni-NTA chromatography as described (Lindsay et al. Neuron 17:571-574 (1996)), for example.

The general methods suitable for the construction and production of epitope-tagged MANF are the same as those disclosed hereinabove.

Epitope-tagged MANF can be conveniently purified by affinity chromatography using the anti-tag antibody. The matrix to which the affinity antibody is attached is most often agarose, but other matrices are available (e.g. controlled pore glass or poly(styrenedivinyl)benzene). The epitope-tagged MANF can be eluted from the affinity column by varying the buffer pH or ionic strength or adding chaotropic agents, for example.

Chimeras constructed from a MANF sequence linked to an appropriate immunoglobulin constant domain sequence (immunoadhesins) are known in the art. Immunoadhesins reported in the literature include fusions of the T cell receptor (Gascoigne et al., Proc. Natl. Acad. Sci. USA, 84: 2936-2940 (1987)); CD4* (Capon et al., Nature 337: 525-531 (1989); Traunecker et al., Nature, 339: 68-70 (1989); Zettmeissl et al., DNA Cell Biol USA, 9: 347-353 (1990); Bym et al., Nature, 344: 667-670 (1990)); TNF receptor (Ashkenazi et al., Proc. Natl. Acad. Sci. USA, 88: 10535-10539 (1991); Lesslauer et al., Eur. J. Immunol., 27: 2883-2886 (1991); Peppel et al., J. Exp. Med., 174:1483-1489 (1991)); and IgE receptor alpha* (Ridgway et al., J. Cell. Biol., 1 15:abstr. 1448 (1991)), where the asterisk (*) indicates that the receptor is member of the immunoglobulin superfamily.

The simplest and most straightforward immunoadhesin design combines the binding region(s) of the "adhesin" protein with the hinge and Fc regions of an immunoglobulin heavy chain. Ordinarily, when preparing the MANF-immunoglobulin chimeras of the present invention, nucleic acid encoding the MANF will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge and CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimise the biological activity, secretion or binding characteristics of the MANF-immunoglobulin chimeras.

The choice of host cell line for the expression of MANF immunoadhesins depends mainly on the expression vector. Another consideration is the amount of protein that is required. Milligram quantities often can be produced by transient transfections utilizing, for example, calcium phosphate or DEAE-dextran method (Aruffo et al., Cell, 61:1303-1313 (1990); Zettmeissl et al., DNA Cell Biol. US, 9:347-353 (1990)). If larger amounts of protein are desired, the immunoadhesin can be expressed after stable transfection of a host cell line, for example, introducing the expression vectors into Chinese hamster ovary (CHO) cells in the presence of an additional plasmid encoding dihydrofolate reductase.

Treatment

In neurodegenerative diseases neurons die. In Parkinson's disease brain dopaminergic neurons degenerate most prominently in the substantia nigra. We have identified a novel conserved dopamine neurotrophic factor MANF as a survival factor for dopaminergic neurons. The present invention provides viral vector (e.g. AAV and lentivirus vector) expressing recombinant human MANF. By delivering MANF, e.g. by a virus vector expressing MANF proteins, to the rat striatum before and after the injection of the 6-OHDA to the striatum of the rats it is possible to effectively protect and repair the dopaminergic system in the rat model of Parkinson's disease.

The MANF protein and MANF nucleic acid find ex vivo or in vivo therapeutic use for administration to a mammal, particularly humans, in the treatment of diseases or disorders, related to MANF activity or benefited by MANF-responsiveness. Particularly preferred are neurologic disorders, preferably central nervous system disorders, Parkinson's disease, Alzheimers disease, epilepsy and global forebrain ischemia (i.e. stroke).

The patient is administered an effective amount of MANF protein, peptide fragment, or variant of the invention. Therapeutic methods comprising administering MANF, MANF agonists, MANF antagonists or anti-MANF antibodies are within the scope of the present invention. The present invention also provides for pharmaceutical compositions comprising MANF protein, peptide fragment, or derivative in a suitable pharmacological carrier. The MANF protein, peptide fragment, or variant may be administered systemically or locally. Applicable to the methods taught herein, the MANF protein can be optionally administered prior to, after, or preferably concomitantly with (or in complex with) CDNF, GDNF or phospholipids, such as 1-palmitoyl-2-glutaroyl-sn-glycero-3-phosphocholine.

A disease or medical disorder is considered to be nerve damage if the survival or function of nerve cells and/or their axonal processes is compromised. Such nerve damage occurs as the result conditions including (a) Physical injury, which causes the degeneration of the axonal processes and/or nerve cell bodies near the site of the injury; (b) Ischemia, as a stroke; (c) Exposure to neurotoxins, such as the cancer and AIDS chemotherapeutic agents such as cisplatin and dideoxycytidine (ddC), respectively; (d) Chronic metabolic diseases, such as diabetes or renal dysfunction; and (e) Neurodegenerative diseases such as Parkinson's disease, Alzheimer's disease, and Amyotrophic Lateral Sclerosis (ALS), which cause the degeneration of specific neuronal populations. Conditions involving nerve damage include Parkinson's disease, Alzheimer's disease, Amyotrophic Lateral Sclerosis, stroke, diabetic polyneuropathy, toxic neuropathy, and physical damage to the nervous system such as that caused by physical injury of the brain and spinal cord or crush or cut injuries to the arm and hand or other parts of the body, including temporary or permanent cessation of blood flow to parts of the nervous system, as in stroke.

It is contemplated that MANF may be employed to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to diabetic peripheral neuropathy, distal sensorimotor neuropathy, or autonomic neuropathies such as reduced motility of the gastrointestinal tract or atony of the urinary bladder. Examples of neuropathies associated with systemic disease include post-polio syndrome or AIDS-associated neuropathy; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine. Correspondingly, neurotrimin antagonists would be expected to have utility in diseases characterized by excessive neuronal activity.

Alzheimer's Disease is marked by widespread neurodegeneration in the brain including an enhanced loss of the cholinergic neurons that reside in the basal forebrain. The loss of the basal forebrain cholinergic neurons contributes to the cognitive and spatial memory deficits in Alzheimer's diseased patients (Gilmor et al., 1999; Lehericy et al. 1993). Restoring and modulating cholinergic function in Alzheimer's patients is a candidate treatment for the disease (Sramek and Cutler, 1999; Mufson et al., 1998). Other neural cell types may also be involved with the disease.

A patient suffering from Parkinson's disease can be treated at the earliest signs of disease symptoms, such as impaired motor function or impaired cognitive function, in order to halt the progression of neurodegeneration. It is also contemplated that the MANF cultured cells are administered to individuals in late stages of disease to slow the progression of the nervous system damage.

It is also contemplated by the invention that administration of the MANF product in combination with a neurotherapeutic agent commonly used to treat Parkinson's disease will create a synergism of the two treatments, thereby causing marked improvement in patients receiving the combination therapy as compared to individuals receiving only a single therapy.

Pramipexole (mirapex) and levodopa are effective medications to treat motor symptoms of early Parkinson disease (PD). In vitro studies and animal studies suggest that pramipexole may protect and that levodopa may either protect or damage dopamine neurons. Neuroimaging offers the potential of an objective biomarker of dopamine neuron degeneration in PD patients. Coenzyme Q10, a neurotransmitter that is expressed at low levels in Parkinson's patients, is also used for treatment of PD. Levodopa can be combined with another drug such as carbidopa to aid in relieving the side effects of L-dopa. Other medications used to treat Parkinson's disease, either as solo agents or in combination, are Sinemet, Selegiline, (marketed as Eldepryl) may offer some relief from early Parkinson symptoms. Amantadine (Symmetrel) is an anti-viral drug that also provides an anti-Parkinson effect, and is frequently used to widen the "therapeutic window" for Levodopa when used in combination with Sinemet.

It is contemplated that treatment with MANF either before, after or simultaneously with any of the above neurotherapeutics will enhance the effect of the neurotherapeutic agent, thereby reducing the amount of agent required by an individual and reducing unwanted side effects produced by multiple or large doses of neurotherapeutic.

Genetic manipulations to achieve modulation of protein expression or activity is also specifically contemplated. For example, where administration of proteins is contemplated, administration of a gene therapy vector to cause the protein of interest to be produced in vivo is also contemplated. Where inhibition of proteins is contemplated (e.g., through use of antibodies or small molecule inhibitors), inhibition of protein expression in vivo by genetic techniques, such as knock-out techniques or anti-sense therapy, is contemplated.

Any suitable vector may be used to introduce a transgene of interest into an animal. Exemplary vectors that have been described in the literature include replication-deficient retroviral vectors, including but not limited to lentivirus vectors [Kim et al., J. Virol., 72(1): 811-816 (1998); Kingsman & Johnson, Scrip Magazine, October, 1998, pp. 43-46.]; adenoviral (see, for example, U.S. Pat. No. 5,824,544; U.S. Pat. No. 5,707,618; U.S. Pat. No. 5,792,453; U.S. Pat. No. 5,693,509; U.S. Pat. No. 5,670,488; U.S. Pat. No. 5,585,362; Quantin et al., Proc. Natl. Acad. Sci. USA, 89: 2581-2584 (1992); Stratford-Perricadet et al., J. Clin. Invest., 90: 626-630 (1992); and Rosenfeld et al., Cell, 68: 143-155 (1992)), retroviral (see, for example, U.S. Pat. No. 5,888,502; U.S. Pat. No. 5,830,725; U.S. Pat. No. 5,770,414; U.S. Pat. No. 5,686,278; U.S. Pat. No. 4,861,719), adeno-associated viral (see, for example, U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479; Gnatenko et al., J. Investig. Med., 45: 87-98 (1997), an adenoviral-adenoassociated viral hybrid (see, for example, U.S. Pat. No. 5,856,152) or a vaccinia viral or a herpesviral (see, for example, U.S. Pat. No. 5,879,934; U.S. Pat. No. 5,849,571; U.S. Pat. No. 5,830,727; U.S. Pat. No. 5,661,033; U.S. Pat. No. 5,328,688); Lipofectin-mediated gene transfer (BRL); liposomal vectors [See, e.g., U.S. Pat. No. 5,631,237 (Liposomes comprising Sendai virus proteins)]; and combinations thereof. All of the foregoing documents are incorporated herein by reference in the entirety. Replication-deficient adenoviral vectors, adeno-associated viral vectors and lentiviruses constitute preferred embodiments.

In embodiments employing a viral vector, preferred polynucleotides include a suitable promoter and polyadenylation sequence to promote expression in the target tissue of interest. For many applications of the present invention, suitable promoters/enhancers for mammalian cell expression include, e.g., cytomegalovirus promoter/enhancer [Lehner et al., J. Clin. Microbiol., 29:2494-2502 (1991); Boshart et al., Cell, 41:521-530 (1985)]; Rous sarcoma virus promoter [Davis et al., Hum. Gene Ther., 4:151 (1993)]; simian virus 40 promoter, long terminal repeat (LTR) of retroviruses, keratin 14 promoter, and a myosin heavy chain promoter.

In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA, 83:41434146 (1986)). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, ex vivo, or in vivo in the cells of the intended host. Techniques suitable for the transfer of nucleic acid into mammalian cells in vitro include the use of liposomes (Nicolau and Sene, Biochim. Biophys. Acta, 721:185-190 (1982); Fraley, et al., Proc. Natl. Acad. Sci. USA, 76:3348-3352 (1979); Felgner, Sci. Am., 276(6):102-6 (1997); Felgner, Hum. Gene Ther., 7(15):1791-3, (1996)), electroporation (Tur-Kaspa, et al., Mol. Cell. Biol., 6:716-718, (1986); Potter, et al., Proc. Nat. Acad. Sci. USA, 81:7161-7165, (1984)), direct microinjection (Harland and Weintraub, J. Cell Biol., 101:1094-1099 (1985)), cell fusion, DEAE-dextran (Gopal, Mol. Cell. Biol., 5:1188-1190 (1985), the calcium phosphate precipitation method (Graham and Van Der Eb, Virology, 52:456-467 (1973); Chen and Okayama, Mol. Cell. Biol., 7:2745-2752, (1987); Rippe, et al., Mol. Cell. Biol., 10:689-695 (1990), cell sonication (Fechheimer, et al., Proc. Natl. Acad. Sci. USA, 84:8463-8467 (1987)), gene bombardment using high velocity microprojectiles (Yang, et al., Proc. Natl. Acad. Sci. USA, 87:9568-9572 (1990). The currently preferred in vivo gene transfer techniques include transfection with viral (typically retroviral) vectors and viral coat protein-liposome mediated transfection (Dzau et al., Trends in Biotechnology, 11:205-210 (1993)). In some situations it is desirable to provide the nucleic acid source with an agent that targets the target cells, such as an antibody specific for a cell surface membrane protein or the target cell, a ligand for a receptor on the target cell. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., J. Biol. Chem., 262:4429-4432 (1987); and Wagner et al., Proc. Natl. Acad. Sci. USA, 87:3410-3414 (1990). For review of the currently known gene marking and gene therapy protocols see Anderson et al., Science, 256:808-813 (1992).

In a particular embodiment of the invention, the expression construct (or indeed the peptides discussed above) may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, "In Liver Diseases, Targeted Diagnosis And Therapy Using Specific Receptors And Ligands," Wu, G., Wu, C., ed., New York: Marcel Dekker, pp. 87-104 (1991)). The addition of DNA to cationic liposomes causes a topological transition from liposomes to optically birefringent liquid-crystalline condensed globules (Radler, et al., Science, 275(5301):810-4, (1997)). These DNA-lipid complexes are potential non-viral vectors for use in gene therapy and delivery.

Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA (Kaneda, et al., Science, 243:375-378 (1989)). In other embodiments, the liposome may be complexed or employed in conjunction with nuclear nonhistone chromosomal proteins (HMG-1) (Kato, et al., J. Biol. Chem., 266:3361-3364 (1991)). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu (1993), supra).

In another embodiment of the invention, the expression construct may simply consist of naked recombinant DNA or plasmids. Transfer of the construct may be performed by any of the methods mentioned above that physically or chemically permeabilize the cell membrane. This is applicable particularly for transfer in vitro, however, it may be applied for in vivo use as well. Dubensky, et al., *Proc. Nat. Acad. Sci. USA*, 81:7529-7533 (1984) successfully injected polyomavirus DNA in the form of $CaPO_4$ precipitates into liver and spleen of adult and newborn mice demonstrating active viral replication and acute infection. Benvenisty and Neshif, *Proc. Nat. Acad. Sci. USA*, 83:9551-9555 (1986) also demonstrated that direct intraperitoneal injection of $CaPO_4$ precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein, et al., *Nature*, 327:70-73 (1987)). Several devices for accelerating small particles have been developed. One such device relies on a high voltage discharge to generate an electrical current, which in turn provides the motive force (Yang, et al., *Proc. Natl. Acad. Sci. USA*, 87:9568-9572 (1990)). The microprojectiles used have consisted of biologically inert substances such as tungsten or gold beads.

Those of skill in the art are aware of how to apply gene delivery to in vivo and ex vivo situations. For viral vectors, one generally will prepare a viral vector stock. Depending on the type of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various cell types. For practically any cell, tissue or organ type, systemic delivery is contemplated. In other embodiments, a variety of direct, local and regional approaches may be taken. For example, the cell, tissue or organ may be directly injected with the expression vector or protein.

In a different embodiment, ex vivo gene therapy is contemplated. In an ex vivo embodiment, cells from the patient are removed and maintained outside the body for at least some period of time. During this period, a therapy is delivered, after which the cells are reintroduced into the patient.

The invention also provides antagonists of MANF activation (e.g., MANF antisense nucleic acid, neutralizing antibodies). Administration of MANF antagonist to a mammal having increased or excessive levels of endogenous MANF activation is contemplated, preferably in the situation where such increased levels of MANF lead to a pathological disorder.

Viral Vectors Expressing MANF

The strategy for transferring genes into target cells in vivo includes the following basic steps: (1) selection of an appropriate transgene or transgenes whose expression is correlated with CNS disease or dysfunction; (2) selection and development of suitable and efficient vectors for gene transfer; (3) demonstration that in vivo transduction of target cells and transgene expression occurs stably and efficiently; (4) demonstration that the in vivo gene therapy procedure causes no serious deleterious effects; and (5) demonstration of a desired phenotypic effect in the host animal.

Although other vectors may be used, preferred vectors for use in the methods of the present invention are viral and non-viral vectors. The vector selected should meet the following criteria: 1) the vector must be able to infect targeted cells and thus viral vectors having an appropriate host range must be selected; 2) the transferred gene should be capable of persisting and being expressed in a cell for an extended period of time (without causing cell death) for stable maintenance and expression in the cell; and 3) the vector should do little, if any, damage to target cells.

Because adult mammalian brain cells are non-dividing, the recombinant expression vector chosen must be able to transfect and be expressed in non-dividing cells. At present, vectors known to have this capability include DNA viruses such as adenoviruses, adeno-associated virus (AAV), and certain RNA viruses such as HIV-based lentiviruses, feline immunodeficiency virus (FIV) and equine immunodeficiency virus (EIV). Other vectors with this capability include herpes simplex virus (HSV). However, some of these viruses (e.g., AAV and HSV) can produce toxicity and/or immunogenicity. Recently, an HIV-based lentiviral vector system has recently been developed which, like other retroviruses, can insert a transgene into the nucleus of host cells (enhancing the stability of expression) but, unlike other retroviruses, can make the insertion into the nucleus of non-dividing cells. Lentiviral vectors have been shown to stably transfect brain cells after direct injection, and stably express a foreign transgene without detectable pathogenesis from viral proteins (see, Naldini, et al., Science, 272:263-267 (1996), the disclosure of which is incorporated by reference). Following the teachings of the researchers who first constructed the HIV-1 retroviral vector, those of ordinary skill in the art will be able to construct lentiviral vectors suitable for use in the methods of the invention (for more general reference concerning retrovirus construction, see, e.g., Kriegler, Gene Transfer and Expression, A Laboratory Manual, W. Freeman Co. (NY 1990) and Murray, E J, ed., Methods in Molecular Biology, Vol. 7, Humana Press (NJ 1991)).

The use of recombinant AAV vectors is efficient; their infection is relatively long-lived and is generally non-toxic, unless a toxic transgene is recombined therein. AAV is a helper-dependent parvovirus consisting of a single strand 4.7 kb DNA genome surrounded by a simple, non-enveloped icosahedral protein coat. About 85% of the adult human population is seropositive for AAV. Nonetheless, no pathology has been associated with AAV infection. AAV is dependent on Adenovirus or herpesvirus as a helper virus to establish productive infection by AAV. In the absence of helper virus, the AAV genome also amplifies in response to toxic challenge (UV irradiation, hydroxyurea exposure). If there is no toxic challenge or helper virus, wild-type AAV integrates into human chromosome 19 site-specifically. This is driven by the AAV Rep proteins that mediate the formation of an AAV-chromosome complex at the chromosomal integration site. Most of the viral genome (96%) may be removed, leaving only the two 145 base pair (bp) inverted terminal repeats (ITRs) for packaging and integration of the viral genome. Techniques for efficient propagation of recombinant AAV, rAAV, have been developed in the art: the use of mini-adenoviral genome plasmids, plasmids encoding AAV packaging functions and adenovirus helper functions in single plasmids. Moreover, methods of rAAV for isolation of highly purified rAAV are a relatively straightforward and rapid undertaking, as is titration of rAAV stocks. To trace rAAV-mediated transgene expression the green fluorescent protein (GFP), a well-characterized 238 amino acid fluorescent protein, is frequently used in a bicistronic arrangement in rAAV. Selective and specific expression of rAAV mediated gene transfer through different promoters has also been identified. We use a commercial available AAV Helper-free system (Invitrogen) to construct our recombinant AAVs. MANF is cloned into vectors/plasmids of the AAV system using conventional recombinant DNA techniques.

Construction of vectors for recombinant expression of nervous system growth factors for use in the invention may be accomplished using conventional techniques which do not require detailed explanation to one of ordinary skill in the art. Specifics for construction of AAV vector is set forth in here. For further review, those of ordinary skill may wish to consult Maniatis et al., in Molecular Cloning: A Laboratory Manual, Cold Spring Harbor Laboratory, (NY 1982).

Briefly, construction of recombinant expression vectors employs standard ligation techniques. For analysis to confirm correct sequences in vectors constructed, the ligation mixtures may be used to transform a host cell and successful transformants selected by antibiotic resistance where appropriate. Vectors from the transformants are prepared, analyzed by restriction and/or sequenced by, for example, the method of Messing, et al., (Nucleic Acids Res., 9:309, 1981), the method of Maxam, et al., (Methods in Enzymology, 65:499, 1980), or other suitable methods which will be known to those skilled in the art. Size separation of cleaved fragments is performed using conventional gel electrophoresis as described, for example, by Maniatis, et al., (Molecular Cloning, pp. 133-134, 1982).

Expression of a gene (MANF) is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., Cell 27:299 (1981); Corden et al., Science 209:1406 (1980); and Breathnach and Chambon, Ann. Rev. Biochem. 50:349 (1981)). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney murine leukemia virus (MLV) and Rous sarcoma virus (RSV) LTRs contain promoter and enhancer sequences (Jolly et al., Nucleic Acids Res. 11:1855 (1983); Capecchi et al., In: Enhancer and eukaryotic gene expression, Gulzman and Shenk, eds., pp. 101-102, Cold Spring Harbor Laboratories (NY 1991). Other potent promoters include those derived from cytomegalovirus (CMV) and other wild-type viral promoters.

An alternative approach to change the expression of MANF is to change the pre-region (signal sequence) of the protein to an equivalent signal sequence from a protein known to be expressed in high amounts, such as the immunoglobulin heavy chain. Alternatively, the signal sequence of MANF can be changed to that of a protein known to be expressed in the appropriate target tissue or organ. Likewise, deletion or insertion variants of MANF might be more efficiently expressed and more stable than the native MANF protein.

Methods of making and using rAAV and delivery of rAAV to various cells in vivo are found in U.S. Pat. Nos. 5,720,720; 6,027,931; 6,071,889; WO 99/61066; all of which are hereby incorporated by reference for this purpose. Different serotypes of AAV are available, and they show tissue tropism. Thus, the use of the accurate serotype depends on which tissue is to be transduced.

With regard to methods for the successful, localized, long-term and non-toxic transgene expression in the nervous system using adeno-associated virus (AAV) and selected promoters, reference is made to Klein et al, 1998, Experimental Neurology 150:183 194, "Neuron-Specific Transduction in the Rat Septohippocampal or Nigrostriatal Pathway by Recombinant Adeno-associated Virus Vectors".

With respect to a method of gene therapy using recombinant AAV with significant persistence through stable expression of the neurotrophic factors NGF, GDNF, BDNF, and resultant neurochemically quantifiable therapeutic effects, reference is made to Klein et al, Neuroscience 90:815 821, "Long-term Actions of Vector-derived Nerve Growth Factor or Brain-derived Neurotrophic Factor on Choline Acetyltransferase and Trk Receptor Levels in the Adult Rat Basal Forebrain."

A further important parameter is the dosage of MANF to be delivered into the target tissue. The unit dosage refers generally to the MANF/ml of MANF composition. For viral vectors, MANF concentration may be defined by the number of viral particles/ml of neurotrophic composition. Optimally, for delivery of MANF using a viral expression vector, each unit dosage of MANF will compromise 2.5 to 25 ul of MANF composition, expression vector in pharmaceutically acceptable fluid and provides from $10^{10}$ to $10^{15}$ MANF expressing viral particles per ml of MANF composition. Such high titers are particularly useful for AAV. For lentivirus, the titer is normally lower, from $10^8$ to $10^{10}$ transducing units per ml (TU/ml).

Other Medical Indications

Addiction

Drug addiction can be regarded as a pathological form of neural plasticity reflected by long lasting or permanent changes in behavior of both human beings and experimental animals. Indeed, according to most recent views drugs of abuse take control over the mechanisms involved in most well known forms of neural plasticity—learning and memory.

Neurotrophic factors regulate neural plasticity. One of them, glial cell line-derived neurotrophic factor (GDNF) that signals through GFRa1/RET receptor complex, appears to have a role in the long-lasting/persistent effects of drugs of abuse, and thus, it may play a crucial role in the regulation of drug addiction. GDNF family neurotrophic factors have effects on the plastic changes occurring during the course of repeated exposure to drugs of abuse (cocaine, morphine, amphetamine, alcohol). Since MANF has prominent effects on the dopamiergic system it is concluded that the novel neurotrophic factor, MANF may have protective effects and can be used for the treatment of drug addiction (to drugs of abuse cocaine, morphine, amphetamine, alcohol).

Pharmaceutical and Therapeutical Compositions and Formulations

The MANF nucleic acid molecules, MANF polypeptides, and anti-MANF Abs (active compounds) of the invention, and derivatives, fragments, analogs and homologs thereof, can be incorporated into pharmaceutical compositions.

Such compositions of MANF are prepared for storage by mixing MANF nucleic acid molecule, protein, or antibody having the desired degree of purity with optional physiologically acceptable carriers, excipients, or stabilizers (Remington's Pharmaceutical Sciences, 16th edition, Osol, A., Ed., (1980)), in the form of lyophilized cake or aqueous solutions, Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween, Pluronics or polyethylene glycol (PEG).

The MANF nucleic acid molecule, protein, or antibodies may also be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin micro spheres, micro emulsions, nano-particles, and nanocapsules), or in macroemulsions. Such techniques are disclosed in Remington's Pharmaceutical Sciences, supra.

The route of MANF nucleic acid molecule, protein, or antibody administration is in accord with known methods, e.g., those routes set forth above for specific indications, as well as the general routes of injection or infusion by intravenous, intraperitoneal, intracerebral, intramuscular, intraocular, intraarterial, or intralesional means, or sustained release systems as noted below. MANF nucleic acid molecule, protein, or antibody is administered continuously by infusion or by bolus injection. Generally, where the disorder permits, one should formulate and dose the MANF nucleic acid molecule, protein, or antibody for site-specific delivery. Administration can be continuous or periodic. Administration can be accomplished by a constant- or programmable-flow implantable pump or by periodic injections. The nucleic acid molecules of the invention can be inserted into vectors and used as gene therapy vectors. Gene therapy vectors can be delivered to a subject by, for example, intravenous injection, local administration (Nabel and Nabel, U.S. Pat. No. 5,328,470, 1994), or by stereotactic injection (Chen et al., Proc. Natl. Acad. Sci. USA 91:3054-3057 (1994)). The pharmaceutical preparation of a gene therapy vector can include an acceptable diluent, or can comprise a slow release matrix in which the gene delivery vehicle is imbedded.

Alternatively, where the complete gene delivery vector can be produced intact from recombinant cells, e.g., retroviral vectors, the pharmaceutical preparation can include one or more cells that produce the gene delivery system.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels as described by Langer et al., J. Biomed. Mater. Res., 15:167-277 (1981) and Langer, Chem. Tech., 12:98-105 (1982) in polyvinylalcohol, polylactides (U.S. Pat. No. 3,773,919, EP 58,481), or non-degradable ethylene-vinyl acetate (Langer et al., supra).

Sustained-release MANF compositions also include liposomally entrapped MANF nucleic acid molecule, protein, or antibodies. Liposomes containing MANF nucleic acid molecule, protein, or antibodies are prepared by methods known per se: Epstein et al., Proc. Natl. Acad. Sci. USA, 82:3688-3692 (1985); Hwang et al., Proc. Natl. Acad. Sci. USA, 77:40304034 (1980); EP 52,322; EP 36,676; EP 88,046; EP 143,949; EP 142,641; U.S. Pat. Nos. 4,485,045 and 4,544, 545; and EP 102,324. Ordinarily the liposomes are of the small (about 200-800 Angstroms) unilamellar type in which the lipid content is greater than about 30 mol % cholesterol, the selected proportion being adjusted for the optimal MANF nucleic acid molecule, protein, or antibody therapy.

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Semipermeable, implantable membrane devices are useful as means for delivering drugs in certain circumstances. For example, cells that secrete soluble MANF, chimeras or antibodies can be encapsulated, and such devices can be implanted into a patient. For example, into the brain of patients suffering from Parkinson's Disease. See, U.S. Pat. No. 4,892,538 of Aebischer et al.; U.S. Pat. No. 5,011,472 of Aebischer et al.; U.S. Pat. No. 5,106,627 of Aebischer et al.; PCT Application WO 91/10425; PCT Application WO 91/10470; Winn et al., Exper. Neurology, 113:322-329 (1991); Aebischer et al., Exper Neurology, 111:269-275 (1991); and Tresco et al., ASAIO, 38:17-23 (1992).

Accordingly, also included is a method for preventing or treating damage to a nerve or damage to other MANF-responsive cells, which comprises implanting cells that secrete MANF, its agonists or antagonists as may be required for the particular condition, into the body of patients in need thereof. Finally, the present invention includes a device for preventing or treating nerve damage or damage to other cells as taught herein by implantation into a patient comprising a semipermeable membrane, and a cell that secretes MANF (or its agonists or antagonists as may be required for the particular condition) encapsulated within said membrane and said membrane being permeable to MANF (or its agonists or antagonists) and impermeable to factors from the patient detrimental to the cells. The patient's own cells, transformed to produce MANF ex vivo, could be implanted directly into the patient, optionally without such encapsulation. The methodology for the membrane encapsulation of living cells is familiar to those of ordinary skill in the art, and the preparation of the encapsulated cells and their implantation in patients may be accomplished without under experimentation.

The present invention includes, therefore, a method for preventing or treating nerve damage by implanting cells, into the body of a patient in need thereof, cells either selected for their natural ability to generate or engineered to secrete MANF or MANF antibody. Preferably, the secreted MANF or antibody being soluble, human mature MANF when the patient is human. The implants are preferably non-immunogenic and/or prevent immunugenic implanted cells from being recognized by the immune system. For CNS delivery, a preferred location for the implant is the cerebral spinal fluid of the spinal cord.

An effective amount of MANF nucleic acid molecule, protein, or antibody to be employed therapeutically will depend, for example, upon the therapeutic objectives, the route of administration, and the condition of the patient. Accordingly, it will be necessary for the therapist to titre the dosage and modify the route of administration as required to obtain the optimal therapeutic effect. Typically, the clinician will administer the MANF protein or antibody until a dosage is reached that achieves the desired effect. A typical daily dosage for systemic treatment might range from about 1 microgram/kg to up to 10 mg/kg or more, depending on the factors mentioned above. As an alternative general proposition, the MANF nucleic acid molecule, protein, or antibody is formulated and delivered to the target site or tissue at a dosage capable of establishing in the tissue a MANF level that is efficacious but not unduly toxic. This intra-tissue concentration should be maintained if possible by continuous infusion, sustained release, topical application, MANF-expressing cell implant, or injection at empirically determined frequencies. The progress of this therapy is easily monitored by conventional assays.

The efficacy of virally-delivered or non-virally delivered MANF polynucleotides can be tested in any of a number of animal models of the Parkinson's disease, known in the art. For example, the most extensively used animal models of Parkinson's disease replicate the neurodegeneration of dopaminergic neurons usually by administration of toxins. Unilateral injection of 6-hydroxydopamine (6-OHDA) into the substantia nigra of mice or rats results in neuronal loss in the ipsilateral striatum and substantia nigra pars compacta with little change in contralateral hemisphere. Similarly, methamphetamine-induced neurotoxicity results in neurodegeneration of dopaminergic and serotoninergic neurons and is considered by those of skill in the art to be closely aligned to the human condition. Efficacy of a therapeutic agent may be evaluated by behavioral outcome using the apomorphine-induced rotational behavior.

Another Parkinson's disease model is constructed using the neurotoxin N-methyl-4-phenyl-1,2,3,6,-tetrahydropyridine (MPTP). MPTP is administered to mammals, such as mice, rats, and monkeys. Administration of MPTP to monkeys results not only in loss of dopaminergic and serotoninergic neurons in substantia nigra pars compacta and striatum, but also in behavioral manifestations similar to those seen in human Parkinson's disease patients, such as akinesia and rigid posture. See, e.g., U.S. Pat. No. 6,362,319, incorporated herein by reference in its entirety.

In contrast to the above-described animal models of Parkinson's disease, a number of inbred strains of mice are available which demonstrate a gradual decline in dopaminergic cell numbers. For example, a D2 receptor-deficient mouse has been generated by homologous recombination whose behavioral characteristics resemble those of patients afflicted with Parkinson's disease. Fitzgerald et al. (1993) Brain Res. 608:247-258. A second example is the weaver mutant mouse which shows a gradual decline in mesenchephalic dopaminergic neuron numbers over time up to 40%. Verina et al. (1997) Exp. Brain Res. 113:5-12; Adelbrecht et al. (1996) Mol. Brain. Res. 43:291-300; Mitsumoto et al. (1994) Science 265:1107-1110.

The present examples used the Sauer and Oertel partial PD model (Sauer and Oertel, Neuroscience (1994) 59:401-415). In this model, intrastriatal injection of 6-OHDA induces progressive retrograde degeneration of DA neurons that starts between 1 to 2 weeks after lesioning and continues over 8 to 16 weeks. This ongoing depletion of DA neurons may be more similar to the disease process of PD and more appropriate as an animal model for therapeutic study than the complete model, which is constructed by destroying the medial forebrain bundle, thereby causing more rapid degeneration of DA neurons. In the experiments detailed below, rats had exhibited consistent behavioral deficits before vector injection. The appearance of apomorphine-induced rotations is generally assumed to represent ~90% depletion of striatal dopamine content (Hudson et al., Brain Res. (1993) 626:167-174). However, studies on PD patients and animal models have indicated that there might be more surviving DA neurons than the levels of dopamine suggested (Javoy-Agid et al., Neuroscience (1990) 38:245-253; Feamley and Lees, Brain (1991) 114:2283-2301; Schulzer et al., Brain (1994) 117:509-516). In the model used herein, the number of CTB-positive neurons on the lesioned side of SN was 28.9% of contralateral value at 4 weeks post-lesion. This is consistent with previous studies using Fluorogold (FG)-retrograde labeling that demonstrated 28.8% (35 days post-lesion) (Kozlowski et al., Exp. Neurol, (2000) 166:1 15) or 34% (4 weeks post-lesion) (Sauer and Oertel, Neuroscience (1994) 59:401-415) of FG-positive cells in the lesioned SN. In addition, most CTB-labeled neurons were TH-positive, suggesting that part of the nigrostriatal projection remained intact at the time of AAV vector injection. Without being bound by a particular theory, these remaining portions of intact nigrostriatal projections and DA neurons may serve as substrate for regeneration and functional recovery after MANF gene delivery.

Animal models of other neurodegenerative diseases have been described and are useful for evaluating the therapeutic efficacy of virally-delivered MANF polynucleotides in the treatment of neurodegenerative disorders in addition to PD. For example, Martin et al. (1995) Brain Res. 683:172-178 describe an animal model of epilepsy, Matheson et al. (1997) NeuroReport 8:1739-1742 and Oppenheim et al. (1995) Nature 373:344-346 describe models of neurodegeneration that results from physical trauma, and Sagot et al. (1996) J. Neurosci. 16:2335-2341 describe a model of motor neuron degeneration in animals.

Diagnostics

The invention also features diagnostic or prognostic kits for use in detecting the presence of MANF or allelic variant thereof in a biological sample. The kit provides means for the diagnostics of MANF dependent conditions as described hereinabove or for assessing the predisposition of an individual to conditions mediated by variation or dysfunction of MANF. The kit can comprise a labeled compound capable of detecting MANF polypeptide or nucleic acid (e.g. mRNA) in a biological sample. The kit can also comprise nucleic acid primers or probes capable of hybridising specifically to at least of portion of an MANF gene or allelic variant thereof. The kit can be packaged in a suitable container and preferably it contains instructions for using the kit.

Purification of Receptor

In yet another aspect of the invention, the MANF or MANF analog may be used for affinity purification of receptor that binds to the MANF. MANF is a preferred ligand for purification. Briefly, this technique involves: (a) contacting a source of MANF receptor with an immobilized MANF under conditions whereby the MANF receptor to be purified is selectively adsorbed onto the immobilized MANF; (b) washing the immobilized MANF and its support to remove non-adsorbed material; and (c) eluting the MANF receptor molecules from the immobilized MANF to which they are adsorbed with an elution buffer. In a particularly preferred embodiment of affinity purification, MANF is covalently attaching to an inert and porous matrix or resin (e.g., agarose reacted with cyanogen bromide). Especially preferred is a MANF immunoadhesin immobilized on a protein-A column. A solution containing MANF receptor is then passed through the chromatographic material. The MANF receptor adsorbs to the column and is subsequently released by changing the elution conditions (e.g. by changing pH or ionic strength).

The preferred technique for identifying molecules which bind to the MANF utilizes a chimeric MANF (e.g., epitope-tagged MANF or MANF immunoadhesin) attached to a solid phase, such as the well of an assay plate. The binding of the candidate molecules, which are optionally labelled (e.g., radiolabeled), to the immobilized MANF can be measured.

Production of Transgenic Animals

Nucleic acids which encode MANF, preferably from non-human species, such as murine or rat protein, can be used to generate either transgenic animals or "knock out" animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic, stage. A transgene is a DNA which is integrated into the genome of a cell from which a transgenic animal develops. In one embodiment, the human and/or mouse cDNA encoding MANF, or an appropriate sequence thereof, can be used to clone genomic DNA encoding MANF in accordance with established techniques and the genomic sequences used to generate transgenic animals that contain cells which express DNA encoding MANF. Methods for generating transgenic animals, particularly animals such as mice, have become conventional in the art and are described, for example, in U.S. Pat. Nos. 4,736,866 and 4,870,009. Typically, particular cells would be targeted for MANF transgene incorporation with tissue-specific enhancers, which could result in desired effect of treatment. Transgenic animals that include a copy of a transgene encoding MANF introduced into the germ line of the animal at an embryonic stage can be used to examine the effect of increased expression of DNA encoding MANF. Such animals can be used as tester animals for reagents thought to confer protection from, for example, diseases related to MANF. In accordance with this facet of the invention, an animal is treated with the reagent and a reduced incidence of the disease, compared to untreated animals bearing the transgene, would indicate a potential therapeutic intervention for the disease.

It is now well-established that transgenes are expressed more efficiently if they contain introns at the 5' end, and if these are the naturally occurring introns (Brinster et al. Proc. Natl. Acad. Sci. USA 85:836-840 (1988); Yokode et al., Science 250:1273-1275 (1990)).

Transgenic offspring are identified by demonstrating incorporation of the microinjected transgene into their genomes, preferably by preparing DNA from short sections of tail and analyzing by Southern blotting for presence of the transgene ("Tail Blots"). A preferred probe is a segment of a transgene fusion construct that is uniquely present in the transgene and not in the mouse genome. Alternatively, substitution of a natural sequence of codons in the transgene with a different sequence that still encodes the same peptide yields a unique region identifiable in DNA and RNA analysis. Transgenic "founder" mice identified in this fashion are bred with normal mice to yield heterozygotes, which are back-crossed to create a line of transgenic mice. Tail blots of each mouse from each generation are examined until the strain is established and homozygous. Each successfully created founder mouse and its strain vary from other strains in the location and copy number of transgenes inserted into the mouse genome, and hence have widely varying levels of transgene expression. Selected animals from each established line are sacrificed at 2 months of age and the expression of the transgene is analyzed by Northern blotting of RNA from liver, muscle, fat, kidney, brain, lung, heart, spleen, gonad, adrenal and intestine.

Production of "Knock Out" Animals

Alternatively, the non-human homologs of MANF can be used to construct a MANF "knock out" animal, i.e., having a defective or altered gene encoding MANF, as a result of homologous recombination between the endogenous MANF gene and an altered genomic MANF DNA introduced into an embryonic cell of the animal. For example, murine MANF cDNA can be used to clone genomic MANF DNA in accordance with established techniques. A portion of the genomic MANF DNA can be deleted or replaced with another gene, such as a gene encoding a selectable marker which can be used to monitor integration. Typically, several kilobases of unaltered flanking DNA (both at the 5' and 3' ends) are included in the vector (see e.g., Thomas and Capecchi, Cell 51:503 (1987) for a description of homologous recombination vectors). The vector is introduced into an embryonic stem cell line (e.g., by electroporation) and cells in which the introduced DNA has homologously recombined with the endogenous DNA are selected (see e.g., Li et al., Cell 69:915 (1992)). The selected cells are then injected into a blastocyst of an animal (e.g., a mouse) to form aggregation chimeras (see e.g., Bradley, in Teratocarcinomas and Embryonic Stem Cells: A Practical Approach, E. J. Robertson, ed. (IRL, Oxford, 1987), pp. 113-152). A chimeric embryo can then be implanted into a suitable pseudopregnant female foster animal and the embryo brought to term to create a "knock out" animal. Progeny harbouring the homologously recombined DNA in their germ cells can be identified by standard techniques and used to breed animals in which all cells of the animal contain the homologously recombined DNA. Knock-out animals can be characterized for their ability to mimic human neurological disorders and defects.

EQUIVALENTS

Although particular embodiments have been disclosed herein in detail, this has been done by way of example for purposes of illustration only, and is not intended to be limiting with respect to the scope of the appended claims that follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims.

Having generally described the invention, the same will be more readily understood by reference to the following examples, which are provided by way of illustration and are not intended as limiting.

EXAMPLES

Example 1

Materials and Methods

Cloning and Expression Analysis by RT-PCR.

Full-length MANF cDNA from human and mouse was cloned by RT-PCR (reverse transcription polymerase chain reaction). Human RNAs of peripheral and total brain tissues were obtained from Clontech (Mountain View, Calif.). RNAs from post-mortem human brain regions and mouse total RNAs were isolated using Ambion's RNAwiz reagent (Applied Biosystems, Austin, Tex.). First strand cDNAs were synthesized with Superscript[II] reverse transcriptase (Invitrogen, Carlsbad, Calif.) according manufacturer's recommendations using oligo(dT) primed total RNA (5 μg) or poly(A)$^+$ RNA (1 μg) from different tissues as a template. Primers used for PCR were hMANF-ATG2,
5'-ACCATGTGGGCCACGCAGGGGCT-3' (SEQ ID NO: 10) and hMANF-stop-del,
5'-CAAATCGGTCGGTGCACTGGCTG-3' (SEQ ID NO: 11) (for human MANF);
mManf-ATG, 5'-ACCATGTGGGCTACGCGCGGGCT-3' (SEQ ID NO: 12) and mManf-stop-del,
5'-CAGATCAGTCCGTGCGCTGGCTG-3' (SEQ ID NO: 13) (for mouse Manf).
PCR reactions for human and mouse MANF were performed using Expand™ High Fidelity PCR system (Roche Molecular Biochemicals, Basel, Switzerland), according manufacturer's instructions in a reaction volume of 25 μl and with 1/20 of the reverse transcriptase reaction as a template. PCR conditions were the following: 94° C. (2 min); 15 cycles of 94° C. (30 s), 60° C. (30 s), 72° C. (30 s) and additional 20 cycles with extension time 30 s+5 s/cycle. Amplified PCR products were resolved on 1.2% agarose gel. PCR products were cloned into pCR11 (Invitrogen) and sequenced.

Transient Protein Expression.

COS-7 or HEK 293T cells were transiently transfected with human MANF in pcDNA3.1-V5-His (Invitrogen) or with pEGFP-C1 (Clontech) as described (Lindholm et al., 2007). Protein samples from cells and culture supernatants were resolved in 15% SDS-polyacrylamide gel electrophoresis (SDS-PAGE), and analyzed by western blotting with rabbit polyclonal anti-MANF antibodies (1:1000) and enhanced chemiluminescence (ECL) detection method (Amersham, Buckinghamshire, UK). For amino-terminal sequencing and mass analysis, Ni-affinity chromatography (see below) was used to purify recombinant MANF protein with carboxy-terminal V5 and His tags secreted by transiently transfected COS-7 cells.

Protein Production in Sf9 Cells.

A cDNA encoding MANF was cloned into pMIB vector (InsectSelect System; Invitrogen) with carboxy-terminal V5 and His tags, and a stable polyclonal Sf9 cell-line secreting MANF protein was established according to the manufacturer's instructions. MANF was purified from the culture supernatant using Ni-affinity chromatography. The supernatant was adjusted to pH 7.4 with PBS containing 5 mM imidazole and incubated with Ni$^{2+}$-charged Chelating Sepharose Fast Flow (Amersham) for 1 h at +4° C. The matrix was washed with 0.3 M KCl in PBS, and protein was eluted with 0.5 M imidazole in PBS, pH 7.4. The sample was concentrated with Centricon YM-10 devices (Millipore, Billerica, Mass.). Cation exchange chromatography was used for further purification. The sample was diluted in 40 mM Na-phosphate buffer, pH 6.0, and applied on a Resource S column (1 ml, Amersham). MANF protein was eluted with 0-1 M NaCl gradient in 40 mM Na-phosphate buffer, pH 7.5. MANF was concentrated, and the buffer was simultaneously changed to PBS.

Protein Production in E. Coli.

We cloned the MANF open reading frame, excluding the region encoding the signal peptide, into a T7lac based vector containing a His-tag fusion (Peränen et al., 1996; Peränen and Furuhjelm, 2001). The vector was transformed into Origami B (Novagen, Darmstadt, Germany) cells, and the protein was expressed in the presence of IPTG for 3 h at 37° C. The cells were lysed in A-buffer (20 mM Tris HCl pH 8.0, 0.5% Triton X-100, 0.4 mM PMSF) by sonication. Then NaCl and imidazole were added to final concentration of 0.5 M and 0.02M respectively. After centrifugation (15.000×g, 15 min at 4° C.) the supernatant was passed through a 0.45 μM filter. The MANF protein was purified by the HisTrap kit according to the manufacturer (GE Healthcare, Buckinghamshire, UK). After purification the buffer of the eluted protein was exchanged (20 mM phospahate buffer pH 8.0, 150 mM NaCl) by a PD-10 column. The His-tag was cleaved by AcTEV (Invitrogen), and the cleaved products were passed through the HiTrap Chelating column to get rid of the tag, and the cleaved MANF was obtained in the flow through. MANF was finally passed through a HiTrap Q column to get rid of small contaminants of the AcTEV and His-tag. MANF was then concentrated by Amicon Ultra-4 filter device (Millipore), and the buffer was simultaneously changed to PBS. Aliquots of MANF were stored at −80° C.

N-Terminal Sequencing and Mass Spectrometry.

MANF proteins produced in COS-7, E. coli or Sf9 cells were purified and applied to reversed phase chromatography in a 1×20 mm TSKgel TMS250 (C1, 10 μm, 250 Å, Toso-Haas, Tokyo, Japan). Elution was performed with a linear gradient of acetonitrile (0-100% in 60 min) in 0.1% trifluoroacetic acid using a flow rate of 50 μl/min. MANF proteins were collected and subjected to amino-terminal sequence analysis in a Procise 494A Sequencer (Perkin Elmer, Waltham, Mass.). For electrospray mass spectrometry, a Q-TOF instrumet (Micromass Ltd., Manchester, UK) externally and internally calibrated with horse myoglobin (16952.0 Da) was used. Following trypsin digestion, peptide mass fingerprint analysis was performed with an Ultraflex TOF/TOF (Bruker Daltonik GmbH, Bremen, Germany) matrix-assisted laser desorbtion/ionization time-of-flight (MALDI-TOF) mass spectrometer as described (Poutanen et al., 2001).

Northern Hybridization.

Mouse Manf DNA probe was generated by random priming with Rediprime II system and Redivue dCTP-$^{32}$P (Amersham). Unbound radioactivity was removed with Illustra NICK column (GE Healthcare). Labelled Manf probe was diluted in hybridization buffer (50% formamide, 5×SSC, 1×Denhardt's, 0.3% SDS, 100 μg/ml herring sperm DNA) at activity of 2.5×10$^6$ cpm/ml and hybridized on a MTN mouse tissue blot (BD Biosciences, Franklin Lakes, N.J.) at 42° C. over night. After hybridization, the blot was washed with 2×SSC, 0.1% SDS at 65° C. The hybridization signal was detected using a BAS-III imaging plate (Fujifilm, Tokyo, Japan) together with BAS-1500 imaging system and TINA software.

In Situ Hybridization and Image Analysis.

Full-length cDNA encoding mouse Manf (GenBank Acc. No. NM_029103, nucleotides 41-577) in pCRII was used to prepare antisense and control-sense cRNA probes. Plasmid was linearized with selected enzymes, and probes were synthesized by in vitro transcription using $^{35}$S-labelled UTP (Amersham) and SP6 or T7 in vitro transcription system (Promega, Madison, Wis.). Coronal sections (14 μm) from fresh frozen postnatal (P1, P10) and adult NMRI mice brain, or embryonic mouse paraffin sections (8 μm) were analyzed by in situ hybridization as described earlier (Reeben et al., 1998). Hybridization and washing temperatures were 52° C. and 65° C. for high stringency, respectively. The sections were dipped in NTB-2 emulsion (Kodak Nordic, Upplands Vasby, Sweden), developed after 5 days and counterstained with haematoxylin. Dark-field and bright-field images were obtained with Olympus BX61 microscope (Olympus, Tokyo, Japan) and AnalySIS software. Adobe Photoshop was used for image processing. For SE and ischemia studies, brains were frozen on powdered dry ice, and 12 μm thick coronal sections were made on cryostat. In situ hybridization was performed as described above. Analysis of optical densities was made by image analysis program ImageJ Image 1.34 (Processing and Analysis in Java developed at the National Institutes of Health). Gray levels for standards were used in third-degree polynomial calibration to obtain equivalent values of tissue radioactivity (nCi/g).

Antibody Production and Specificity.

Purified MANF from *E. coli* was used for the immunization of two rabbits as previously described (Peranen and Furuhjehn, 2001). The antiserum was affinity purified by using recombinant MANF coupled to CNBr Sepharose (Amersham) beads (Peranen and Furuhjelm, 2001). Specificity of affinity purified MANF antibodies was evaluated in western blotting and immunohistochemistry by preincubating the affinity purified antibody with recombinant MANF. For western blotting, MANF antibodies (1:1000 in 5% non-fat milk, 0.1% Tween 20 in TBS) were pre-incubated with human MANF (20 μg/ml) or mouse CDNF protein (20 μg/ml), respectively, at +4° C. overnight before applied on western blots. For immunohistochemistry, MANF antibodies were pre-incubated with human MANF protein (2 μg/ml) in 3% normal goat serum, 0.2% Triton X-100 in PBS overnight before applied on histological sections.

Tissue Protein Extracts.

Protein extracts from fresh frozen tissue samples collected from adult NMRI or C57BL/6 mice were prepared as previously described (Lindholm et al., 2007). Samples were resolved in 15% SDS-PAGE, blotted, and analyzed with rabbit anti-MANF (1:1000) or mouse anti-actin AC-40 (1:1000; Sigma-Aldrich, St. Louis, Mo.) antibodies.

Immunohistochemistry.

Adult NMRI mice were transcardially perfused with 4% paraformaldehyde (PFA). Brains were dissected, post-fixed overnight with 4% PFA at +4° C., dehydrated in ascending series of ethanol, cleared in xylene, embedded in paraffin, and sectioned at 8 μm in coronal or sagittal plane. Dissected brains of postnatal mice (P1, P10), dissected mouse embryonic heads (E17) or whole mouse embryos (E13, 17) were fixed with 4% PFA overnight at +4° C. Dissected brains of embryonic mice (E14, E16) were fixed with 4% PFA for 4 h at +4° C. Embryonic and postnatal brains were sectioned at coronal, embryonic heads at transverse and whole embryos at sagittal plane, respectively. For antigen retrieval, deparaffinized sections were microwaved in boiling citrate buffer, pH 6.0, for 10 min. Sections were stained with anti-MANF antibodies (1:100) using Vectastain Elite ABC Kit (Vector Laboratories, Burlingame, Calif.) and 3,3'-diaminobenzidine (DAB). Adult brain sections were counterstained with cresyl violet.

Induction of Globalforebrain Ischemia.

Procedures in the ischemia and status epilepticus experiments (see below) were conducted according to national guidelines and approved by the Malmö-Lund Ethical Committee for the use and care of laboratory animals. Twenty male Wistar rats (Taconic M&B A/S) weighing 280 to 290 g at the time of the ischemic insult were housed under 12-hour light/12-hour dark conditions with ad libitum access to food and water. After fasting overnight, animals were anaesthetized by inhalation of 3.5% halothane, intubated and then artificially ventilated with 1-2% halothane in $N_2O:O_2$ (70: 30). The tail artery and vein were cannulated for blood sampling and pressure recording, and drug infusion, respectively. A rectally placed thermometer was used to measure body temperature, which was maintained around 37° C. by a heating pad. The common carotid arteries were isolated. Fifty IU of heparin were then administered, the halothane concentration was decreased to 0.5%, and vecuronium bromide (Organon Teknika B.V., Boxtel, Holland) was infused intravenously at 2 mg/h as muscle relaxant. A steady state period of 30 min followed during which physiologic parameters and electroencephalogram (EEG) were monitored. Ischemia was induced by bilateral occlusion of the common carotid arteries combined with hypotension (arterial blood pressure 40-50 mm Hg) achieved by blood withdrawal from the jugular vein (Smith et al., 1984). Circulation was restored after 10 min by reinfusion of blood and removal of the occluding clasps. In the immediate recirculation period, sodium bicarbonate (0.5 ml intravenously, 50 mg/ml) was given to prevent systemic acidosis. Animals were decapitated at 2 and 24 h and 1 week after reperfusion (n=4 for each group). Sham-operated animals (n—6) were treated identically, but the common carotid arteries were not occluded.

Induction of Status Epilepticus.

Twenty-four Sprague-Dawley rats (B&K Universal, Stockholm, Sweden), weighing 220-250 g at the beginning of the experiments, were anaesthetized with halothane and implanted with a twisted insulated stainless-steel stimulating and recording electrode (Plastics One, Roanoke, Va.) unilaterally into the ventral hippocampal CA1-CA3 region (coordinates: 4.8 mm caudal and 5.2 mm lateral to bregma, 6.3 mm ventral to dura, toothbar at −3.3 mm). Ten days following electrode implantation, 18 rats were subjected to electrically induced status epilepticus (SE) as originally described by (Lothman et al., 1989). Rats received 1 h of suprathreshold stimulation consisting of 10 s trains of 1 ms biphasic square wave pulses at a frequency of 50 Hz. The stimulation was interrupted every 10 min for 1 min to allow for EEG recording and measurement of after discharges (MacLab; AD Systems, Hastings, UK). After ending the stimulation, all rats exhibited self-sustained, continuous ictal hippocampal EEG activity, which was associated with varying severity of motor behavioral convulsions, categorized into partial and generalized seizures (Racine, 1972). Both behavioral convulsions and ictal EEG activity were arrested in all rats with pentobarbital (40 mg/kg i.p.) at 2 h after stimulation offset. Animals were decapitated at 2 and 24 h and 1 week after the end of SE. Animals with focal and generalized SE profile (Mohapel et al., 2004) were randomly distributed between the groups. Control animals were not electrically stimulated, but otherwise handled in the same way as the experimental ones.

Statistical Analysis.

Comparisons were performed using one-way analysis of variance (ANOVA) followed by post-hoc Bonferroni-Dunn or test. Data are presented as means 1 SEM, and differences are considered significant at $p<0.05$. All statistical analyses were conducted using StatView software, version 5.0.1 (Abacus Concepts, Berkeley, Calif.).

Results

MANF is a Secreted Protein with Intramolecular Disulfide Bridges

We cloned full-length cDNA encoding human and mouse MANF from liver and brain, respectively, by RT-PCR. Based on sequence analysis, human MANF amino acid sequence (SwissProt Acc. No. P55145) was 98% homologous with mouse (GenBank Acc. No. NP_083379), 82% with *Xenopus laevis* (Genbank Acc. No. AAH82888) 72% with zebrafish *Danio rerio* (GenBank Acc. No. AAI24317) and 50% with *Caenorhabditis elegans* MANF protein (GenBank Acc. No. NP_500273), respectively (FIG. 1A, Table 1). It is important to notice that human MANF (ARMET) sequences submitted to the GenBank (for example, Acc No. AAI13589) still contain parts of the arginine-rich region, which is apparently not translated in vivo (Petrova et al., 2003).

In order to verify that MANF is a secreted protein, a cDNA encoding human MANF was subcloned into a mammalian expression vector and transiently transfected to human embryonic kidney HEK293T cells. Based on western analyses, native human MANF was efficiently secreted from the cells (FIG. 16). In accordance, MANF was also secreted from African green monkey kidney COS-7, mouse embryonic motoneuron hybrid MN1 and human neuroblastoma Neuro 2A cells (data not shown). Similar results were obtained with mouse Manf cDNA transfected cells (data not shown). Next, we affinity purified recombinant human MANF protein containing carboxy-terminal V5 and His tags (hMANF-V5-His) from the culture medium of transiently transfected COS-7 cells and subjected it to amino-terminal sequencing and electrospray-ionization-mass spectrometry (ESI-MS) analysis. The amino-terminal sequence of human MANF was determined as LRPGDXEVXI . . . (SEQ ID NO: 14), which verified a signal peptide cleavage site after amino acid 21 (alanine; FIG. 1A). Positions X in the determined sequence corresponds to cysteine residues in the MANF sequence and can not be detected by Edman degradation from the non-alkylated sample. After the signal sequence cleavage, mature, native human MANF consists of 158 amino acids (FIG. 1B). In electrospray mass spectrometry, hMANF-V5-His secreted from COS-7 cells gave a mass of 23194.0 Da which is 4 Da less than the average mass (23198.0 Da) calculated from the amino acid sequence. This suggests the presence of two disulfide bridges in the protein and also indicates that MANF secreted from COS-7 cells was not glycosylated.

We used an *E. coli* expression system to produce recombinant human MANF protein in higher amounts (FIG. 1D). The molecular mass of this protein, as determined by ESI-MS, was 8 Da lower than the mass calculated from the amino acid sequence, suggesting the presence of four intramolecular disulfide bridges. We also created a Sf9 insect cell line stably transfected with a cDNA encoding human MANF with carboxy-terminal V5 and His tags (FIG. 1E). ESI-MS analysis of the MANF protein secreted from Sf9 cells suggested that this protein had four intramolecular disulfide bridges and was not glycosylated. The purified MANF proteins were also subjected, after SDS-PAGE, to identification by in-gel digestion and peptide mass fingerprint analysis by MALDI-TOF MS.

Figure 2:
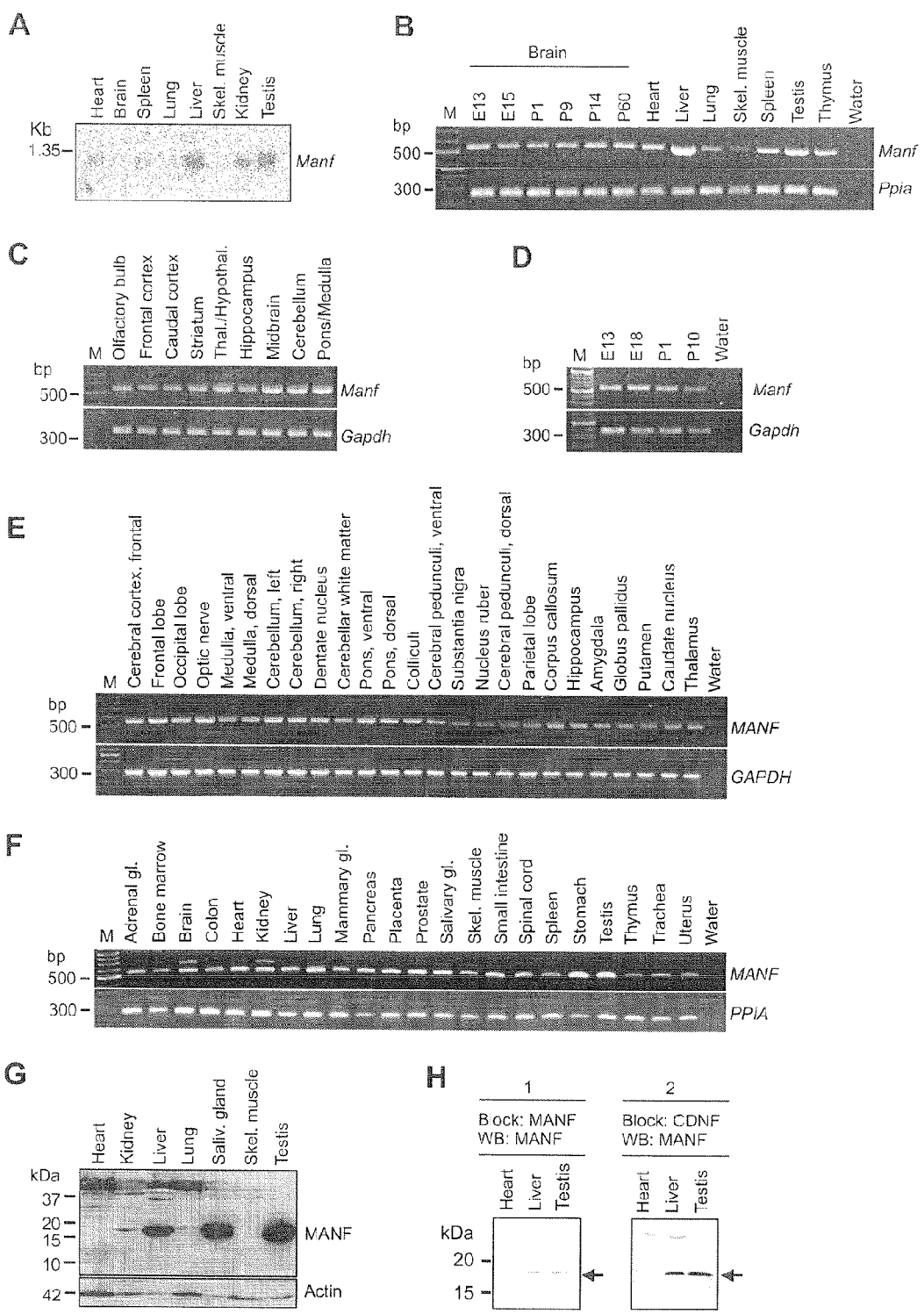
FIG. 2. MANF mRNA and protein expression in brain and non-neuronal tissues. A, Northern blot analysis of Manf mRNA expression in adult mouse tissues. A single transcript (approximate size 1.1 kb) was detected. B, RT-PCR analysis of Manf mRNA expression in developing mouse brain and in adult mouse non-neuronal tissues. C, RT-PCR analysis of Manf transcripts in adult mouse brain regions; D, in mouse embryonic and postnatal midbrain. E, RT-PCR analysis of human MANF mRNA expression in adult brain regions; F, in adult non-neuronal tissues. G, Western blot analysis of MANF protein in adult mouse tissues. The blot was re-probed with antibodies to actin. H, MANF antibodies specifically recognize MANF protein by western blotting. Panel 1: MANF antibodies pre-incubated with MANF protein. Only weak MANF signal (an arrow) was detected in the liver and testis extracts of adult mouse. Panel 2: MANF antibodies pre-incubated with CDNF protein. MANF is clearly visible in the liver and testis extracts. E, embryonic day; P, postnatal day; M, 100 bp DNA ladder. Samples in B-F contain equal levels of PPIA or GAPDH transcripts.

Widespread Distribution of Manf in RNA in the Brain and Non-Neuronal Tissues of Mouse and Human First, we used northern hybridization and RT-PCR to analyze Manf mRNA expression in developing and adult mouse tissues (FIGS. 2A-D). Northern analysis revealed differential expression of a single, 1.1 kb Manf transcript (FIG. 2A) in adult mouse tissues. High levels of Manf mRNA were detected in the adult mouse liver and testis as compared with low levels of Manf in the brain, lung and skeletal muscle. Manf mRNA was also detected in the kidney, heart and spleen. In accordance with the northern hybridization, RT-PCR analysis detected high levels of Manf transcripts in the adult mouse liver and testis, and low levels in the skeletal muscle (FIG. 2B). In the brain, Manf expression was found in all embryonic and postnatal stages studied (FIG. 2B), and in all adult brain regions analyzed, including the striatum and midbrain (FIG. 2C) and in developing midbrain (FIG. 2D). We also studied the expression of MANF transcripts in adult human brain regions (FIG. 2E) and in several adult non-neuronal tissues (FIG. 2F) by RT-PCR, Human MANF mRNA was detected in all tissues analyzed, which resembled the expression of Manf transcripts observed in mouse tissues.

Next, we raised polyclonal antibodies against human MANF and studied the expression of MANF protein in mouse tissues by western blotting. In accordance with the obtained mRNA expression data, high levels of MANF protein were detected in the adult liver, testis and salivary gland (FIG. 2G). MANF antibodies specifically recognized MANF but not the homologous CDNF protein in adult mouse tissue extracts (FIG. 2B), which confirmed the specificity of MANF antibodies.

Figure 1:
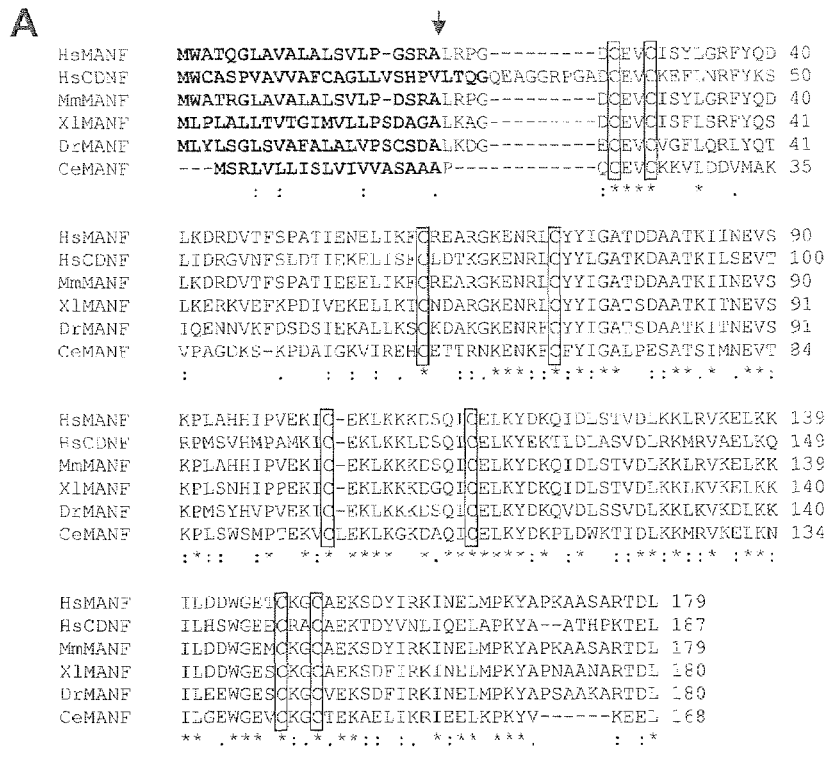
FIG. 1. Characterization and purification of MANF protein. A, Alignment of MANF and CDNF amino acid sequences from selected organisms (SEQ ID NOS: 2, 5-9, respectively). Eight conserved cysteine residues with similar spacing are boxed. The experimentally determined signal sequence cleavage site in human MANF is indicated by an arrow. Hs, *Homo sapiens*; Mm, *Mus musculus*; Xl, *Xenopus laevis*; Dr, *Danio rerio*; Ce, *Caenorhabditis elegans*. B, Schematic illustrations of human MANF protein. Pre indicates the signal sequence. Cysteines are shown by black bars, and relative numbers of amino acids are shown. C, Western blot showing secretion of native human MANF (calculated molecular mass 18 kpa) protein from transiently transfected HEK 293T cells. Cell lysate (C) and culture medium (M) were applied on 15% SDS-PAGE, blotted, and analyzed with antibodies to MANF. Cells transfected with EGFP cDNA were analyzed as a control. D, Recombinant human MANF protein produced in *E. coli*. Protein was applied on 15% SDS-PAGE and stained with Coomassie stain. Lane 1, molecular weight marker; lane 2, purified MANF (2 μg). E, Recombinant human MANF protein with V5 and His tags (calculated molecular mass 22 kDa) produced in Sf9 cells. Lane 1, molecular weight marker, lane 2, purified MANF protein (5 μg).
Figure 1:
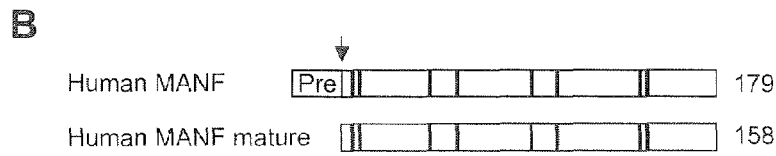
Figure 1:
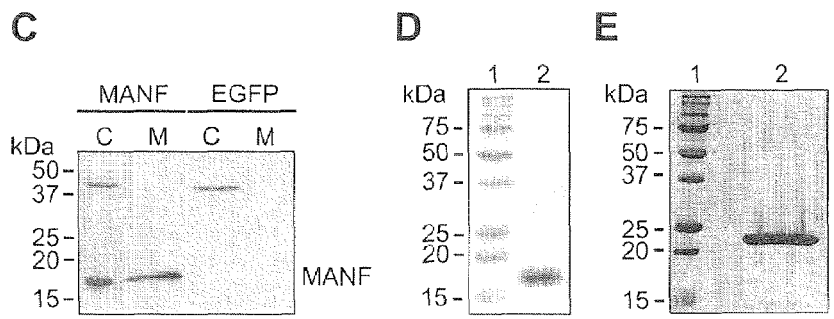
Figure 3:
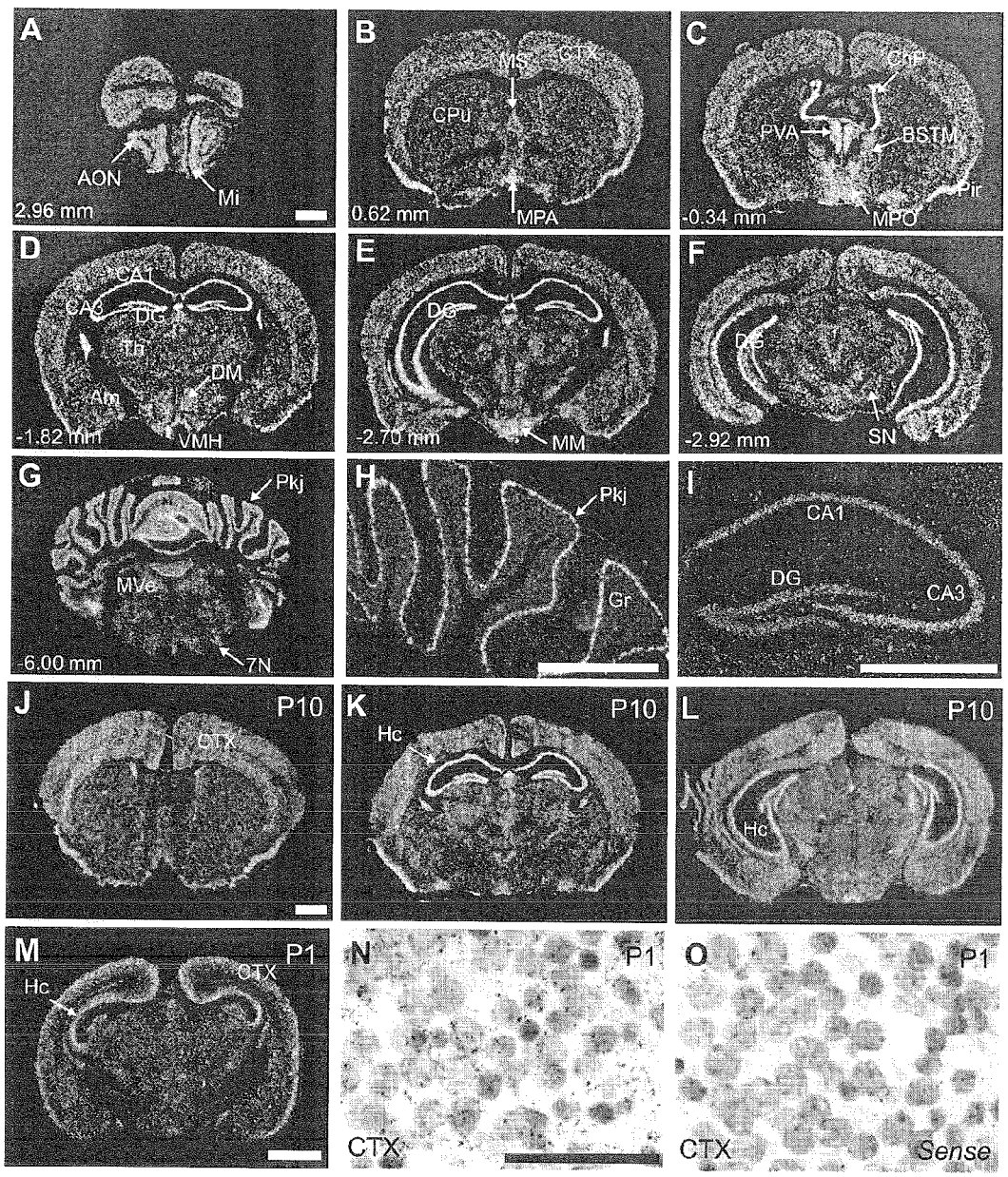
FIG. 3. In situ hybridization analysis of Manf mRNA expression in the adult (A-I), postnatal P10 (J-L) and postnatal P1 (M-O) mouse brain. A-M, Dark-field autoradiographs of coronal sections hybridized with $^{35}$S-labelled Manf CRNA probe. N. Bright-field autoradiograph showing Manf silver grains in the cerebral cortex of P1 mouse brain. O, Parallel section for (N) hybridized with $^{35}$S-labelled control-sense cRNA probe. Am, Amygdala; AON, anterior olfactory nucleus; BSTM, bed nucleus of stria terminalis; CA1 and CA3; pyramidal layers in hippocampus, CPu, caudate putamen; CTX, cerebral cortex; ChP, choroid plexus; DG, dentate gyrus; DM, dorsomedial hypothalamic nuclei; Gr, granular layer; GrO, granular layer of olfactory bulb; Hc, hippocampus; Mi, mitral cell layer of olfactory bulb; MM, medial mammillary nucleus; MPA, medial preoptic area; MPO, medial preoptic nucleus; MS, medial septal nucleus; MVe, medial vestibular nucleus; Pir, piriform cortex; Pkj, Purkinje cell layer of cerebellum; PVA, paraventricular thalamic nuclei, anterior; SN, substantia nigra; Th, thalamus; VMH, ventromedial hypothalamic nucleus; 7N, facial nucleus. In (A-G), shown are distances from Bregma (mm). Scale bar 1 mm in (A-M); 50 μm in (N-O).
Figure 4:
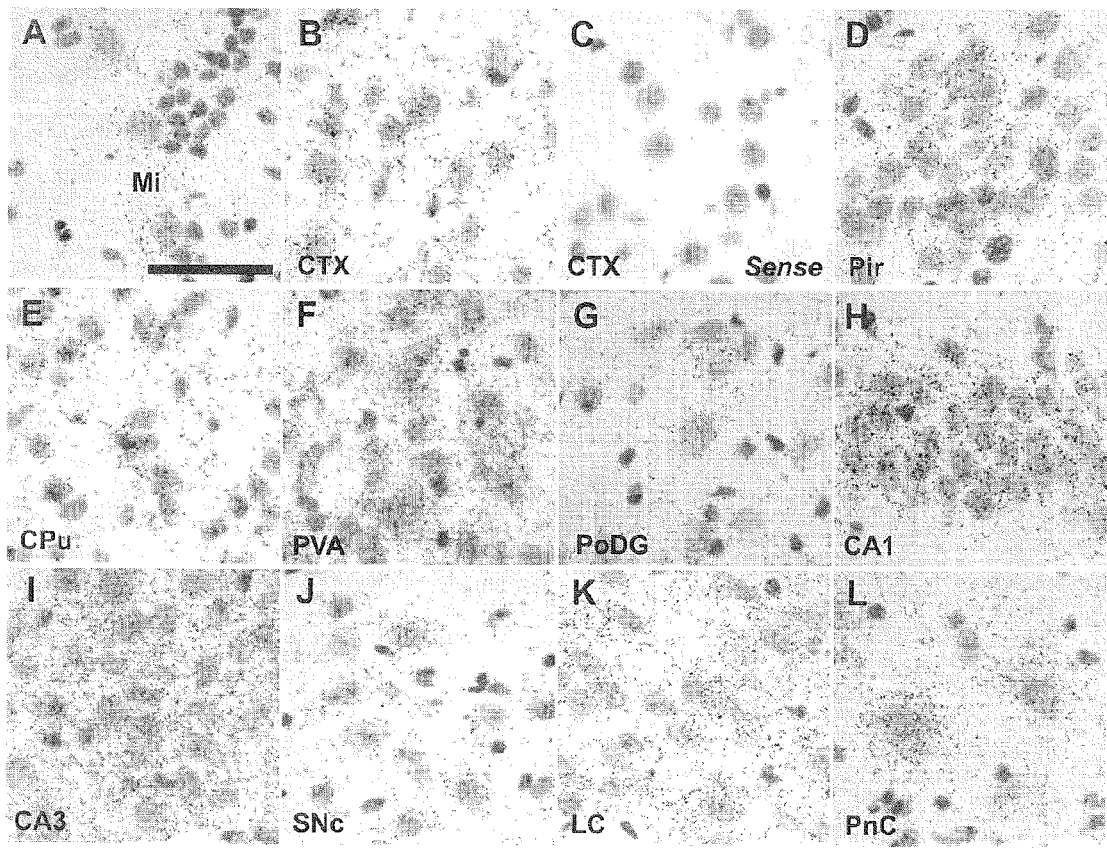
FIG. 4. Cellular localization of Manf mRNA in the adult mouse brain shown in bright-field in situ hybridization microphotographs. A, Manf signal in the mitral cell layer of the olfactory bulb (Mi); B, layer IV of cerebral cortex (CTX). C, Section hybridized with $^{35}$S-labelled control-sense cRNA probe. Shown are cells from the cerebral cortex as in (B). D, Manf signal in piriform cortex (Pir); E, caudate putamen (dorsal striatum; CPu), F, paraventricular thalamic nucleus (PVA), G, polymorphic layer of dentate gyrus (PoDG); H, CA1 layer of hippocampus; I, CA3 layer of hippocampus; J, substantia nigra compacta region (SNc); K, locus coeruleus (LC); L, pontine reticular nucleus, caudal part (PnC). Scale bar 50 μm.

We used in situ hybridization analysis to study the cellular localization of Manf mRNA in adult and postnatal mouse brain (FIGS. 3, 4). In the adult, widespread distribution of Manf transcripts was detected (FIG. 3A-1). Silver granules indicating Manf expression colocalized mainly with light-coloured neuronal nuclei, which were identified by haematoxylin counterstaining as compared to more dark-stained, smaller nuclei of the glial cells (FIG. 4). In the olfactory bulb, high levels of Manf mRNA were detected in the anterior olfactory nucleus and mitral cell layer (FIGS. 3A, 4A). In the cerebral cortex, Manf mRNA expression was relatively high through cortical layers II-VI (FIG. 3B, 4B). Only few background silver grains were visible in the cortical cells hybridized with the control sense cRNA probe (FIG. 4C), which confirmed the specificity of hybridization signal. Abundant Manf expression was also detected in the piriform cortex (FIGS. 3C, 4D). In the dorsal striatum (caudate putamen), moderate level of Manf mRNA signal was detected (FIGS. 3B, 4E). In thalamus, strong Manf hybridization signal was detected in the paraventricular nucleus and in bed nucleus of stria terminalis (FIGS. 3C, 4F). In the hippocampus, strong Manf-specific signal was localized in the pyramidal CA1-CA3 regions and in granular and polymorph layer of dentate gyrus (FIGS. 3D-F, 4G-I), and was especially intense in the CA3 pyramidal region (FIG. 4I). In the preoptic area and hypothalamus, Manf mRNA expression was observed in several nuclei, including preoptic nucleus (FIG. 3C), dorsomedial- and ventromedial nuclei (FIG. 3D), and in medial mammillary nucleus (FIG. 3E). Intermediate level of Manf signal was detected in the substantia nigra (FIGS. 3F, 4J). Cerebellar Purkinje cells strongly expressed Manf mRNA (FIG. 3G, H). In the pons and medulla, Manf mRNA was expressed in several regions, including the medial vestibular nucleus and facial nucleus (FIG. 3G), locus coeruleus (FIG. 4K) and pontine reticular nucleus (FIG. 4L). Furthermore, high levels of Manf transcripts were detected in the non-neuronal cells of choroid plexus (FIG. 3C). Resembling the results obtained from the adult, widespread Manf in situ hybridization signal was detected also in the brain of postnatal day 1 (P1; FIG. 3M-O) and P10 (FIG. 3J-L) mice. Especially high levels of Manf mRNA were localized in the hippocampal formation (FIG. 3K-L, M). Manf signal was relatively abundant also in the cerebral cortex (FIG. 3J, M, N). The detected hybridization signal was specific for Manf transcripts, since only weak background signal was detected in sections hybridized with control-sense cRNA probe (FIG. 3O).

Figure 5:
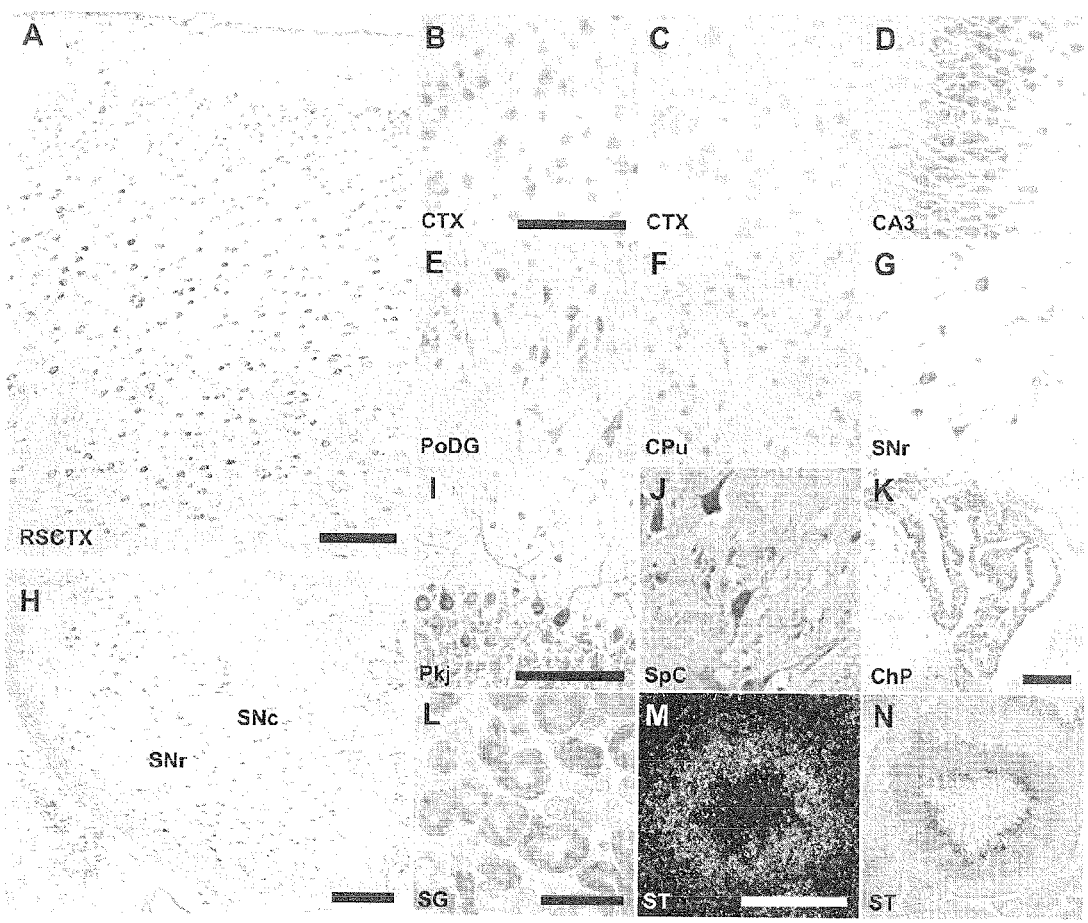
FIG. 5. Immunohistochemical localization of MANF protein in the brain and non-neuronal tissues of adult mouse.

Immunohistochemical Localisation of MANF Protein in Adult and Postnatal Mouse Tissues Immunohistochemistry was used to study the cellular localization of MANF protein in the brain and in selected non-neuronal tissues of adult mouse. A widespread distribution of MANF was detected (FIG. 5), which was in accordance with the results obtained by RT-PCR and in situ hybridization analyses of adult mouse tissues. In the adult mouse brain, MANF protein was found in several regions (FIG. 5A-K), and mainly in cells of neuronal morphology. In the cerebral cortex, relatively strong MANF expression was observed in cortical layers II-VI (FIG. 5A, B). Especially pyramidal-like, large cells in the layer III had intense labelling (FIG. 5B). Specificity of MANF antibodies was evaluated by pre-incubating the antibodies with MANF protein before application on tissue sections. Since this pre-incubation abolished MANF labelling from cortical cells (FIG. 5C), we concluded that MANF antibodies specifically recognized MANF protein on tissue sections. In the hippocampus, MANF protein was detected in neurons of CA1-CA3 pyramidal regions (FIG. 5D) and in dentate gyrus (FIG. 5E). In the striatum, clear but weak MANF staining was observed in (FIG. 5F). In the substantia nigra, scattered MANF-positive cells were detected mostly in pars reticulata area (FIG. 5G, H). Especially strong MANF labelling was detected in the Purkinje cells of cerebellum (FIG. 5I). Notably, MANF protein was localized not only in the Purkinje cell bodies but also in dendrites extending to the molecular layer (FIG. 5I). Strong MANF labelling was also observed in cells located in the spinal cord (FIG. 5J), and non-neuronal cells of the choroid plexus (FIG. 5K). In peripheral tissues studied, MANF labelling was intense in serous tubules of salivary gland (FIG. 5L). In testis, Manf mRNA and protein were detected in seminiferous tubules by in situ hybridization (FIG. 5M) and immunohistochemistry (FIG. 5N), respectively. MANF protein was found mainly in early spermatocytes (FIG. 5N).

The localization of MANF protein was also studied in sections of postnatal P1 and P10 mouse brain (FIG. 6). The detected expression of MANF protein was quite similar and well matching to the expression pattern observed in adult brain. At P1 MANF labelling was intense in the mitral cell layer of olfactory bulb (FIG. 6A). Several brain regions stained positive for MANF, including the striatum (FIG. 6B), hippocampus (FIG. 6C, D), thalamus (FIG. 6E), cerebral cortex (FIG. 6F) and substantia nigra (FIG. 6G). At P10, relatively strong MANF signal was detected in the hippocampus and thalamus (FIG. 6H, I, J), in contrast to the observed weak signal in striatum (FIG. 6K). In the SN of P10 mouse brain, MANF staining was localized mainly in cells of pars reticulata area (FIG. 6L). MANF protein colocalized with neuronal marker NeuN in cells of P10 cerebral cortex (FIG. 6M, N) indicating that MANF was mainly expressed in neurons.

Manf Expression Starts Early in Mouse Embryonic Development

We studied Manf mRNA and protein expression in embryonic mouse tissues using in situ hybridization and immunohistochemistry. In situ hybridization analysis of sections from E12.5 mouse embryos revealed a wide expression of Manf transcripts in the brain. Prominent Manf mRNA expression was detected in the roof of neopallial cortex (FIG. 7 A-C). Manf transcripts were detected also in the embryonic midbrain and striatum, although the expression level was relatively low. Non-neuronal cells of choroid plexus in the lateral ventricles expressed high levels of Manf (FIG. 7D). In the PNS of E12.5 embryos, Manf expression was detected at relatively low level in trigeminal and dorsal root ganglia. Outside the nervous system, high Manf-specific signal was detected in the cartilage primordia of head and vertebra (FIG. 7E). Manf mRNA levels were also high in the liver and umbilical vessels (FIG. 7A, B). Manf-specific labelling was detected at relatively low level in many developing organs of E12.5 mice embryos, including the lung, metanephros and gut. In accordance with the data from E12.5 mouse, widespread Manf mRNA expression was detected also in E15 mouse embryos (data not shown). Robust Manf mRNA expression was observed in the salivary gland of E17 mouse embryos (FIG. 7F). By immunohistochemical analysis, MANF protein was detected at relatively high levels in the roof of neopallial cortex of E14 mouse embryos (FIG. 8A). In the striatum (ganglionic eminence), MANF signal was low (FIG. 8B). Intense MANF staining was detected in the median sulcus (FIG. 8C). Similarly with the adult, high levels of MANF protein were detected in the choroid plexus of E14 embryonic brain (FIG. 8D). In the midbrain of E16 mouse embryos, MANF protein was detected in the developing substantia nigra, although the signal was quite moderate (FIG. 8E, F). The developing SN in embryonic brain sections was identified by tyrosine hydroxylase staining of sections parallel of those used for MANF staining (FIG. 8G). In the PNS, MANF protein was detected in the DRG, SCG and trigeminal ganglia of embryonic E17 mouse (FIG. 8H-J). In the mantle layer of spinal cord, MANF signal was relatively low, although some strongly positive cells were also found (FIG. 8K). In the non-neuronal tissues of E17 mouse embryos, abundant MANF expression was detected in the submandibular gland (FIG. 8L) and in serous tubules located in the nasal cavity (FIG. 8M). High levels of MANF protein were detected also in the pancreas of E17 mouse embryos (FIG. 8N). Interestingly, strongly MANF-positive cells were detected in the vomeronasal organ (FIG. 8O), and in several epithelial cells, including the olfactory ephitelium. In accordance with in situ hybridization analysis, MANF protein was detected in the liver and in cartilage primordia of vertebra of E13 mouse embryos (not shown). The obtained in situ hybridization data and immunohistochemical data in accordance showed a wide distribution of Manf mRNA and protein expression, respectively, in embryonic mouse tissues.

MANF mRNA Levels are Differentially Regulated after Ischemic and Epileptic Brain Insults We finally explored whether pathological conditions affecting the adult rat brain could lead to changes in Manf gene expression. Following 2 h of electrically induced SE, changes of Manf mRNA levels in hippocampal formation were confined to dentate granule cell layer (FIG. 9). At 2 h after the insult, we found a significant increase in this area (to 171% of control), but the level of Manf mRNA was decreased at 24 h and 1 week after the insult (FIG. 9A). Transient increases of Manf mRNA expression were detected at 2 or 24 h after SE in the thalamic reticular nucleus (to 170% of control; FIG. 9B) and in several cortical areas, including piriform, retrosplenial and parietal cortex (to 160, 175, and 136% of control, respectively; FIG. 9C-E). In contrast, in animals subjected to 10 min of global forebrain ischemia, changes of Manf gene expression were more widespread in the hippocampal formation while being restricted in the cerebral cortex (FIG. 10). We detected transient increases of Manf mRNA levels at 24 h post-insult in dentate gyrus granule cell layer and hilus as well as in the CA1 region (to 157, 137, and 151% of control, respectively; FIG. 10A-C). No changes were detected in thalamic reticular nucleus or in cortical areas except a transient increase of Manf mRNA expression at 2 h in the retrosplenial cortex (to 136% of control). Following both insults, the expression was mostly neuronal in all examined structures. At 1 week after SE and ischemia, Manf mRNA level did not differ from control value in any analyzed area.

Discussion

Neurotrophic factors, including GDNF family ligands and neurotrophins, have essential roles in the development, maintenance and function of the vertebrate nervous system (Huang and Reichardt, 2001; Airaksinen and Saarma, 2002). Neurotrophic factors promote the survival of neurons during developmental periods of programmed cell death (PCD) and regulate the density of target innervation. However, it is still poorly understood how trophic factors regulate the development and maintenance of the nervous system in vivo, especially that of the CNS.

Novel neurotrophic factor MANF was discovered as a survival promoting factor for embryonic dopaminergic neurons in vitro (Petrova et al., 2003). We recently identified CDNF, the second member of MANF/CDNF family of neurotrophic factors. CDNF protects and rescues adult rat dopaminergic neurons in vivo in 6-OHDA model of PD (Lindholm et al., 2007). The trophic functions of MANF and CDNF on dopaminergic neurons suggest that they might be beneficial in treatment of PD (Petrova et al., 2003; Lindholm et al., 2007). Interestingly, the invertebrates including Caenorhabditis elegans and Drosophila melanogaster, also have a homologous gene for MANF/CDNF (Petrova et al., 2003, Lindholm et al., 2007). Drosophila MANF-deficient flies die in embryo showing severe degeneration of dopaminergic axons and drastic decrease in the level of dopamine (M. Palgi, R. Lindstrom, J. Peranen, T. P. Piepponen, M. Saarma, and T. I. Heino, unpublished observations). Thus, MANF/CDNF family proteins represent the first evolutionarily conserved family of neurotrophic factors which has neurotrophic activities also in the invertebrates.

Based on EST and genomic sequences we concluded that in contrast to the sequence reported by Petrova et al. (2003), the amino acid 176 of human MANF is arginine (R) instead of proline (P). This is in accordance with the human ARMET (MANF) sequence reported by Mizobuchi et al. (2007). According to Mizobuchi et al. (2007) ARMET (MANF) is an endoplasmic reticulum (ER) resident protein. However, we detected human and mouse MANF proteins in the culture media of transiently transfected cells, which shows that MANF does not only reside in the ER but it is also secreted from cells. After cleavage of the determined signal sequence of 21 amino acids, the secreted mature human MANF protein consists of 158 amino acids (see FIG. 1A, B) including eight cysteine residues conserved in MANF and CDNF proteins (Petrova et al., 2003; Lindholm et al., 2007; Mizobuchi et al., 2007). Based on ESI-MS analysis, the eight cysteine residues formed four intramolecular disulfide bonds in human MANF expressed in insect cells or E. coli, respectively, which was in accordance with an earlier report indicating that ARMET (MANF) is likely having four intramolecular disulfide bonds (Mizobuchi et al., 2007). Interestingly, according to Petrova et al. (2003) human MANF protein overexpressed in HEK293 cells was sialidated. However, this was in contrast to our observations, since human MANF secreted from transiently transfected COS-7 was not glycosylated or post-translationally modified. It is possible that post-translational modification of human MANF differs depending on the host cell used for protein overexpression.

Only little is known about the expression of MANF mRNA and protein in the development, adult tissues and pathological conditions. Recently Mizobuchi et al. (2007) reported Armet (Manf) mRNA expression in several adult mouse tissues by Northern hybridization, and showed ARMET (MANF) protein in the adult mouse testis and pancreas by immunohistochemistry. In the present study we characterized mouse Manf mRNA and protein expression in postnatal and adult brain and in developing embryonic tissues, which have not been previously studied.

Based on our in situ hybridization and immunohistochemical analyses, Manf mRNA and protein was widely expressed in the mouse nervous system and non-neuronal tissues. In accordance with results obtained from mouse, MANF mRNA was also detected in several brain regions and non-neuronal tissues of adult human. In the mouse, Manf expression started early in embryonic development, suggesting that MANF has an important function not only in the nervous system, but also in several other tissue types. In the brain, relatively high levels of Manf mRNA and protein were detected in adult and postnatal cerebral cortex, in which MANF signal was located mainly in neurons. In accordance, the neopallial cortex of embryonic mice expressed Manf mRNA and protein in relatively high amounts. Also in the hippocampal formation of adult and postnatal brain, the detected MANF levels were high. Our data obtained by in situ hybridization analysis of Manf expression in adult mouse brain was in accordance with Armet mRNA expression data shown in the Allen Brain Atlas (www.brainatlas.org/aba/). Interestingly, MANF and CDNF (Lindholm et al., 2007) protein expression patterns were similar in the adult mouse brain. Relatively high levels of CDNF (Lindhohn et al., 2007) were detected in the cortical neurons, hippocampus, and in the cerebellar Purkinje cells, which also expressed high levels of MANF.

During development, nigral dopaminergic neurons elongate their axons to the striatum in which synaptic contacts are formed. These contacts are pruned postnatally in a two-phased apoptotic cell death period, which peaks at P2 and P14 in rat (Oo and Burke, 1997). However, neurotrophic factors regulating this apoptotic process in vivo are still unknown (Burke, 2003). Manf mRNA and protein were detected in the midbrain and striatum of postnatal P1 and P10 mice brain and also in the adult, suggesting that MANF, similarly with CDNF (Lindholm et al., 2007) may participate in the development of dopaminergic contacts. GDNF expression is high in the postnatal striatum at the time of PCD (Schaar et al., 1993; Strömberg et al., 1993), which supports the idea of GDNF as a target-derived survival factor for dopaminergic neurons. However, GDNF knock-out mice, which die at birth, do not have defects in the dopaminergic system (Airaksinen and Saarma, 2002). Furthermore, the ablation of GDNF receptor RET (REarranged during Transfection) from dopaminergic neurons has vitally no effect on their development (Kramer et al., 2007). This data suggests that other factors than GDNF have a role in the embryonic development of dopaminergic neurons. We detected Manf mRNA and protein in the midbrain of embryonic mouse, suggesting that MANF may be one of these factors.

We investigated the changes of Manf mRNA expression in two experimental pathological conditions in the rat, i.e., following 2 h electrically-induced SE and 10 min of global forebrain ischemia, respectively. This epileptic insult gives rise to neuronal damage in the dentate hilus and CA1 and CA3 regions (Jakubs et al., 2006). The global ischemia model replicates the consequences of cardiac arrest or coronary artery occlusion, and causes selective death of vulnerable neuronal populations like CA1 pyramidal neurons of hippocampus (Kokaia and Lindvall, 2003). Our findings provide the first evidence that Manf mRNA levels are influenced by pathological conditions in the adult brain and differentially regulated after epileptic and ischemic insults. Following SE, Manf mRNA expression was transiently elevated in dentate granule cell layer, thalamic reticular nucleus, and cortical areas. Global forebrain ischemia gave rise to transient increases in Manf expression, which were more widespread in hippocampal formation and restricted in cerebral cortex. The different pattern of changes in Manf mRNA levels following epilepsy and ischemia most likely reflects the specific characteristics of the insults. The functional consequences of the insult-induced changes in Manf mRNA expression and the presumed, corresponding alterations in protein levels remain to be elucidated. However, the high basal Manf mRNA levels and the rapid and dynamic gene changes in the hippocampal formation after two insults associated with neuronal death show that MANF can regulate neuronal survival and synaptic and cellular plasticity similar to what has been shown, e.g., for the neurotrophins. Thus, MANF can be used in the treatment of ischemic and epileptic conditions.

Manf mRNA and protein expression, similarly with that of CDNF (Lindholm et al., 2007), was detected in several non-neuronal tissues of embryonic and adult mouse. A wide expression pattern is not unusual for neurotrophic factors. GDNF, for example, is expressed in many brain regions (Arenas et al., 1995; Springer et al., 1994) and in peripheral organs (Trupp et al., 1995; Suvanto at al., 1996), and has a crucial role in the kidney development and spermatogenesis (Airaksinen and Saarna, 2002). We found MANF mRNA and protein especially abundant in mouse secretory cells and tissues, including the embryonic and adult choroid plexus, salivary gland and embryonic pancreas. An earlier report (Mizobuchi et al., 2007) indicates that ARMET (MANF) may be a stress-inducible ER protein with chaperone functions. The suggested chaperone function of MANF could be important especially in secretory tissues and organs. Our data clearly show that MANF is a secretory protein that is widely expressed in the brain. In line with that, MANF promotes the survival of dopaminergic neurons.

MANF receptor and its signalling mechanisms are still unknown. The detected wide expression of MANF in the nervous system and non-neuronal tissues suggest that MANF, in addition to its role as a neurotrophic factor, has additional important functions in many tissue types.

Example 2

Experimental Procedures

Animals

In all experiments, adult male Wistar rats (Harlan), weighing 250-280 g at the beginning of the experiment, were used. The rats were housed in groups of three to four rats under a 12:12-h light:dark cycle at an ambient temperature of 22° C. Tap water and rat chow (Altromin 1324, Chr. Petersen A/S) were available ad libitum. The use of experimental animals was approved by the Committee for Animal Experiments of the University of Helsinki, and the chief veterinarian of the County Administrative Board (permissions HY 17-03 and HY 1406).

Intrastriatal Injections of Neurotrophic Factors and 6-OHDA

In the studies of neuroprotection, stereotaxic surgery was performed in two sessions (Kearns et al 1997) using isoflurane anesthesia (4.5% during induction and 3% during surgery). The animals were placed in a stereotaxic frame (Stoelting, Ill., USA). The skull was exposed and burr holes were made using a high speed dental drill. Injections were carried out using a 10-μl Hamilton microsyringe at a rate of 1 μl/min. At the completion of each injection, the needle was kept in place for 2 minutes to minimize backflow of the solution. All control animals were administrated 4 μl of PBS or 10 mM citric acid in the left striatum using coordinates relative to the bregma and dura (A/P +1.0, L/M +2.7, D/V −5) according to the atlas of Paxinos and Watson (Paxinos and Watson 1986). Trophic factor treated animals received either 3, 10 or 30 ug of hMANF or 10 μg of recombinant human GDNF (Amgen Inc, CA, USA) in a 4 μl buffer delivered to the striatum. After the injection of vehicle or the trophic factor, the animals were allowed to recover from the anesthesia in single cages until the second surgery. Six hours later, all animals were subjected to 8 ug/4 ul of 6-hydroxydopamine (Sigma Chemical CO, St. Louis, Mo., USA; calculated as free base, dissolved in ice-cold saline with 0.02% ascorbic acid) in the left striatum. Prior to 6-hydroxy-dopamine injections desipramine (Sigma Chemical CO, St. Louis, Mo., USA; 15 mg/kg, ip, 1 ml/kg) was administrated to prevent the uptake of 6-hydroxydopamine into noradrenergic nerve endings, and thus protect these nerve terminals from destruction.

The study of neuroprotective properties of MANF consisted of the following groups: intrastriatal PBS+6-OHDA, intrastriatal GDNF (10 ug)+6-OHDA and intrastriatal MANF (3, 10 or 30 ug)+6-OHDA.

In the studies of neurorestorative effect of chronic recombinant human MANF infusions animals received a two-site intrastriatal 6-OHDA lesion unilaterally (10 ug per site, total dose of 6-OHDA 20 ug). At two weeks postlesion one group of rats (lesion-control group) was perfused. All other animals were implanted with a miniosmotic pump to receive a chronic infusion of either MANF (1.5, 3 or 4.5 ug/24 h), GDNF (3 ug/24 h) or the vehicle solution for 2 weeks. At 12 weeks postlesion rats were perfused and their brains were processed for TH-immunohistochemistry.

Behavioral Analysis

Rotational behavior. Behavioral tests were carried out as described earlier (Ungerstedt and Arbuthnott 1970, Lindholn et al 2007). In the neuroprotection studies rotational behaviour was measured 2 and 4 weeks and in the studies of neurorestoration rats were monitored before the minipump implantation and after the lesion (4, 6, 8, 10 or 12 weeks postlesion) for their rotational behaviour postlesion, Drug induced rotational activity of the rats was monitored in automatic rotometer bowls (Colbourn Instruments). Once the rats were allowed to habituate to the test chamber for 30 min, D-amphetamine (University Pharmacy, Helsinki, Finland; 2.5 mg/kg i.p) was administrated. The number of full (360°) clockwise and counterclockwise turns was recorded for a period of 2 h. Net ipsilateral turns to the lesion were calculated by subtracting the turns to the left from the turns to the right. The tests were repeated at 4 weeks post lesion, respectively.

Histology

Perfusion and Tissue Processing.

At 4 weeks postlesion (neuroprotection studies) or 2 or 12 weeks postlesion (neurorestoration studies), the rats were anesthetized with an overdose of sodiumpentobarbital (90 mg/kg, i.p, Orion Pharma, Finland) and perfused intracardially with phosphate-buffered saline (PBS) followed by 4% paraformaldehyde in 0.1 M sodium phosphate buffer, pH 7.4. The brains were removed, post fixed for 4 h and stored in sodium phosphate buffer containing 20% sucrose at 4° C. Serial coronal frozen sections of 40 μm were cut on a sliding microtome.

Tyrosine Hydroxylase Immunohistochemistry

Six sets of sections were collected in cryoprotectant solution (0.5M PB, 30% glycerol and 30% ethylenglycole) and stored at −20° C. until immunohistochemical processing. Free-floating sections were processed for TH-immunohistochemistry. Following three rinses in PBS, endogenous peroxidase activity was quenched for 5 minutes in 3% $H_2O_2$/10% methanol/PBS. After 3 rinses in PBS, the sections were preincubated with normal horse serum (NHS)/0.3% Triton X-100 in PBS in order to block nonspecific staining. Thereafter sections were incubated overnight at room temperature with a 1:2000 dilution of biotinylated mouse-anti-TH (Chemicon, Temecula, Calif.). This was followed by incubations with 1:200 dilution of biotinylated horse-anti-mouse (Vector, BA2001) and by incubation in the avidin-biotin peroxidase complex using the Elite ABC Vectastain kit (Vector Laboratories). The reactions were visualized using DAB as a chromogen.

Morphological Analysis

SN Cell Counts.

Optical fractionator method was used to estimate the number of TH-positive cells in SNpc West et al. 1991; Mouton et al. 2002. The entire SNpc was analyzed with the Stereo Investigator platform (MicroBrightField, Germany) attached to a Olympus BX51 microscope. From each animal, 3 sections from the central portion of the SNpc, where the medial terminal nucleus (MTN) was present (level A/P −5.3), were selected for quantitative analysis as described by Sauer et all 995. Each reference space was outlined at low power (4×), and cells were counted using a high magnification (60×, oil immersion) objective. Cell numbers were expressed as the mean number/section. Cells were counted using the optical fractionator method in combination with the dissector principle and unbiased counting rules.

Striatal Fiber Density Measurements.

The optical densities (OD) of the TH-positive fibers in the striatum were determined from three coronal striatal sections from each rat. Every sixth section between AP +1.6 and AP +0.20 were cut on a freezing microtome and processed for TH-immunohistochemistry. Digitalized images from TH-stained striata were taken with Optronics digital camera and a constant illumination table, and fibre densities were measured using Image Pro-Plus™ software (Version 3.0. I., Media Cybernetics). The OD analysis was performed under blinded conditions on coded slides. The data is presented as percentage of the intact side that was defined as 100%.

Preparation of $^{125}$I-Labeled Neurotrophic Factors

GDNF (1.5 µg), MANF (1.0 µg) and CDNF (1.0 ug) were iodinated with NA $^{125}$I using the lactoperoxidase method. The neurotrophic factor in question was dissolved in 30 ul of 0.25 M phosphate buffer, pH 7.5, and mixed with $^{125}$I-Na (1 mCi=37 mBq, Amersham Biosciences, U.K.). The reaction was started by adding lactoperoxidase 50 ug/ml and $H_2O_2$, 10 ul each. The mixture was incubated at room temperature for 20 min and the reaction was stopped by adding 3 volumes of 0.1 M phosphate buffer, pH 7.5, containing 0-1 M NaI, 0.42 M NaCl and 25 ul of 2.5% BSA. Free iodine and iodinated growth factor was separated by using Sephadex G-25 columns (PD10, Amersham Biosciences, U.K.). For column equilibrium and elution 0.1 M phosphate buffer, pH 7.5 was used. The iodinated growth factors were concentrated by using YM-10 Centricon columns (Millipore).

Intrastriatal Injections of $^{125}$I-Neurotrophicfactor

An amount of 6 µl of radiolabeled protein plus vehicle or radiolabeled protein plus cold competitor was injected directly in to the striatum using the same stereotaxic coordinates as in the neuroprotection studies. Rats were perfused transcardially 24 hours later. Portions of the central nervous tissue were used for γ counting and the remainder was sectioned for autoradiography.

Autoradiographic Analysis of the Distribution of $^{125}$I-Neurotrophic Factor

Rats receiving intrastriatal injection of $^{125}$I MANF, $^{125}$I CDNF or $^{125}$I GDNF were perfused 24 hours following stereotaxic injections. Coronal paraffin sections (7 µm) were juxtaposed against autography film (Kodak Biomax MS) for 4 weeks.

Emulsion Autoradiography

Coronal paraffin sections (7 um) of striatum, frontal cortex and substantia nigra were dipped in emulsion (Kodak autoradiography emulsion) and exposed for 4 weeks. Slides were developed and counterstained with haematoxylin (J. T. Baker).

Quantification of $^{125}$I-Neurotrophic Factor in Central Nervous System Tissues Following Intrastiatal Injections The amount of intrastriatally administered neurotrophic factor in different brain structures was determined after perfusions. The brain was removed from the skull and hippocampus, substantia nigra, striatum and cortex were dissected out and the wet tissue was weighted out. Radioactivity of the tissue was quantified for 1 min in a gammacounter. Results are expressed as CPM/mg wet weight.

Statistical Analysis

Results were analysed using one-way ANOVA followed by Tukey/Kramer's post-hoc test. A one-way ANOVA for repeated measures followed by Tukey/Kramer's post-hoc test was used for the results from behaviour studies. Results are expressed as mean±s.e.m. Results were considered significant at $P<0.05$.

Results

Behavioral experiments and different morphological analysis (counting of nigral Tyrosine hydroxylase (TH)-positive cells and analysis of striatal TH-immunoreactivity) were carried out in order to study the effect of intrastriatal MANF in a rat PD model.

The transportation profile of MANF and CDNF was investigated based on autoradiographic and γ counting detection of $^{125}$I labeled trophic factors and by studying the diffusion and transportation of unlabeled proteins.

Neuroprotection Studies Using Single Injection of Graded Doses of MANF

Amphetamine Induced Rotational Behaviour

In neuroprotection studies the effects of a single injection of MANF was studied in an experimental model of Parkinson's disease. MANF was given at 3 different doses (3, 10 or 30 µg) 6 hours before intrastriatal injection of 6-OHDA. In order to study whether the lesions were successful, behavioral experiments were done at 2 and 4 weeks post lesion, and morphological analyses were carried out immediately after the behavioural experiments (FIG. 11, experimental plan).

In neuroprotection studies the effects of a single injection of MANF was studied in an experimental model of Parkinson's disease, described in detailed earlier (Lindholm et al 2007). The neuroprotective effect was compared to that of GDNF. MANF (3, 10 or 30 µg/striatum), GDNF (10 ug) or vehicle was given 6 hours before neurotoxin (6-OHDA 8 µg) unilaterally into the striatum. In vehicle and 6-OHDA-treated rats, amphetamine induced a strong ipsilateral turning behavior both at 2 and 4 weeks post lesion indicating destruction of dopamine nerves. MANF prevented 6-OHDA induced degeneration of dopaminergic nerves in a bell shaped dose-dependent manner. At 2 weeks post lesion the difference between MANF pretreated rats and control rats was not significant (FIG. 12 A). MANF reduced the amphetamine (2.5 mg/kg, i.p) induced rotation compared to the control group at 4 weeks post lesion and the effects were more pronounced than at 2 weeks post lesion but there were no statistical differences between the groups. There were differences in rotational behaviour between rats treated with the point mutated MANF (176P), 10 µg, and those rats treated with correct MANF protein. When data from rotation experiments was analyzed using ANOVA for repeated measures, all concentrations of MANF and also the positive control GDNF 10 ug/striatum differed significantly from the control group at 2 and 4 weeks post lesion, MANF 10 ug being the most effective dose tested (p<0.01, FIGS. 12 B and C).

Protection of TH-Positive Dopamine Neurons in the Substantia Nigra Pars Compacta To confirm the extent of lesion, morphological analysis from rat nigral tyrosine hydroxylase-stained sections were carried out. Intrastriatal injection of 6-OHDA (8 ug) resulted in about 34% reduction in TH-positive neurons in SN. The unilateral injection of 6-OHDA into the striatum of rats pretreated with either MANF 3, 10 or 30 µg, or GDNF 10 ug caused a loss of about 19%, 14%, 28% or 12% of TH-positive cell bodies in the substantia nigra pars compacta (SNpc), respectively, when measured 4 weeks after the treatments (FIG. 13 A). There were no statistical differences between treatments. The unilateral injection of 6-OHDA into the striatum of rats pretreated with point mutated MANF (176P) 10 µg caused a loss of about 20% of TH-positive cell bodies in the substantia nigra pars compacta (SNpc).

TH-Positive Immunoreactivity in STR

The denervation caused by intrastriatal 6-OHDA was further assessed measuring the optical density (OD) of TH-positive fibers in the striatum. In these analyses the similar trend was seen than in SN cell counts. MANF 10 ug was the most effective dose tested in protecting TH+fibers (26% loss in OD) but it did not differ statistically from control-group (36% loss in OD). MANF 3, 30 ug nor GDNF did not show any statistical difference compared to the control-group (32%, 37% or 32% loss in OD) (FIG. 13 C).

Neurorestorative Studies Using Chronic Infusion of Graded Doses of MANF

The effect of chronic MANF infusion was studied in a neurorestorative model (FIG. 14). All animals received a two-site intrastriatal 6-OHDA lesion unilaterally (10 ug per site, total dose of 6-OHDA 20 ug). At two weeks postlesion one group of rats (lesion-control group) was perfused. All other animals were implanted with a miniosmotic pump to receive a chronic infusion of either MANF (1.5, 3 or 4.5 ug/24 h), GDNF (3 ug/24 h) or the vehicle solution for 2 weeks. The animals were monitored before the minipump implantation and after the lesion (4, 6, 8, 10 or 12 weeks postlesion) for their rotational behaviour. At 12 weeks postlesion rats were perfused and their brains were processed for TH-immunohistochemistry. Intrastriatal MANF (1.5 and 4.5 ug/24 h) and GDNF (3 ug/24 h) were able to restore the dopaminergic function (FIG. 15 A, B). The GDNF administration prevented the degeneration of dopaminergic neurons in substantia nigra and the loss of TH-immunoreactive fibers in striatum. The data from IHC-analysis in 3 different MANF treatment group (1.5, 3 or 4.5 ug/24 h) did not correlate well with the behavioural data due to the small number of animals in treatment group (n=4-6) (FIG. 16 A, B).

Diffusion Studies

The diffusion of unlabeled MANF and GDNF was studied by injecting unlabeled human recombinant MANF or GDNF into striatum and localized the molecule by using immunohistochemistry.

Injection of 10 ug of MANF or GDNF in 4 ul was detected in striatum 24 hours and 3 days later (FIGS. 17 and 18). After 24 h, MANF staining was shown to distribute throughout the striatum. There was also MANF-staining present in frontal cortex. MANF-staining correlated well with distribution studies done with iodinated MANF-protein (FIGS. 19, 20 and 21).

Transport Studies Using Iodinated Growth Factors (MANF, CDNF and GDNF)

We also investigated the transportation of novel trophic factors. Iodinated trophic factors ($^{125}$I MANF, $^{125}$I CDNF and $^{125}$I GDNF) were injected into the left striatum according the coordinates in rat brain atlas (Paxinos and Watson 1997). The rats were perfused 24 hours later. Transportation experiments were done based on the autoradiographic and γ counting detection of $^{125}$I labeled trophic factors in brain sections. Following injection of $^{125}$I MANF autoradiography revealed a labeling in the ipsilateral striatum and in the cortex but not in substantia nigra (FIG. 19). Labeling after injection of $^{121}$I CDNF or $^{121}$I GDNF occurred in autoradiography film in ipsilateral cortical and striatal sections, as well as in the SN section (FIG. 19).

To verify the results from the autoradiography experiments we quantified also the distribution of novel trophic factors to the SN and cortical area. As shown in FIG. 20 a, radioactivity after intrastriatal $^{125}$I MANF injection was at background levels in SN. Following injection of $^{125}$I CDNF or $^{125}$I CDNF and cytochrome c there was much more radioactivity in ipsilateral SN than after $^{125}$I MANF injection. A significant amount of radioactivity was found in the ipsilateral SN area when $^{125}$I CDNF (or $^{125}$I GDNF and cytochrome c) was injected into striatum. The radioactivity measured after $^{125}$I GDNF and cytochrome c and after $^{125}$I CDNF injections was one third of the radioactivity after $^{125}$I GDNF injections. When the results were expressed as percent of radioactivity in striatum (FIG. 20 b), the radioactivity after $^{125}$I GDNF injection was 1.5% and after $^{125}$I CDNF injection 1.9%.

The quantity of radioactivity in the cortical area was analyzed carefully. There was twice as much radioactivity in cortical samples after intrastriatal $^{125}$I MANF injection than after $^{125}$I GDNF or $^{125}$I CDNF injections (FIG. 21 a). Because it was possible that some of the radioactivity in the cortical tissue sample might originate from the striatum, we investigated also the radioactivity of a pure frontal cortex sample (without any tissue from striatum). When radioactivity was measured from the frontal cortical area, there was 5 times more radioactivity after $^{125}$I MANF injection compared to the radioactivity after $^{125}$I GDNF injection and 3 times more radioactivity after $^{125}$I CDNF injection (FIG. 21 b). Studies on the distribution of iodinated trophic factors in rat brain revealed that MANF behaved differently from CDNF and GDNF. MANF was transported to the frontal cortex but not to SN while GDNF and CDNF were transported to SN after intrastriatal injection.

MANF is most likely transported via glutamatergic or via other neurons projecting to cortex. This may be an important part in the drug action of MANF.

Example 3

Material and Methods

Animals and Drugs

Adult male Sprague-Dawley rats (250-350 g) were used. Recombinant MANF protein was used and PBS as vehicle. In the first set of experiment animals were divided into 4 groups: (1) PBS; (2) MANF 1 µg/µl: (3) MANF 2 µg/µl; (4) MANF 4 µg/µl and these rats were used to study the neuroprotective effects of MANF protein on the infarction volume. In the second set of experiments rats were divided into 2 groups: (1) PBS; (2) MANF 2 µg/µl. These rats were used to study whether MANF has anti-apoptotic activity.

Intracerebral Injections and MCA Ligation

Ligation of the right middle cerebral artery (MCA) and bilateral common carotids (CCAs) was performed with methods previously described (Chen et al., 1986). Briefly, the rats were anesthetized with chloral hydrate (400 mg/kg, IP). The bilateral CCAs were identified and isolated through a ventral midline cervical incision. Rats were attached to streotaxic apparatus and a craniotomy was made in the right hemisphere. Recombinant MANF protein (0, 6, 12, 24 μg) or vehicle was administered intra-cranially into three cortical sites (FIG. 22). Two micro liters of MANF solution (1, 2 or 4 μg/μl) or PBS was injected and allowed to diffuse for five minutes prior to needle removal (FIG. 25). After the last injection the right (MCA) was ligated with a 10-0 suture and bilateral common carotids (CCA) were ligated with nontraumatic arterial clamps for 60 minutes. After sixty minutes of ischemia the suture around the MCA and arterial clips on CCAs were removed. After recovery from anesthesia, the rats were returned to their home cage.

TTC Staining

Triphenyl-tetrazolium chloride (TTC) staining was used to study the infarction volume in the brain. Animals were killed 48 hours afterwards. Brains were removed and sliced into 2 mm thick coronal section. The sections were stained with 2% TTC solution for fifteen minutes. The area of infarction in each slice was measured with a digital scanner and Imagetools programs (University of Texas Health Sciences Center). The volume of infarction in each animal was obtained from the product of average slice thickness (2 mm) and sum of infarction areas in all brain slices examined.

TUNEL Staining and Analysis

Rats were decapitated 24 hours after ischemia. The brains were taken out, frozen with isopentane and cut into sections (25 μm) in a cryostat. The sections were mounted on microscope slides, air-dried, then fixed with 4% paraformaldehyde for 30 minutes at 4° C. A standard terminal deoxynucleotidyl transferase-mediated dUTP nick-end labeling (TUNEL) procedure for frozen tissue sections, with minor modifications, was performed (In Situ Cell Death Detection Kit, POD, Roche Applied Science. Briefly, slide-mounted sections were rinsed in 0.5% Triton X-100 in 0.1 M phosphate buffer for 20 minutes at 80° C. Sections were rinsed three times with 0.1 M phosphate buffer. To label damaged nuclei, 100 μl of TUNEL reaction mixture was added onto each sample followed by a 60-minute incubation at 37° C. in a humidified chamber. Procedures for controls were carried out as described in the manufacturer's manual. Sections were rinsed three times with 0.1 M phosphate buffer, rinsed with $H_2O$, air dried and coverslipped. Histological images were acquired using an Infinity3 camera, NIKON 80i microscope and QCapture Pro 5.0 software. Pixel density of TUNEL-positive nuclei was quantified from six sections of each brain area and averaged using with NIS Elements 2.3 software.

Results

Administration of MANF Significantly Reduced the Cerebral Infarction

We found that administration of MANF significantly reduced the cerebral infarction (FIG. 23, left column, P=0.032, treatment effect, one-way ANOVA). The infarction volume was significantly smaller in the first four brain slices of the MANF-treated rats as compared with vehicle-treated animals (PBS=88±9, MANF 6 μg=45±13 mm, MANF 12 μg 58±6, MANF 24 μg 67±45 mm. In addition, the area of the largest infarction in a slice was found to be larger in PBS-treated rats (16.8±1.1 mm²) as compared with MANF-treated rats (FIG. 24, MANF 6 μg=8.9±2.2 mm²; MANF 12 μg 11.7±2.0 mm²; MANF 24 μg 14.3±2.0 mm², P=0.0035, Kurskal-Wallis one-way analysis of valiance on ranks).

Pretreatment with MANF Reduced TUNEL Activity Locally

TUNEL activity, as measured by pixel density, was found to be similar at a rostral cortical area between PBS and MANF 2 μg/μl treated rats. At level +2.2 from bregma the averages were: PBS=494±152, MANF=534±70 (FIG. 26A). However at level −0.2-0.2 mm from bregma it was found that MANF 2 μg/μl significantly reduced TUNEL activity (FIG. 26B, PBS=764±60, MANF=322±141). As the level counted on FIG. 26B is the same level as the local MANF injections were given, this data shows that anti-apoptotic activity of MANF is local.

Conclusions

Pre-stroke delivery of MANF significantly reduced the volume of infarction caused by MCA ligation Pre-stroke delivery of MANF significantly reduced the maximal infarction area caused by MCA ligation Local administration of MANF 12 μg reduced TUNEL activity in cortical brain areas Overall, these results show that MANF has neuroprotective effects against ischemia which may be related to its anti-apoptotic activity.

Example 4

MANF Crystallization and Structure Determination

X-ray crystallography has been used to study the MANF structure at near atomic resolution. For crystallization, the purified protein was concentrated and the protein buffer was changed to 10 mM HEPES, pH 7.0 supplemented with 100 mM NaCl, 0.01% (v/v) P8840 protease inhibitor cocktail (Sigma) and 0.01% $NaN_3$. Crystallization conditions were screened using the sitting-drop, vapor-diffusion technique by the Helsinki robot crystallization facility (Helsinki, Finland). Needle crystals of MANF were typically obtained within 1 to 2 weeks at 4° C. over a reservoir solution of 12-18% (w/v) PEG 8000. The final drops were prepared manually mixing 1-2 μl of the reservoir solution and 1-2 μl of the protein solution at 10-20 mg/ml. The crystals belong to spacegroup $P6_1$ (a, b=96.15 Å, c=34.94 Å) with one molecule per asymmetric unit. Hg-derivatives were prepared by soaking the crystals in the mother-liquor supplemented with saturated $CH_3Hg$-acetate.

For data collection at −180° C., crystals were harvested in cryoprotectant buffer containing 14% glycerol and were flash-frozen in liquid nitrogen. MANF native, Sulphur-SAD and Hg-derivative X-ray diffraction data were collected, respectively, on beamlines ID14-1, ID23-1 and ID14-3 at the European Synchrotron Radiation Facility (ESRF), Grenoble, France. Data were integrated and scaled with XDS (Kabsch, 1993) software. Data reduction, free R assignment, and all further data manipulation were carried out with the CCP4 suite of programs (CCP4, 1994). The initial MANF structure was determined by using the anomalous and isomorphous differences of the Hg-derivative at 4 Å resolution. However, the final MANF structure was determined by molecular replacement using the program MOLREP (Vagin and Teplyakov, 2000) with CDNF-ΔC (Parkash et al., manuscript) as a search model. The Sulphur-SAD data was used to locate the disulfide bridges. MANF structure refinement was carried out at 2.8 Å resolution to a crystallographic R factor of 18.8% and an $R_{free}$ of 21.4%. Structure quality was accessed using PROCHECK (Laskowski et al., 1993) and the Ramanchandran plot analysis of the refined final model showed no residues in the disallowed regions.

MANF structure revealed a two-domain protein with an all-alpha topology (FIG. 27). The N-terminal domain comprises a folded-leaf structure showing homology to saposin-like proteins (SAPLIPs). The N-terminal domain is stabilized with three disulfide bridges like in SAPLIPs. The MANF C-terminus bears an apparently flexible linker and a smaller alpha-helical domain with one more disulfide bridge. The MANF crystal structure provides atomic-level information to study the function in detail.

Example 5

MANF-Lipid Interactions

Method

Preparation of Vesicles and Tryptophan Fluorescence Measurements were Done Essentially as described (Zhao and Kinnunen, 2002).

Saposins are an increasing family of proteins with a wide variety of functions, that all seem to interact with membranes or lipids. Homology to saposin-like proteins (SAPLIPs) suggests that MANF and CDNF could also interact with membrane lipids. In the preliminary tests we found that MANF and CDNF bind with relatively high affinity to phospholipids, such as 1-palmitoyl-2-glutaroyl-sn-glycero-3-phosphocholine. Interestingly, MANF and CDNF bind to both normal and oxidized lipids. It seems that both proteins bind to oxidized lipids at the membrane interface. Upon the binding, the conformation of MANF and CDNF changes and aggregation or clustering of proteins at the membrane interface may occur. It is of great interest to find out both the structure of the MANF-lipid complex, as well the biological role of this interaction.

Therefore, nuclear magnetic resonance (NMR) is used to study the conformational changes after the protein binding to oxidized lipids. Using site-directed mutagenesis and lipid binding assays the lipid binding sites of MANF are identified. As several SAPLIPs are dimeric proteins, it is addressed whether interaction with lipids leads to dimerization of MANF. Lipids could stimulate the dimerization of MANF and CDNF and thereby regulate their biological activity. To that end the role of phospholipids in the activation of MANF using the survival assays with DA neurons is tested.

Example 6

Methods

MANF Iodination

We took 1.0 µg of MANF in 1 µl and added 30 µl of 250 mM phosphate buffer, pH 7.5, then added 1 mCi of 125I Na (10 µl), then added 10 µl of lactoperoxidase solution, 50 µg/ml and then add 10 µl of $H_2O_2$ at 10 min and another 10 µl (diluted 1:1,000). Incubated at room temperature for 20 min. The reaction was stopped by adding 3 volumes of the 0.1 M phosphate buffer, pH 7.5, containing 0.1 M NaI and 0.42 M NaCl, then add 25 µl of 2.5% BSA and loaded to the Sephadex G-25 column (PD10, Amersham), 10 ml. Column was equilibrate and eluted with the 0.1 M phosphate buffer, pH 7.5, containing 1% BSA. The labeled MANF started to elute at 3.0 ml.

We collected 6-8 fractions of 1 ml and counted the fractions so that we took 2 µl of each fraction to the gamma counter. Fraction 4 contain MANF and that was collected. 1 ml of MANF1 was concentrated at YM10 and 2 µl counted 250,000 cpm. Concentration at 13,000 rpm, 50 min 5° C. The final volume of the concentrated MANF was approximately 130 µl-150 µl.

Results

Our data indicate that DA, hippocampal and cortical neurons specifically bind 125I-labelled MANF and CDNF. In competition assays, excess of unlabelled MANF is unable to displace 125I-labelled CDNF, clearly demonstrating that CDNF and MANF bind to different receptors (FIG. 29). The fact that CDNF is retrogradely transported from the rat striatum to substantia nigra, whereas MANF is not, is further supporting the idea that CDNF and MANF bind to different receptors.

Example 7

Synergistic Neurorestorative Effect of MANF and GDNF

The synergistic neurorestorative effect of MANF and GDNF is studied in an experimental model of Parkinson's disease. Combined intrastriatal injections of MANF (10 ug) and GDNF (10 ug) is given four weeks after intrastriatal 6-OHDA in order to determine if MANF and GDNF rescue dopaminergic neurons by different mechanisms.

Neurorestorative activity of MANF and GDNF is studied by injecting the animals unilaterally into striatum with 6-OHDA (20 µg/4 µl) and four weeks thereafter into the same location with MANF (10 µg in 4 µl of PBS), GDNF (10 µg in 4 µl of PBS), MANF+GDNF (10 ug of each in 4 ul of PBS) or vehicle (controls).

D-Amphetamine (2.5 mg kg i.p.) is used to induce rotational activity in rats with unilateral lesion of nigrostriatal dopaminergic nerves. Behavioral tests are carried out 1 week before (i.e. 3 weeks after 6-OHDA injection) and 2, 4, 6, and 8 weeks after the injection of the trophic factors. Following the behavioural experiments rats are anesthetized and perfused transcardially and their brains are processed for immunohistochemistry.

Example 8

Synergistic Neurorestorative Effect of MANF and GDNF

We have studied CDNF survival promoting activity for DA neurons using a rat unilateral 6-OHDA lesion model of PD in two paradigms—neuroprotective and neurorestorative, and our results show that CDNF has also a very potent neurorestorative effect in the rat model of PD (Lindholm et al., 2007). However, compared to individual neurotrophic factors, the combination of CDNF and MANF may be more efficient in the treatment of PD. Indeed, we have found that MANF and CDNF bind to different receptors. It may be that MANF and CDNF activate completely different signalling pathways than GDNF. MANF and CDNF may have anti-inflammatory effects that could be important in the treatment of PD. Based on that we hypothesize that MANF/CDNF and GDNF may potentiate each other or even have additive effects in PD models.

Neurorestorative Model of PD

Briefly, rats receive 20 µg of 6-OHDA intrastriatally and 4 weeks later a mixture of GDNF, MANF and CDNF, 10 µg each, in different combinations, is injected into striatum. Behavioral studies are followed by stereological analysis of the number of neurons and fiber density as described (Lindholm et al., 2007; Mijatovic et al., 2007). Control rats receive MANF, CDNF or GDNF alone.

Example 9

Materials and Methods

In Vitro Cultures of Dopaminergic Neurons and the Survival Assay

Cells were isolated from dissected midbrain floors of E12.5 NMRI mouse as described previously (Jordan et al., 1997).

25,000 cells were plated per 7 mm poly-orithine coated microisland on the 4-well dishes and tested proteins were added 30 min after plating. Each experiment included 4-8 independent replicates per protein concentration and 14 independent negative (PBS buffer) controls. Cells were fixed and stained for TH-immunoreactivity using standard protocols. Images of the whole microisland were obtained using Leica M2FL III microscope, the number of viable TH-positive cells per microisland was counted using ImagePro 6.0 software and the total TH immunoflourescence signal from all the microislands was measured using Adobe Photoshop software. Random microislands were counted manually to verify the software generated data. In addition, the impact of different paradigms of TH culture on the outcome of MANF survival experiments were tested: effects of plating densities of cells was tested on different matrixes (poly-lysine versus poly-ornithine coated with different concentrations of laminin), mechanical and enzymatic isolation of neurons was compared and different lengths of serum (FBS) priming of the neuronal cultures was assayed. All experiments yielded in similar results, that is, GDNF acts as a potent neurotrophic factor for the dopamine neurons, while MANF does not. FIGS. 30 and 31 presents data from 3 independent experiments. Within each experiment, GDNF significantly enhanced the survival of the dopamine neurons ($p<0.01$) while MANF did not. Data is presented as % of average value of the positive control (GDNF 10 ng/ml). For GDNF, $p<0.000001$ (two tailed homoscedastic student's T-test).

Results

The possible survival promoting activity of purified recombinant human MANF protein was tested in primary cultures of E12.5 mice midbrain neurons. Because the outcome of survival experiments with primary dopaminergic cultures is known to be highly variable and the conventional protocols for evaluating survival effects in primary dopaminergic cultures include error prone visual counting procedures of randomly selected microscopic fields which also may bias the interpretation of the data, we developed a blind digitalized quantification method to compare survival properties of MANF and GDNF in vitro. Unlike GDNF which in accordance with previous results strongly promoted the survival and TH expression in dopaminergic cells, MANF had no statistically significant effect (FIGS. 30, 31). Unlike response to GDNF, dopaminergic neurons did not show enhanced neurite outgrowth after treatment with MANF. Similar results were obtained with mutated recombinant MANF (176P) protein produced in our laboratory. This is in contrast to the data disclosed by Petrova et al. (2003).

TABLE 1

Amino acid identity (%)* of MANF and CDNF proteins between selected organisms.

| | H.s. MANF | H.s. CDNF | M.m. MANF | X.l. MANF | D.r. MANF |
|---|---|---|---|---|---|
| H.s. CDNF | 59 | | | | |
| M.m. MANF | 98 | 59 | | | |
| X.l. MANF | 82 | 57 | 82 | | |
| D.r. MANF | 72 | 55 | 72 | 78 | |
| C.e. MANF | 50 | 46 | 50 | 51 | 49 |

*Signal sequences omitted. H.s., Homo sapiens; M.m., Mus musculus; X.l., Xenopus laevis; D.r., Danio rerio; C.e., Caenorhabditis elegans.

REFERENCES

Airaksinen M S, Saarma M (2002) The GDNF family: signalling, biological functions and therapeutic value. Nat Rev Neurosci 3:383-394.

Arenas E, Trupp M, Åkerud P, Ibanez C F (1995) GDNF prevents degeneration and promotes the phenotype of brain noradrenergic neurons in vivo. Neuron 15:1465-1473.

Arvidsson A, Kokaia Z, Airaksinen M S, Saarma M, Lindvall O (2001) Stroke induces widespread changes of gene expression for glial cell line-derived neurotrophic factor family receptors in the adult rat brain. Neuroscience 106:27-41.

Bespalov M M, Saarma M (2007) GDNF family receptor complexes are emerging drug targets. Trends Pharmacol Sci 28:68-74.

Binder D K, Croll S D, Gall C M, Scharfman H E (2001) BDNF and epilepsy: too much of a good thing? Trends Neurosci 24:47-53.

Burke R E (2003) Postnatal developmental programmed cell death in dopamine neurons. Ann N Y Acad Sci 991:69-79.

CCP4 (1994) Programs for protein crystallography. Acta Cryst. D50:760-763.

Chen S T, Hsu C Y, Hogan E L, Maricq H, Balentine J D. 1986. A model of focal ischemic stroke in the rat: reproducible extensive cortical infarction. Stroke 17(4):738-743.

Gash D M, Zhang Z, Ovadia A, Cass W A, Yi A, Simmerman L, Russell D, Martin D, Lapchak P A, Collins F, Hoffer B J, Gerhardt G A (1996) Functional recovery in parkinsonian monkeys treated with GDNF. Nature 380:252-255.

Gill S S, Patel N K, Hotton G R, O'Sullivan K, McCarter R, Bunnage M, Brooks D J, Svendsen C N, Heywood P (2003) Direct brain infusion of glial cell line-derived neurotrophic factor in Parkinson disease. Nat Med 9:589-595.

Grondin R, Zhang Z, Yi A, Cass W A, Maswood N, Andersen A H, Elsberry D D, Klein M C, Gerhardt G A, Gash D M (2002) Chronic, controlled GDNF infusion promotes structural and functional recovery in advanced parkinsonian monkeys. Brain 125:2191-201.

Gustafsson E, Lindvall O, Kokaia Z (2003) Intraventricular infusion of TrkB-Fc fusion protein promotes ischemia-induced neurogenesis in adult rat dentate gyrus. Stroke 34:2710-2715.

Emfors P, Bengzon J, Kokaia Z, Persson H, Lindvall O (1991) Increased levels of messenger RNAs for neurotrophic factors in the brain during kindling epileptogenesis. Neuron 7:165-176.

Hoffer B J, Hoffman A, Bowenkamp K, Huettl P, Hudson J, Martin D, Lin L F, Gerhardt G A (1994) Glial cell line-derived neurotrophic factor reverses toxin-induced injury to midbrain dopaminergic neurons in vivo. Neurosci Lett 182:107-111.

Huang E J, Reichardt L F (2001) Neurotrophins: roles in neuronal development and function. Annu Rev Neurosci 24:677-736.

Jakubs K, Nanobashvili A, Bonde S, Ekdahl C T, Kokaia Z, Kokaia M, Lindvall 0 (2006) Environment matters: synaptic properties of neurons born in the epileptic adult brain develop to reduce excitability. Neuron 52:1047-1059.

Jin G, Omori N, Li F, Nagano I, Manabe Y, Shoji M, Abe K (2003) Protection against ischemic brain damage by GDNF affecting cell survival and death signals. Neurol Res 25:249-253.

Jordan J, Böttner M, Schluesener H J, Unsicker K, Krieglstein K. (1997) Bone morphogenetic proteins: neurotrophic roles for midbrain dopaminergic neurons and implications of astroglial cells. Eur J. Neurosci. 9:1699-1709.

Kabsch, W. (1993). Automatic processing of rotation diffraction data from crystals of initially unknown symmetry and cell constants. J. Appl. Crystallogr. 26, 795-800.

Kearns C M, Gash D M (1995) GDNF protects nigral dopamine neurons against 6-hydroxydopamine in vivo. Brain Res 672:104-111.

Kokaia Z, Airaksinen M S, Nanobashvili A, Larsson E, Kujamaki E, Lindvall O, Saarma M (1999) GDNF family ligands and receptors are differentially regulated after brain insults in the rat. Eur J Neurosci 11:1202-1216.

Kokaia Z, Lindvall O (2003). Neurogenesis after ischaemic brain insults. Curr Opin Neurobiol 13:127-132.

Kramer E R, Aron L, Ramakers G M, Seitz S, Zhuang X, Beyer K, Smidt M P, Klein R (2007) Absence of Ret signaling in mice causes progressive and late degeneration of the nigrostriatal system. PLoS Biol 5:e39 doi:10.1371.

Klieglstein K (2004) Factors promoting survival of mesencephalic dopaminergic neurons. Cell Tissue Res 318:73-80.

Kuipers S D, Bramham C R (2006) Brain-derived neurotrophic factor mechanisms and function in adult synaptic plasticity: new insights and implications for therapy. Curr Opin Drug Discov Devel 9:580-586.

Lang A E et al. (2006) Randomized controlled trial of intraputamenal glial cell line-derived neurotrophic factor infusion in Parkinson disease. Ann Neurol 59:459-466.

Laskowski, R. A., MacArthur, M. W., S., M. D. & M., T. J. (1993). PROCHECK: a program to check the stereochemical quality of protein structures. J. Appl. Crystallogr. 26, 283-291.

Lin L F, Doherty D H, Lile J D, Bektesh S, Collins F (1993) GDNF: a glial cell line-derived neurotrophic factor for midbrain dopaminergic neurons. Science 260:1130-1132.

Lindholm P, Voutilainen M H, Lauren J, Peranen J, Leppanen V M, Andressoo J O, Lindahl M, Janhunen S, Kalkkinen N, Timmusk T, Tuominen R K, Saarma M (2007) Novel neurotrophic factor CDNF protects and rescues midbrain dopamine neurons in vivo. Nature 448:73-77.

Lindvall O, Ernfors P, Bengzon J, Kokaia Z, Smith M L, Siesjö B K, Persson H (1992) Differential regulation of mRNAs for nerve growth factor, brain-derived neurotrophic factor, and neurotrophin 3 in the adult rat brain following cerebral ischemia and hypoglycemic coma. Proc Natl Acad Sci USA 89:648-652.

Lothman E W, Beitram E H, Bekenstein J W, Perlin J B (1989) Self-sustaining limbic status epilepticus induced by continuous hippocampal stimulation: electrographic and behavioral characteristics. Epilepsy Res 3: 107-119.

Mijatovic J, Airavaara M, Planken A, Auvinen P, Raasmaja A, Piepponen T P, Costantini F, Ahtee L, Saarma M. (2007). Constitutive Ret activity in knock-in multiple endocrine neoplasia type B mice induces profound elevation of brain dopamine concentration via enhanced synthesis and increases the number of TH-positive cells in the substantia nigra. J. Neurosci. 27:4799-809.

Mizobuchi N, Hoseki J, Kubota H, Toyokuni S, Nozaki J, Naitoh M, Koizumi A, Nagata K (2007) ARMET is a soluble ER protein induced by the unfolded protein response via ERSE-II element. Cell Struct Funct 32:41-50.

Murshudov, G. N., Vagin, A. A., Lebedev, A., Wilson, K. S. & Dodson, E. J. (1999). Efficient anisotropic refinement of niacromolecular structures using FFT. Acta Crystallog. sEct. D 55, 247-255.

Oo T F, Burke R E (1997) The time course of developmental cell death in phenotypically defined dopaminergic neurons of the substantia nigra. Brain Res Dev Brain Res 98:191-196.

Patel N K, Bunnage M, Plaha P, Svendsen C N, Heywood P, Gill S S (2005) Intraputamenal infusion of glial cell line-derived neurotrophic factor in PD: a two-year outcome study. Ann Neurol 57:298-302.

Petrova P S, Raibekas A, Pevsner J, Vigo N, Anafi M, Moore M K, Peaire A E, Shridhar V, Smith D I, Kelly J, Durocher Y, Commissiong J W (2003) MANF: a new mesencephalic, astrocyte-derived neurotrophic factor with selectivity for dopaminergic neurons. J Mol Neurosci 20:173-187.

Peranen J, Furahjelm J (2001) Expression, purification and properties of Rab8 function in actin cortical skeleton organization and polarized transport. Methods Enzymol 329: 188-196.

Peränen J, Rikkonen M, Hyvönen M, Kääriäinen L (1996) T7 vectors with a modified T7lac promoter for expression of proteins in Escherichia coli. Anal Biochem 236:371-373.

Poutanen M, Salusjärvi L, Ruohonen L, Penttilä M, Kallkinen N (2001) Use of matrix-assisted laser desorption/ionization time-of-flight mass mapping and nanospray liquid chromatography/electrospray ionization tandem mass spectrometry sequence tag analysis for high sensitivity identification of yeast proteins separated by two-dimensional gel electrophoresis. Rapid Commun Mass Spectrom 15:1685-1692.

Racine R J (1972) Modification of seizure activity by electrical stimulation. II. Motor seizure. Electroencephalogr Clin Neurophysiol 32: 281-294.

Reeben M, Laurikainen A, Hiltunen J O, Castrén E and Saarma M (1997) The messenger RNAs for both glial cell line-derived neurotrophic factor receptors, c-RET and GDNFRα, are induced in the rat brain in response to kainite-induced excitation. Neuroscience 83:151-159.

Sauer H, Rosenblad C, Björklund A (1995) Glial cell line-derived neurotrophic factor but not transforming growth factor beta 3 prevents delayed degeneration of nigral dopaminergic neurons following striatal 6-hydroxydopamine lesion. Proc Natl Acad Sci USA 92:8935-8939.

Schaar D G, Sieber B A, Dreyfus C F, Black I B (1993) Regional and cell-specific expression of GDNF in rat brain. Exp Neurol 124:368-371.

Schäbitz W R, Steigleder T, Cooper-Kuhn C M, Schwab S, Sommer C, Schneider A, Kuhn H G (2007) Intravenous brain-derived neurotrophic factor enhances poststroke sensorimotor recovery and stimulates neurogenesis. Stroke 38:2165-2172.

Smith M L, Auer R N, Siesjö B K (1984) The density and distribution of ischemic brain injury in the rat following 2-10 min of forebrain ischemia. Acta Neuropathol 64:319-332.

Springer J E, Mu X, Bergmann L W, Trojanowski J Q (1994) Expression of GDNF mRNA in rat and human nervous tissue. Exp Neurol 127:167-170.

Stromberg I, Björklund L, Johansson M, Tomac A, Collins F, Olson L, Hoffer B, Humpel C (1993) Glial cell line-derived neurotrophic factor is expressed in the developing but not adult striatum and stimulates developing dopamine neurons in vivo. Exp Neurol 124:401-412.

Suvanto P, Hiltunen J O, Arumae U, Moshnyakov M, Sariola H, Sainio K, Saarma M (1996) Localization of glial cell line-derived neurotrophic factor (GDNF) mRNA in embryonic rat by in situ hybridization. Eur J Neurosci 8:816-822.

Tomac A, Lindqvist E, Lin L F, Ögren S O, Young D, Hoffer B J, Olson L (1995) Protection and repair of the nigrostriatal dopaminergic system by GDNF in vivo. Nature 373: 335-339.

Trupp M, Ryden M, Jornvall H, Funakoshi H, Timmusk T, Arenas E, Ibanez C F (1995) Peripheral expression and biological activities of GDNF, a new neurotrophic factor for avian and mammalian peripheral neurons. J Cell Biol 130:137-148.

Vagin, A. and Teplyakov, A. (2000) An approach to multi-copy search in molecular replacement. Acta Cryst., D56 1622-4 (2000)

Zhao H., Kinnunen P. K. (2002). Binding of the antimicrobial peptide temporin L to liposomes assessed by Trp fluorescence. J. Biol. Chem. 277:25170-25177.

What is claimed:

1. A method of treatment of an individual having Parkinson's disease, said method comprising:

administering by directly injecting a therapeutically effective amount of an expression vector to the central nervous system of the individual having Parkinson's disease, wherein said vector comprises a promoter sequence capable of directing the expression of an operably linked polynucleotide in a mammalian cell, wherein said polynucleotide encodes a polypeptide having SEQ ID NO:2 or a functional fragment thereof, wherein said polypeptide is a mesencephalic astrocyte-derived neurotrophic factor (MANF) polypeptide, and wherein said functional fragment is a MANF polypeptide having SEQ ID NO:4 and is capable of preventing the 6-hydroxydopamine (6-OHDA)-induced degeneration of dopaminergic neurons.

* * * * *